US012569700B2

(12) United States Patent
Parry et al.

(10) Patent No.: US 12,569,700 B2
(45) Date of Patent: *Mar. 10, 2026

(54) METHODS OF USE OF ULTRA-HIGH DOSE RATE RADIATION AND THERAPEUTIC AGENT

(71) Applicant: Varian Medical Systems, Inc., Palo Alto, CA (US)

(72) Inventors: Renate Parry, Oakland, CA (US); Eric Abel, San Jose, CA (US); Swati Girdhani, Fremont, CA (US); Stanley Mansfield, Oakland, CA (US); Patrick Kupelian, Los Angeles, CA (US); Deepak Khuntia, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 18/455,506

(22) Filed: Aug. 24, 2023

(65) Prior Publication Data

US 2024/0100361 A1     Mar. 28, 2024

Related U.S. Application Data

(63) Continuation of application No. 17/486,169, filed on Sep. 27, 2021, now Pat. No. 11,771,920, which is a
(Continued)

(51) Int. Cl.
*A61K 41/00*     (2020.01)
*A61K 9/00*     (2006.01)
(Continued)

(52) U.S. Cl.
CPC .......... *A61N 5/1031* (2013.01); *A61K 9/0009* (2013.01); *A61K 9/141* (2013.01);
(Continued)

(58) Field of Classification Search
CPC ...... A61K 41/0038; A61N 5/10; A61N 5/103; A61N 5/1031; A61N 5/1042;
(Continued)

(56) References Cited

U.S. PATENT DOCUMENTS 6,125,295 A     9/2000   Cash, Jr. et al.
6,222,544 B1     4/2001   Tarr et al.
(Continued)

FOREIGN PATENT DOCUMENTS

CN     101927065 A     12/2010
CN     104001270 A     8/2014
(Continued)

OTHER PUBLICATIONS

Natalia Matuszak et al., FLASH radiotherapy: an emerging approach in radiation therapy, reports of Practical Oncology and Radiotherapy. May 19, 2022; 27(2): pp. 344-351. (Year: 2022).*
(Continued)

*Primary Examiner* — Allen C. Ho
(74) *Attorney, Agent, or Firm* — COOLEY LLP

(57)     ABSTRACT

Methods for treating tumors by administering FLASH radiation and a therapeutic agent to a patient with cancer are disclosed. The methods provide the dual benefits of anti-tumor efficacy plus normal tissue protection when combining therapeutic agents with FLASH radiation to treat cancer patients. The methods described herein also allow for the classification of patients into groups for receiving optimized radiation treatment in combination with a therapeutic agent based on patient-specific biomarker signatures. Also provided are radiation treatment planning methods and systems incorporating FLASH radiation and therapeutic agents.

17 Claims, 24 Drawing Sheets

Related U.S. Application Data continuation of application No. 16/041,636, filed on Jul. 20, 2018, now Pat. No. 11,173,325.

(60) Provisional application No. 62/700,783, filed on Jul. 19, 2018, provisional application No. 62/535,682, filed on Jul. 21, 2017.

(51) Int. Cl.

| | |
|---|---|
| *A61K 9/14* | (2006.01) |
| *A61K 9/51* | (2006.01) |
| *A61K 31/352* | (2006.01) |
| *A61K 31/366* | (2006.01) |
| *A61K 31/404* | (2006.01) |
| *A61K 31/436* | (2006.01) |
| *A61K 31/4439* | (2006.01) |
| *A61K 33/242* | (2019.01) |
| *A61K 33/244* | (2019.01) |
| *A61K 45/06* | (2006.01) |
| *A61N 5/10* | (2006.01) |
| *A61P 35/00* | (2006.01) |
| *G16H 20/40* | (2018.01) |

(52) U.S. Cl.
CPC .............. *A61K 9/51* (2013.01); *A61K 31/352* (2013.01); *A61K 31/366* (2013.01); *A61K 31/404* (2013.01); *A61K 31/436* (2013.01); *A61K 31/4439* (2013.01); *A61K 33/242* (2019.01); *A61K 33/244* (2019.01); *A61K 41/0038* (2013.01); *A61K 45/06* (2013.01); *A61N 5/1042* (2013.01); *A61N 5/1084* (2013.01); *A61P 35/00* (2018.01); *G16H 20/40* (2018.01); *A61N 5/1043* (2013.01); *A61N 5/1045* (2013.01); *A61N 2005/1087* (2013.01); *A61N 2005/1088* (2013.01); *A61N 2005/1089* (2013.01); *A61N 2005/109* (2013.01); *A61N 2005/1098* (2013.01)

(58) Field of Classification Search
CPC .. A61N 5/1043; A61N 5/1045; A61N 5/1047; A61N 5/1084; A61N 2005/1087; A61N 2005/1098
USPC ............................................... 378/65; 702/19
See application file for complete search history.

(56) References Cited

U.S. PATENT DOCUMENTS

| | | | |
|---|---|---|---|
| 6,260,005 | B1 | 7/2001 | Yang et al. |
| 6,379,380 | B1 | 4/2002 | Satz |
| 6,411,675 | B1 | 6/2002 | Llacer |
| 6,504,899 | B2 | 1/2003 | Pugachev et al. |
| 6,993,112 | B2 | 1/2006 | Hesse |
| 7,194,063 | B2 | 3/2007 | Dilmanian et al. |
| 7,268,358 | B2 | 9/2007 | Ma et al. |
| 7,453,983 | B2 | 11/2008 | Schildkraut et al. |
| 7,486,984 | B2 | 2/2009 | Carroll |
| 7,515,681 | B2 | 4/2009 | Ebstein |
| 7,560,715 | B2 | 7/2009 | Pedroni |
| 7,590,219 | B2 | 9/2009 | Maurer, Jr. et al. |
| 7,613,501 | B2 * | 11/2009 | Scherch ............... A61N 5/1049 378/65 |
| 7,616,735 | B2 | 11/2009 | Maciunas et al. |
| 7,623,623 | B2 | 11/2009 | Raanes et al. |
| 7,741,624 | B1 | 6/2010 | Sahadevan |
| 7,778,691 | B2 | 8/2010 | Zhang et al. |
| 7,801,270 | B2 | 9/2010 | Nord et al. |
| 7,807,982 | B2 | 10/2010 | Nishiuchi et al. |
| 7,831,289 | B2 | 11/2010 | Riker et al. |
| 7,835,492 | B1 | 11/2010 | Sahadevan |
| 8,029,808 | B2 | 10/2011 | Srivastava |
| 8,034,375 | B2 | 10/2011 | Desai et al. |
| 8,139,714 | B1 | 3/2012 | Sahadevan |
| 8,173,983 | B1 | 5/2012 | Sahadevan |
| 8,306,184 | B2 | 11/2012 | Chang et al. |
| 8,401,148 | B2 | 3/2013 | Lu et al. |
| 8,406,844 | B2 | 3/2013 | Ruchala et al. |
| 8,559,596 | B2 | 10/2013 | Thomson et al. |
| 8,600,003 | B2 | 12/2013 | Zhou et al. |
| 8,613,694 | B2 | 12/2013 | Walsh |
| 8,618,521 | B2 * | 12/2013 | Loo ..................... A61N 5/1043 250/492.1 |
| 8,636,636 | B2 | 1/2014 | Shukla et al. |
| 8,644,571 | B1 | 2/2014 | Schulte et al. |
| 8,716,663 | B2 | 5/2014 | Brusasco et al. |
| 8,847,179 | B2 | 9/2014 | Fujitaka et al. |
| 8,884,181 | B2 | 11/2014 | Houde et al. |
| 8,948,341 | B2 | 2/2015 | Beckman |
| 8,986,186 | B2 | 3/2015 | Zhang et al. |
| 8,995,608 | B2 | 3/2015 | Zhou et al. |
| 9,033,859 | B2 | 5/2015 | Fieres et al. |
| 9,114,157 | B2 | 8/2015 | Strober et al. |
| 9,132,281 | B2 | 9/2015 | Zeng et al. |
| 9,149,656 | B2 | 10/2015 | Tanabe |
| 9,155,908 | B2 | 10/2015 | Meltsner et al. |
| 9,155,910 | B1 | 10/2015 | Sahadevan |
| 9,216,302 | B2 | 12/2015 | Kuwahara et al. |
| 9,233,260 | B2 | 1/2016 | Slatkin et al. |
| 9,283,406 | B2 | 3/2016 | Prieels |
| 9,308,391 | B2 | 4/2016 | Liu et al. |
| 9,320,813 | B2 | 4/2016 | Peyman |
| 9,333,374 | B2 | 5/2016 | Iwata |
| 9,386,682 | B2 | 7/2016 | Tantawi et al. |
| 9,393,439 | B2 | 7/2016 | Goer |
| 9,517,358 | B2 | 12/2016 | Velthuis et al. |
| 9,545,444 | B2 | 1/2017 | Strober et al. |
| 9,616,106 | B2 | 4/2017 | Basile |
| 9,636,381 | B2 | 5/2017 | Basile |
| 9,636,525 | B1 | 5/2017 | Sahadevan |
| 9,649,298 | B2 | 5/2017 | Djonov et al. |
| 9,656,098 | B2 | 5/2017 | Goer |
| 9,694,204 | B2 | 7/2017 | Hardemark |
| 9,776,017 | B2 | 10/2017 | Flynn et al. |
| 9,786,093 | B2 | 10/2017 | Svensson |
| 9,795,806 | B2 | 10/2017 | Matsuzaki et al. |
| 9,855,445 | B2 | 1/2018 | Mansfield |
| 9,884,206 | B2 | 2/2018 | Schulte et al. |
| 9,931,522 | B2 | 4/2018 | Bharadwaj et al. |
| 9,938,583 | B2 | 4/2018 | Parry |
| 9,962,562 | B2 | 5/2018 | Fahrig et al. |
| 9,974,977 | B2 | 5/2018 | Lachaine et al. |
| 9,987,502 | B1 | 6/2018 | Gattiker et al. |
| 9,990,715 | B2 | 6/2018 | Enderling et al. |
| 10,007,961 | B2 | 6/2018 | Grudzinski et al. |
| 10,071,264 | B2 | 9/2018 | Liger |
| 10,080,911 | B2 | 9/2018 | Zankowski et al. |
| 10,092,774 | B1 | 10/2018 | Vanderstraten et al. |
| 10,098,952 | B2 | 10/2018 | Borghi et al. |
| 10,124,194 | B2 | 11/2018 | Dilmanian et al. |
| 10,166,405 | B2 | 1/2019 | Nguyen |
| 10,183,179 | B1 | 1/2019 | Smith et al. |
| 10,206,871 | B2 | 2/2019 | Lin et al. |
| 10,232,193 | B2 | 3/2019 | Iseki |
| 10,245,448 | B2 | 4/2019 | Heese |
| 10,258,810 | B2 | 4/2019 | Zwart et al. |
| 10,279,196 | B2 | 5/2019 | West et al. |
| 10,307,614 | B2 | 6/2019 | Schnarr |
| 10,315,047 | B2 | 6/2019 | Glimelius et al. |
| 10,413,755 | B1 | 9/2019 | Sahadevan |
| 10,449,388 | B2 | 10/2019 | Yin et al. |
| 10,456,468 | B2 | 10/2019 | Unger |
| 10,500,278 | B2 | 12/2019 | Abazeed |
| 10,507,337 | B2 * | 12/2019 | Willcut ............... A61N 5/1038 |
| 10,525,285 | B1 | 1/2020 | Friedman |
| 10,549,117 | B2 | 2/2020 | Vanderstraten et al. |
| 10,603,514 | B2 | 3/2020 | Grittani et al. |
| 10,609,806 | B2 | 3/2020 | Roecken et al. |
| 10,632,179 | B2 | 4/2020 | Brady-Kalnay |
| 10,661,100 | B2 | 5/2020 | Shen |
| 10,695,543 | B2 | 6/2020 | Agah et al. |

(56) References Cited

U.S. PATENT DOCUMENTS

| | | | |
|---|---|---|---|
| 10,697,023 B2 | 6/2020 | Scott et al. | |
| 10,702,716 B2 | 7/2020 | Heese | |
| 10,737,117 B2 | 8/2020 | Mori et al. | |
| 10,762,167 B2 | 9/2020 | Hartman et al. | |
| 10,843,011 B2 | 11/2020 | Trail et al. | |
| 10,857,391 B2 | 12/2020 | Stahl et al. | |
| 10,946,215 B2 | 3/2021 | Sjolund | |
| 11,173,325 B2 | 11/2021 | Parry et al. | |
| 11,273,326 B2 | 3/2022 | Ohishi | |
| 11,318,193 B2 | 5/2022 | Akle et al. | |
| 11,389,668 B2 | 7/2022 | Jin et al. | |
| 11,771,920 B2 | 10/2023 | Parry et al. | |
| 11,918,830 B2 * | 3/2024 | Michaud | A61N 5/1077 |
| 11,918,831 B2 * | 3/2024 | Michaud | A61N 5/1077 |
| 11,925,818 B2 * | 3/2024 | Michaud | A61N 5/1044 |
| 11,986,672 B2 * | 5/2024 | Abel | A61N 5/103 |
| 12,083,356 B2 * | 9/2024 | Folkerts | A61N 5/1031 |
| 12,186,587 B2 * | 1/2025 | Lansonneur | A61N 5/1031 |
| 12,324,933 B2 * | 6/2025 | Bourhis | A61N 5/1077 |
| 12,370,374 B2 * | 7/2025 | Sharma | A61N 5/1031 |
| 2007/0287878 A1 | 12/2007 | Fantini et al. | |
| 2010/0178245 A1 | 7/2010 | Arnsdorf et al. | |
| 2010/0329413 A1 | 12/2010 | Zhou et al. | |
| 2011/0006224 A1 | 1/2011 | Maltz et al. | |
| 2011/0091015 A1 | 4/2011 | Yu et al. | |
| 2011/0189169 A1 | 8/2011 | Abounader et al. | |
| 2012/0157746 A1 | 6/2012 | Meltsner et al. | |
| 2012/0171745 A1 | 7/2012 | Itoh | |
| 2013/0231516 A1 | 9/2013 | Loo et al. | |
| 2013/0274233 A1 | 10/2013 | Wang et al. | |
| 2014/0275706 A1 | 9/2014 | Dean et al. | |
| 2015/0011817 A1 | 1/2015 | Feng | |
| 2015/0202464 A1 | 7/2015 | Brand et al. | |
| 2015/0306423 A1 | 10/2015 | Bharat et al. | |
| 2016/0279444 A1 | 9/2016 | Schlosser | |
| 2016/0287905 A1 | 10/2016 | Liger | |
| 2016/0310764 A1 | 10/2016 | Bharadwaj et al. | |
| 2017/0189721 A1 | 7/2017 | Sumanaweera et al. | |
| 2017/0203129 A1 | 7/2017 | Dessy | |
| 2017/0231903 A1 | 8/2017 | Lin et al. | |
| 2017/0281973 A1 | 10/2017 | Allen et al. | |
| 2018/0021594 A1 | 1/2018 | Papp et al. | |
| 2018/0043183 A1 | 2/2018 | Sheng et al. | |
| 2018/0056090 A1 | 3/2018 | Jordan et al. | |
| 2018/0099154 A1 | 4/2018 | Prieels | |
| 2018/0099155 A1 | 4/2018 | Prieels et al. | |
| 2018/0099159 A1 | 4/2018 | Forton et al. | |
| 2018/0154183 A1 | 6/2018 | Sahadevan | |
| 2018/0161600 A1 | 6/2018 | Bowman et al. | |
| 2018/0197303 A1 | 7/2018 | Jordan et al. | |
| 2018/0236268 A1 | 8/2018 | Zwart et al. | |
| 2019/0022407 A1 | 1/2019 | Abel et al. | |
| 2019/0022411 A1 | 1/2019 | Parry et al. | |
| 2019/0054315 A1 | 2/2019 | Isola et al. | |
| 2019/0070435 A1 | 3/2019 | Joe Anto et al. | |
| 2019/0114765 A1 | 4/2019 | Enderling et al. | |
| 2019/0168027 A1 | 6/2019 | Smith et al. | |
| 2019/0224294 A1 | 7/2019 | Akle et al. | |
| 2019/0255361 A1 | 8/2019 | Mansfield | |
| 2019/0299027 A1 | 10/2019 | Fujii et al. | |
| 2019/0299029 A1 | 10/2019 | Inoue | |
| 2019/0351259 A1 | 11/2019 | Lee et al. | |
| 2020/0001118 A1 | 1/2020 | Snider, III et al. | |
| 2020/0022248 A1 | 1/2020 | Yi et al. | |
| 2020/0030633 A1 | 1/2020 | Van Heteren et al. | |
| 2020/0035438 A1 | 1/2020 | Star-Lack et al. | |
| 2020/0069818 A1 | 3/2020 | Jaskula-Ranga et al. | |
| 2020/0164224 A1 | 5/2020 | Vanderstraten et al. | |
| 2020/0178890 A1 | 6/2020 | Otto | |
| 2020/0197730 A1 | 6/2020 | Safavi-Naeini et al. | |
| 2020/0254279 A1 | 8/2020 | Ohishi | |
| 2020/0269068 A1 | 8/2020 | Abel et al. | |
| 2020/0276456 A1 | 9/2020 | Swerdloff | |
| 2020/0282234 A1 | 9/2020 | Folkerts et al. | |
| 2022/0008750 A1 | 1/2022 | Parry et al. | |

FOREIGN PATENT DOCUMENTS

| | | | |
|---|---|---|---|
| CN | 106730407 A | 5/2017 | |
| CN | 107362464 A | 11/2017 | |
| CN | 109966662 A | 7/2019 | |
| CN | 111481840 A | 8/2020 | |
| CN | 111481841 A | 8/2020 | |
| DE | 102020209913 A1 | 7/2021 | |
| EA | 010207 B1 | 6/2008 | |
| EP | 0979656 A2 | 2/2000 | |
| EP | 3421087 A1 | 1/2019 | |
| EP | 3453427 A1 | 3/2019 | |
| EP | 2823501 B1 | 5/2019 | |
| EP | 3338858 B1 | 6/2019 | |
| EP | 3043863 B1 | 12/2019 | |
| EP | 3586920 A1 | 1/2020 | |
| EP | 3655097 A1 | 5/2020 | |
| EP | 3693974 A1 | 8/2020 | |
| EP | 3384961 B1 | 10/2021 | |
| JP | H08318000 A | 12/1996 | |
| JP | 2019097969 A | 6/2019 | |
| WO | WO-2006039569 A1 | 4/2006 | |
| WO | WO-2007017177 A1 | 2/2007 | |
| WO | WO-2009120999 A2 | 10/2009 | |
| WO | WO-2010018476 A2 | 2/2010 | |
| WO | WO-2013081218 A2 | 6/2013 | |
| WO | WO-2014139493 A1 | 9/2014 | |
| WO | WO-2014144804 A1 | 9/2014 | |
| WO | WO-2014205128 A1 | 12/2014 | |
| WO | WO-2015102680 A2 | 7/2015 | |
| WO | WO-2016122957 A1 | 8/2016 | |
| WO | WO-2016149580 A2 | 9/2016 | |
| WO | WO-2017044562 A1 | 3/2017 | |
| WO | WO-2017156316 A1 | 9/2017 | |
| WO | WO-2017174643 A1 | 10/2017 | |
| WO | WO-2018137772 A1 | 8/2018 | |
| WO | WO-2018152302 A1 | 8/2018 | |
| WO | WO-2018222689 A1 | 12/2018 | |
| WO | WO-2018226671 A1 | 12/2018 | |
| WO | WO-2019018813 A1 | 1/2019 | |
| WO | WO-2019055491 A1 | 3/2019 | |
| WO | WO-2019097250 A1 | 5/2019 | |
| WO | WO-2019103983 A1 | 5/2019 | |
| WO | WO-2019164835 A1 | 8/2019 | |
| WO | WO-2019166702 A1 | 9/2019 | |
| WO | WO-2019169175 A1 | 9/2019 | |
| WO | WO-2019185378 A1 | 10/2019 | |
| WO | WO-2019222436 A2 | 11/2019 | |
| WO | WO-2020018904 A1 | 1/2020 | |
| WO | WO-2020064832 A1 | 4/2020 | |
| WO | WO-2020107121 A1 | 6/2020 | |
| WO | WO-2020159360 A1 | 8/2020 | |

OTHER PUBLICATIONS

Amaldi et al., "Proton and Carbon Linacs for Hadron Therapy", Proceedings of LINAC2014, Geneva, Switzerland, Available Online at http://accelconf.web.cern.ch/AccelConf/LINAC2014/papers/friob02.pdf, 2014, pp. 1207-1212.

Anferov et al., "The Indiana University Midwest Proton Radiation Institute", Proceedings of the 2001 Particle Accelerator Conference, Available Online at https://accelconf.web.cern.ch/accelconf/p01/PAPERS/FOAA004.PDF, Jun. 2001, pp. 645-647.

Application No. PCT/US2018/043171, International Preliminary Report on Patentability, Mailed on Jan. 30, 2020, 7 pages.

Bashkirov et al., "Development of Proton Computed Tomography Detectors for Applications in Hadron Therapy", NIM Nuclear Instruments and Methods in Physics Research A (under press at the time of writing proposal), vol. 809, Feb. 11, 2016, pp. 120-129.

Benedetti et al., "High Gradient Linac for Proton Therapy", Phys. Rev. Accel. Beams, vol. 20, No. 4, Apr. 13, 2017, pp. 040101-1-040101-19.

Bernier et al., "High-Dose Radiation Therapy with or Without Chemotherapy in Treating Patients with Head and Neck Cancer", Available online at: https://clinicaltrials.gov/ct2/show/record/NCT00002555, 1999, 6 pages.

(56)         References Cited

OTHER PUBLICATIONS

Bijan et al., "Evaluation of Energy Deposition and Secondary Particle Production in Proton Therapy of Brain Using a Slab Head Phantom", Reports of Practical Oncology & Radiotherapy, vol. 19, Issue 6, Nov.-Dec. 2014, pp. 376-384.

Bopp et al., "Upgrade Concepts of the PSI Accelerator RF Systems for a Projected 3 mA Operation", CP600, Cyclotrons and Their Applications 2001, Sixteenth International Conference, Dec. 2001, 3 pages.

Buontempo et al., "Enhancing radiosensitivity of melanoma cells through very high dose rate pulses released by a plasma focus device", PLoS ONE, Jun. 29, 2018, 13(6):1-21.

Citrin et al., "Mechanisms of Normal Tissue Injury From Irradiation", Seminars in Radiation Oncology, Oct. 2017, 27(4):316-324.

"Clinical Trials Fall", Stanford Cancer Institute—Clinical Research, Newsletter for Colleagues in the Community, 2016, 12 pages.

Crino et al., "Induction Chemotherapy Plus High-Dose Radiotherapy Versus Radiotherapy Alone in Locally Advanced Unresectable Non-Small-Cell Lung Cancer", Lung Cancer, 1994, 11(3-4), 1994, 1 page.

Dillman et al., "A Randomized Trial of Induction Chemotherapy plus High-Dose Radiation versus Radiation Alone in Stage III Non-Small-Cell Lung Cancer", The New England Journal of Medicine, Oct. 4, 1990, 323(14):940-945.

Dolgashev et al., "Geometric Dependence of Radio-frequency Breakdown in Normal Conducting Accelerating Structures", Applied Physics Letters, Oct. 2010, 97(17):171501-1-171501-3.

Dutreix et al., "Radiobiology", Available Online at: https://web. archive.org/web/20161203131833/https://siric.institut-curie.org/ program/radiobiology, 2016, 6 pages.

Eling et al., "Ultrahigh Dose Rate Synchrotron Microbeam Radiation Therapy. Preclinical Evidence in View of a Clinical Transfer", Available Online at: https://www.sciencedirect.com/science/article/ abs/pii/S0167814019329706, 2019, 13 pages.

Favaudon et al., "Flash Radiotherapy to Spare Healthy Tissue", Medecine/Sciences, Feb. 2015, 31, 6 pages.

Favaudon et al., "Radiotherapie «Flash» A Tres Haut Debit De Dose : Un Moyen D'augmenter L'indice Therapeutique Par Minimisation Des Dommages Aux Tissus Sains?", Cancer/Radiotherapie, Apr. 29, 2015, 19:526-531.

Favaudon et al., Supplementary Materials for "Ultrahigh dose-rate FLASH irradiation increases the differential response between normal and tumor tissue in mice", Science TranslationMedicine. org., Jul. 16, 2014, 6, 18 pages.

Favaudon et al., "Ultrahigh dose-rate FLASH irradiation increases the differential response between normal and tumor tissue in mice", Science TranslationMedicine.org., Jul. 16, 2014, 6, 10 pages.

"Flash Irradiation Delivered in a Clinical Treatment Room", Available Online at: https://iba-worldwide.com/content/pt/proton-flash-irradiation-delivered-clinical-treatment-room, Mar. 8, 2019, 3 pages.

"Flash Proton Delivery Aims to Reduce Radiotherapy Toxicity", Available Online at: https://physicsworld.com/a/flash-proton-delivery-aims-to-reduce-radiotherapy-toxicity/, 2018, 3 pages.

Gerard et al., "Treatment of Anal Canal Carcinoma with High Dose Radiation Therapy and Concomitant Fluorouracil-Cisplatinum. Long-Term Results in 95 Patients", Radiotherapy and Oncology, Mar. 1998, 46(3):249-256.

Haberer et al., "Magnetic Scanning System for Heavy Ion Therapy", Nuclear Instruments and Methods in Physics Research Section A: Accelerators, Spectrometers, Detectors and Associated Equipment, NIM, Elsevie, Jun. 10, 1993, 330(1-2):296-305.

Halbach , "Design of Permanent Multipole Magnets with Oriented Rare Earth Cobalt Material", Nuclear Instruments and Methods, Feb. 1, 1980, 169(1):1-10.

Hellevik et al., "Radiotherapy and the tumor stroma: the importance of dose and fractionation", Frontiers in Oncology, Jan. 21, 2014, 4(1), 12 pages.

Hong et al., "Tumor Hypoxia and Reoxygenation: the Yin and Yang for Radiotherapy", Radiation Oncology Journal, Dec. 28, 2016, 34(4):239-249.

Hsi et al., "Energy Spectrum Control for Modulated Proton Beams", Medical Physics, Available Online at http://www.ncbi.nlm.nih.gov/ pmc/articles/PMC2832068/, Jun. 2009, 36(6):2297-2308.

International Application No. PCT/US2018/043171, "International Search Report and Written Opinion", dated Oct. 30, 2018, 11 pages.

Jensen et al., "X-Band Multi-beam Klystron Design and Progress Report", Vacuum Electronics Conference (IVEC), 2015 IEEE International, Apr. 27-29, 2015, 2 pages.

Kim et al., "High-dose Extended-Field Irradiation and High-Dose-Rate Brachytherapy with Concurrent Chemotherapy for Cervical Cancer With Positive Para-Aortic Lymph Nodes", International Journal of Radiation Oncology, Aug. 1, 2009, 74(5):1522-1528.

Laliscia et al., "Concomitant External-beam Irradiation and Chemotherapy Followed by High-dose Rate Brachytherapy Boost in the Treatment of Squamous Cell Carcinoma of the Vagina: A Single-Center Retrospective Study", Anticancer Research, Apr. 2016, 36(4):1885-1889.

Laurent et al., "Experimental Study of RF Pulsed Heating", Phys. Rev. ST Accel. Beams, Apr. 7, 2011, 14(4):041001-1-041001-21.

Levy, "Flash Irradiation Enhances the Therapeutic Index of Abdominal Radiotherapy in Mice", Available Online at: https://www.biorxiv. org/contenU10.1101/2019.12.12.873414v1.full, 2019, 22 pages.

Lim et al., "Adjustable, Short Focal Length Permanent-magnet Quadrupole Based Electron Beam Final Focus System", Phys. Rev. ST Accel. Beams, Jul. 15, 2005, 8(7):072401-1-072401-17.

Limborg et al., "Designs and High Power Tests of Distributed Coupling Linacs", Valencia, Spain, Available Online at https://ind ico.cern.ch/event/589548/contributions/2615455/attachments/1479738/ 2294080/Mamd ouh_High_ Gradient_ 2017.pdf, Jun. 13-16, 2017, 1-31.

Loo et al., "Delivery of Ultra-Rapid Flash Radiation Therapy and Demonstration of Normal Tissue Sparing After Abdominal Irradiation of Mice", International Journal of Radiation Oncology Biology Physics, Jun. 1, 2017, 98(2), p. E16.

Luo et al., "Effect of Modern High-dose Versus Standard-dose Radiation in Definitive Concurrent Chemo-radiotherapy on Outcome of Esophageal Squamous Cell Cancer: a Meta-analysis", Radiation Oncology, Oct. 17, 2019, 14(178), 22 pages.

Montay-Gruel et al., "Irradiation in a Flash: Unique Sparing of Memory in Mice After Whole Brain Irradiation with Dose Rates Above 100 Gy/s", Radiother Oncol., Sep. 2017, 124(3):365-369.

Park et al. "Senotherapeutics and Their Molecular Mechanism for Improving Aging", Biomolecules & Therapeutics, Nov. 1, 2022, 30(6):490-500.

PCT/US2019/042603 , "International Search Report and Written Opinion", Oct. 30, 2019, 17 pages.

Peach et al., "Pamela—A Model for an FFAG Based Hadron Therapy Machine", Proceedings of PAC07, Albuquerque, New Mexico, USA, Jun. 25-29, 2007, pp. 2880-2882.

Perl et al., "TOPAS: an Innovative Proton Monte Carlo Platform for Research and Clinical Applications", Med. Phys., Nov. 2012, 39(11):6818-6837.

Polster et al., "Extension of TOPAS for the Simulation of Proton Radiation on Molecular and Cellular Endpoints", Phys Med Biol., Jul. 7, 2015, 60(13):5053-5070.

"Radiotherapy and Radiation Biology", Curie Institute, Apr. 21, 2017, 9 pages.

Schuler et al., "Experimental Platform for Ultra-high Dose Rate FLASH Irradiation of Small Animals Using a Clinical Linear Accelerator", Available Online at: https://www.researchgate. neUpublication/309734777_Experimentai_Piatform_for_Uitrahigh_ Dose_Rate_FLASH_Irradiation_of_Smaii_Animals_Using_a_ Ciinicai_Linear_Accelerator, Sep. 2016, 97(1):195-203.

Spratt, D., et al., "Long-term Survival and Toxicity of Patients Treated With Ultra-high-dose IMRT for Localized Prostrate Cancer", International Journal of Radiation: Oncology Biology Physics, 2012, 84(3), 1 page.

Stokes et al., "Organ Preservation for Muscle-Invasive Squamous Cell Carcinoma of the Urinary Bladder in the United States", International Journal of Radiation: Oncology Biology Physics; 2017, 99(2), 1 page.

(56) References Cited

OTHER PUBLICATIONS

Suzuki et al., "Abscopal Effect of High-dose-rate Brachytherapy on Pelvic Bone Metastases From Renal Cell Carcinoma: a Case Report", Journal of Contemporary Brachytherapy, Oct. 30, 2019, 11(5):458-461.

Teckie et al., "Ultra-high-dose Stereotactic Body Radiation Therapy (SBRT) is Feasible for Tumors in the Head and Neck (HN)", International Journal of Radiation: Oncology Biology Physics, 2012, 84(3), 2 pages.

Till et al., "A Direct Measurement of the Radiation Sensitivity of Normal Mouse Bone Marrow Cells", Radiation Research, 2011, 178(2):145-149.

U.S. Appl. No. 62/535,682, Immunophenotyping, Jul. 21, 2017, 1 page.

Ventura et al., "Localized Synchrotron Irradiation of Mouse Skin Induces Persistent Systemic Genotoxic and Immune Responses", Available Online at: http://cancerres.aacrjournals.org/contenUearly/2017/11/06/0008-5472.CAN-17-1066#, Nov. 2017, 23 pages.

Wilson, J. et al., "Ultra-High Dose Rate (FLASH) Radiotherapy: Silver Bullet or Fool's Gold?" Frontiers in Oncology, Jan. 17, 2020, 9(1563):1-9.

Zackrisson, "Biological Effects of High Energy Radiation and Ultra High Dose Rates", Available Online at: https://www.divaportal.org/smash/geUdiva2:769196/FULLTEXT01.pdf, 1991, 48 pages.

Zenghai et al., "Normal Conducting CW Transverse Crab Cavity for Producing Short Pulses in SPEAR3", Proceedings of IPAC2017, Copenhagen, Denmark, May 2017, 2840-2843.

Zhou, "Mechanisms Underlying Flash Radiotherapy, a Novel Way to Enlarge the Differential Responses to Ionizing Radiation Between Normal and Tumor Tissues", Radiation Medicine and Protection, Mar. 2020, 1(1), 25 pages.

Zhu et al., "The Achilles' heel of senescent cells: from transcriptome to senolytic drugs", Aging Cell, 14(4):644-658, Epub Apr. 22, 2015.

Auer et al., "Survival of tumor cells after proton irradiation with ultra-high dose rates," Radiother. Oncol., 2011, 6(139), 8 pages.

Non-Final Office Action for U.S. Appl. No. 16/041,636, by Parry, Renate et al., mailed on Dec. 31, 2020, 18 pages.

Non-Final Office Action for U.S. Appl. No. 17/486,169, by Parry, Renate et al., mailed on Dec. 22, 2022, 8 pages.

Notice of Allowance and Examiner Interview Summary for U.S. Appl. No. 16/041,636, by Parry, Renate et al., mailed on Jul. 6, 2021, 17 pages.

Notice of Allowance for U.S. Appl. No. 17/486,169, by Parry, Renate et al., mailed on May 25, 2023, 9 pages.

Office Action for Chinese Application No. 201980048106.X, by Varian Medical Systems, Inc., mailed Mar. 4, 2023, 16 pages with English Translation.

Office Action for Chinese Application No. 201980048106.X, by Varian Medical Systems, Inc., mailed Oct. 29, 2023, 12 pages with English Translation.

Office Action for Chinese Application No. 201980048106.X, by Varian Medical Systems, Inc., mailed Feb. 5, 2024, 12 pages with English Machine Translation.

Office Action for European Application No. 18752356.8, by Varian Medical Systems, Inc., mailed Mar. 25, 2021, 4 pages.

Office Action for European Application No. 18752356.8, by Varian Medical Systems, Inc., mailed Oct. 13, 2023, 7 pages.

Office Action for European Application No. 18752356.8, by Varian Medical Systems, Inc., mailed Jan. 16, 2025, 7 pages.

Office Action for European Application No. 19749118.6, by Varian Medical Systems, Inc., mailed Aug. 30, 2024, 6 pages.

Schmid et al. "Relative biological effectiveness of pulsed and continuous 20 MeV protons for micronucleus induction in 3D human reconstructed skin tissue" Radiother. Oncol, 2010, 95(1):66-72.

Schmid et al. "The Effectiveness of 20 MeV Protons at Nanosecond Pulse Lengths in Producing Chromosome Aberrations in Human-Hamster Hybrid Cells" Radiation Research, 2011, 175(6):719-727.

Schmid, T.E. et al. "No evidence for a different RBE between pulsed and continuous 20 MeV protons." Radiation research 172.5 (2009): 567-574.

Simoenov et al., "Design, Optimisation and Monte Carlo Simulation of a 3D Range-Modulator for Scanned Particle Therapy," Poster from PTCOG 55 in 2016, 1 page.

Zlobinskaya, O., et al., "The effects of ultra-high dose rate proton irradiation on growth delay in the treatment of human tumor xenografts in nude mice", Radiation Research Feb. 2014, 181(2):177-83.

Aetna, Inc., "Proton Beam, Neutron Beam, and Carbon Ion Radiotherapy", Policy No. 0270, Effective Date Jul. 16, 1998 [online]. Retrieved from: https://www.aetna.com/cpb/medical/data/200_299/0270.html; retrieved on Jul. 31, 2025; 154 pages.

Anferov, V.A. et al. "Scan pattern optimization for uniform proton beam scanning", Medical Physics, 2009; 36(8):3560-3567.

Ashraf, M.R. et al., "Dosimetry for FLASH radiotherapy: a review of tools and the role of radioluminescence and Cherenkov emission", Frontiers in Physics, Aug. 21, 2020; 8:328, doi: 10.3389/fphy.2020.00328, 20 pages.

Author Unknown, "Netherlands Proton Therapy Center Delivers First Clinical Flash Irradiation", Imaging Technology News, May 2, 2019 [online]. Retrieved from: https://www.itnonline.com/content/netherlands-proton-therapy-center-delivers-first-clinical-flash-irradiation, retrieved on Jul. 31, 2025, 1 page.

Author Unknown, "ProNova and medPhoton to Offer Next Generation Beam Delivery, Advanced Imaging for Proton Therapy", Imaging Technology News, Oct. 6, 2014 [online]. Retrieved from: https://www.itnonline.com/content/pronova-and- medphoton-offer-next-generation-beam-delivery-advanced-imaging-proton-therapy, retrieved on Jul. 31, 2025, 1 page.

Bazalova-Carter, M. & Esplen, N., "On the capabilities of conventional x-ray tubes to deliver ultra-high (FLASH) dose rates", Medical Physics, Dec. 2019; 46(12):5690-5695.

Buonanno, M. et al., "Biological effects in normal cells exposed to FLASH dose rate protons", Radiotherapy and Oncology, Oct. 2019; 139:51-55, doi:10.1016/j.radonc.2019.02.009. HHS Public Access Author Manuscript, available in PMC Oct. 1, 2020, 14 pages.

Carlsson, Fredrik, "Utilizing Problem Structure in Optimization of Radiation Therapy", Doctoral Thesis. KTH Engineering Sciences, Stockholm, Sweden, Apr. 2008 [online]. Retrieved from: https://www.raysearchlabs.com/globalassets/about-overview/media-center/wp-re-ev-n-pdfs/publications/thesis-fredrik_light.pdf (retrieval date unknown); 41 pages.

Colangelo, N.W. & Azzam, E.I., "The importance and clinical implications of FLASH ultra-high dose-rate studies for proton and heavy ion radiotherapy", Radiation Research, Jan. 2020; 193(1): 1-4, doi: 10.1667/RR15537.1. HHS Public Access Author Manuscript, available in PMC Jan. 1, 2021, 7 pages.

De Kruijff, R.M., "Flash radiotherapy: ultra-high dose rates to spare healthy tissue", International Journal of Radiation Biology, 2020; 96(4):419-423.

Demizu, Y. et al., "Carbon ion therapy for early-stage non-small-cell lung cancer", BioMed Research International, 2014; 2014:727962, http://dx.doi.org/10.1155/2014/727962, 9 pages.

Diffenderfer, Eric S. et al., "Design, implementation, and in vivo validation of a novel proton FLASH radiation therapy system", International Journal of Radiation Oncology, Biology, Physics, Feb. 1, 2020; 106(2):440-448, doi: 10.1016/j.ijrobp.2019.10.049.

Dokic, I. et al., "Next generation multi-scale biophysical characterization of high precision cancer particle radiotherapy using clinical proton, helium-, carbon- and oxygen ion beams", Oncotarget, Aug. 2016; 7(35):56676-26689.

Durante, M. et al., "Faster and safer? FLASH ultra-high dose rate in radiotherapy", The British Journal of Radiology, 2018; 91:20170628, https://doi.org/10.1259/bjr.20170628, 4 pages.

Engels, E. et al., "Toward personalized synchrotron microbeam radiation therapy", Scientific Reports, 2020; 10:8833, doi: 10.1038/s41598-020-65729-z; 13 pages.

Fan, Q. "Emission Guided Radiation Therapy for Lung and Prostrate Cancers: A Feasibility Study on a Digital Patient," Med. Phys. Nov. 2012; 39(11):7140-7152.

(56) References Cited

OTHER PUBLICATIONS

Favaudon et al., "Ultra-high dose-rate, pulse irradiation to reduce the complications of radiotherapy", Radiotherapy and Oncology, Mar. 2, 20111, vol. 98, Supplement 2, Page S11, https://doi.org/10.1016/S0167-8140(11)71730-3.

Fischer, "PMB launches FLASH radiotherapy system for use in clinical trials" Jun. 29, 2020 [online]. Retrieved from: https://www.dotmed.com/news/story/51662; retrieved on Jul. 31, 2025; 1 page.

Freeman, T., "Flash radiotherapy: from preclinical promise to the first human treatment", Physics World, Aug. 6, 2019 [online]. Retrieved from: https://physicsworld.com/a/flash-radiotherapy-from-preclinical-promise-to-the-first-human-treatment/; retreived on Jul. 31, 2025, 7 pages.

Gierga, D.P., "Is FLASH radiotherapy coming?", International Organization for Medical Physics (IOP), 2023 [online]. Retrieved from: https://www.iomp.org/iomp-news2-flash-radiotherapy/; retrieved on Jul. 31, 2025, 2 pages.

Girdhani, Swati et al., "Abstract LB-280: Flash: A novel paradigm changing tumor irradiation platform that enhances therapeutic ratio by reducing normal tissue toxicity and activating immune pathways", Cancer Research, 2019; 79(13_Supplement): LB-280 [online]. Retrieved from: https://doi.org/10.1158/1538-7445.AM2019-LB-280; retrieved on Jul. 31, 2025, 4 pages.

Groen, J., "Flash optimisation in clinical IMPT treatment planning", MSC Thesis, Jul. 1, 2020; "How to optimise FLASH in clincal IMPT treatment planning", MSc Literature Study, Apr. 25, 2020. Erasmus University Medical Center, Department of Radiotherapy, Delft University of Technology; 65 pages.

Gu and O'Connor, "Integrated beam orientation and scanning-spot optimization in intensity-modulated proton therapy for brain and unilateral head and neck tumors." Medical Physics. 2018; 45(4): 1338-1350.

Inserm (Newsroom), "Radiotherapy 'flashes' to reduce side effects", Jul. 21, 2014 [press release] [online]. Retrieved from: https://presse.inserm.fr/en/radiotherapy-flashes-to-reduce-side-effects/53998/; retrieved on Jul. 31, 2025, 6 pages.

International Neuropsychiatric Association - INA, "Conventional radiation therapy may not protect healthy brain cells", Oct. 10, 2019 [online]. Retrieved from: https://inawebsite.org/conventional-radiation-therapy-may-not-protect-healthy-brain-cells/; retrieved on Jul. 31, 2025, 2 pages.

International Preliminary Report on Patentability for International Application No. PCT/US2019/042603, dated Jan. 19, 2021, 11 pages.

IntraOp Medical Inc., "IntraOp and Lausanne University Hospital Announce Collaboration in FLASH radiotherapy", News and Events, Jun. 12, 2023 [online]. Retrieved from: https://intraop.com/news-events/lausanne-university-flash-radiotherapy-collaboration, retrieved on Jul. 31, 2025; 3 pages.

Kamperis et al. (2019). A Flash back to radiotherapy's past and then fast forward to the future. J Cancer Prev Curr Res, 10(6):142-144.

Keen, C.E., "Clinical linear accelerator delivers FLASH radiotherapy", Physics World, Apr. 23, 2019 [online]. Retrieved from: https://physicsworld.com/a/clinical-linear-accelerator-delivers-flash-radiotherapy (retrieval date unknown); 4 pages.

Kohno, Ryosuke et al., "Development of continuous line scanning system prototype for proton beam therapy", International Journal of Particle Therapy, Jul. 11, 2017; 3(4):429-438.

Kraan, Aafke Christine, "Range verification methods in particle therapy: underlying physics and Monte Carlo modeling", Frontiers in Oncology, Jul. 2015; 5:150, 27 pages.

Kramer, M. et al. "Treatment planning for heavy-ion radiotherapy: physical beam model and doseoptimization", Physics in Medicine & Biology, 2000; 45(11):3299-3317.

Li, H et al., "Reducing dose uncertainty for spot-scanning proton beam therapy of moving tumors by optimizing the spot delivery sequence", Int J Radiat Oncol Biol Phys, Nov. 1, 2015; 93(3): 547-556. HHS Public Access Author Manuscript, available in PMC Mar. 22, 2016; 17 pages.

Liang, S.Q., et al., "Blocking the epithelial-to-mesenchymal transition pathway abrogates resistance to anti-folate chemotherapy in lung cancer", Cell Death Dis, Jul. 16, 2015;6(7):e1824.

Liang, X. et al., "Using Robust Optimization for Skin Flashing in Intensity Modulated Radiation Therapy for Breast Cancer Treatment: A Feasibility Study", Practical Radiation Oncology, Jan-Feb. 2020, 10:59-69.

Lomax, A. "Intensity modulated proton radiotherapy," Physics in Medicine and Biology. Jan. 1999; 44(1): 185-205.

Lomax, A.J. et al., "Intensity modulated proton therapy: A clinical example," Medical Physics, Mar. 2001, vol. 28, Issue 3, pp. 317-324, https://doi.org/10.1118/1.1350587.

Ma, C-M.C., "Physics and Dosimetric Principles of SRS and SBRT," Mathews J Cancer Sci. 2019; 4(2):22, DOI: https://doi.org/10.30654/MJCS.10022, 19 pages.

Mackeprang, P.H. et al., "Assessing dose rate distributions in VMAT plans", Physics in Medicine & Biology, 2016; 61(8):3208, 16 pages.

Maxim, P. G. et al., "FLASH radiotherapy: Newsflash or flash in the pan?", Medical Physics, Oct. 2019; 46(10):4287-4290.

McGowan, S.E. et al., "Treatment planning optimisation in proton therapy", The British Journal of Radiology, 2013; 86(1021):20120288, 12 pages.

McManus, M. et al., "The challenge of ionisation chamber dosimetry in ultra-short pulsed high dose-rate Very High Energy Electron beams", Scientific Reports, 2020; 10(1):9089, doi:10.1038/s41598-020-65819-y; 11 pages.

Mevion Medical Systems, "Focus on the Future : FLASH Therapy", Press Release, 2023 [online]. Retrieved from Wayback Machine: https://web.archive.org/web/20230329163845/https://www.mevion.com/newsroom/press-releases/focus-future-flash-therapy, retrieved on Mar. 29, 2023; 2 pages.

Misher, C., "Radiation Therapy: Which type is right for me?" OncoLink, Mar. 15, 2024 [online]. Retrieved from: https://www.oncolink.org/cancer-treatment/radiation/introduction-to-radiation-therapy/radiation-therapy-which-type-is-right-for-me, retrieved on Jul. 31, 2025; 2 pages.

Montay-Gruel, P. et al., "Long-term neurocognitive benefits of FLASH radiotherapy driven by reduced reactive oxygen species", PNAS, May 28, 2019; 116(22):10943-10951, with Correction, Oct. 13, 2020; 117(41):25946-25947, and Supplementary Information, 7 pages.

Morel, P. et al., "Spot weight adaptation for moving target in spot scanning proton therapy", Frontiers in Oncology, May 2, 20158; 5:119, doi: 10.3389/fonc.2015.0019; 7 pages.

Newhauser, W.D. & Zhang, R. "The physics of proton therapy", Physics in Medicine & Biology, 2015; 60(8):R155-R209.

Nill, S. et al., "Inverse planning of intensity modulated proton therapy", Zeitschrift für Medizinische Physik, 2004; 14(1):35-40.

Office Action and Search Report for Chinese Application No. 201880061494.0 mailed Sep. 2, 2022 with English translation, 10 pages.

Office Action for Chinese Application No. 201880061494.0 mailed Feb. 3, 2023, with English translation, 10 pages.

Office Action for Chinese Application No. 201880061494.0 mailed Jul. 20, 2023, with English translation, 12 pages.

Oraiqat, I. et al., "An ionizing radiation acoustic imaging (iRAI) technique for real-time dosimetric measurements for FLASH radiotherapy", Medical Physics., Oct. 2020; 47(10):5090-5101.

Paganetti, H., "Proton beam therapy", Chapter 1. Bristol: IOP Publishing, Jan. 2017; DOI: https://doi.org/10.1088/978-0-7503-1370-4 [online]. Retrieved from: https://iopscience.iop.org/book/mono/978-0-7503-1370-4/chapter/bk978-0-7503-1370-4ch1; retrieved on Jul. 30, 2025; 25 pages.

Petersson, Kristoffer, "Dosimetry of ultra-high dose rate irradiation for studies on the biological effect induced in normal brain and GBM", Radiotherapy and Oncology, Feb. 16, 2016;118: S84, Abstract 172; 1 page.

Pugachev, A. and Xing, L., "Pseudo beam's-eye-view as applied to beam orientation selection in intensity-modulated radiation therapy," Int. J. Radiation Oncology Biol. Phys., Dec. 1, 2001; 51(5):1361-1370.

(56)     References Cited

OTHER PUBLICATIONS

Pugachev, A. et al., "Role of beam orientation optimization in intensity-modulated radiation therapy," Int. J. Radiation Oncology Biol. Phys., Jun. 1, 2001, vol. 50, No. 2, pp. 551-560; available online May 10, 2001, DOI: https://doi.org/10.1016/S0360-3016(01)01502-4.

Rama, N. et al., "Improved tumor control through T-cell infiltration modulated by ultra-high dose rate proton FLASH using a clinical pencil beam scanning proton system", International Journal of Radiation Oncology, Biology, Physics, 2019; vol. 105, No. 1S, Abstract 1107, pages S164-S165.

RaySearch Laboratories, "Leading the way in cancer treatment, Annual Report 2013," RaySearch Laboratories, Stockholm, Sweden, Apr. 2014 [online]. Retrieved from: https://www.raysearchlabs.com/siteassets/about-overview/media-center/wp-re-ev-n-pdfs/brochures/raysearch-ar-2013-eng.pdf (retrieval date unknown); 94 pages.

Sun, Y., et al., "Signaling pathway of MAPK/ERK in cell proliferation, differentiation, migration, senescence and apoptosis", J Recept Signal Transduct Res, 2015;35(6):600-4.

Symonds, P. & Jones, G.D.D., "Flash radiotherapy: the next technological advance in radiation therapy?" Clinical Oncology, 2019; 31(7):405-406.

Trofimov, A.& Bortfeld, T. "Optimization of beam parameters and treatment planning for intensity modulated proton therapy", Technology in Cancer Research & Treatment, Oct. 2003; 2(5):437-444.

Van De Water et al., "Towards FLASH proton therapy: the impact of treatment planning and machine characteristics on achievable dose rates", Acta Oncologica. 2019; 58(10):1463-1469.

Venkatesulu, B.P. et al., "Ultra-high dose rate (35 Gy/sec) radiation does not spare the normal tissue in cardiac and splenic models of lymphopenia and gastrointestinal syndrome", Scientific Reports, 2019; 9:17180, doi: 10.1038/s41598-019-53562-y; 9 pages.

Vozenin et al. "The advantage of FLASH radiotherapy confirmed in mini-pig and cat- cancer patients" Clinical Cancer Research. 2019;25(1):35-42.

Vozenin, M-C. et al., "Biological benefits of ultra-high dose rate FLASH radiotherapy: sleeping beauty awoken", Clinical Oncology, 2019; 31(7):407-415. HHS Public Access Author Manuscript, available in PMC Nov. 12, 2019; 20 pages.

Weber, D.C. et al., "Radiation therapy planning with photons and protons for early and advanced breast cancer: an overview", Radial Oncol. Jul. 2, 20060; 1:22, doi: 10.1186/1748-717X-1-22, 27 pages.

Widesott, L. et al., "Intensity-Modulated Proton Therapy Versus Helical Tomotherapy in Nasopharynx Cancer: Planning Comparison and NTCP Evaluation," Int. J. Radiation Oncology Biol. Phys., Oct. 1, 2008, vol. 72, No. 2, pp. 589-596; available online Sep. 13, 2008, DOI: https://doi.org/10.1016/j.ijrobp.2008.05.065.

Wilson, J. et al., "Ultra-High Dose Rate (FLASH) Radiotherapy: Silver Bullet or Fool's Gold?" Frontiers in Oncology, Jan. 17, 2020; 9:1563 [online]. Retrieved from: https://www.ncbi.nlm.nih.gov/pmc/articles/PMC6979639; retrieved on Oct. 23, 2020, 12 pages.

Zakaria, A.M. et al., "Ultra-High Dose-Rate, Pulsed (FLASH) Radiotherapy with Carbon Ions: Generation of Early, Transient, Highly Oxygenated Conditions in the Tumor Environment", Radiat Res. Dec. 1, 2020;194(6):587-593. doi: 10.1667/RADE-19-00015. 1. HHS Public Access Author Manuscript, available in PMC Feb. 3, 2021; 15 pages.

Zhang, X. et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., Jun. 1, 2010, vol. 77, No. 2, pp. 357-366.

* cited by examiner

<u>100</u>

106

REMOVABLE STORAGE
<u>108</u>

NON-REMOVABLE
STORAGE <u>120</u>

SYSTEM MEMORY 104

TREATMENT
PLANNING SYSTEM
<u>150</u>

CENTRAL
PROCESSING UNIT
<u>120</u>

OUTPUT DEVICE(S)
<u>126</u>
(e.g., DISPLAY
DEVICE)

INPUT DEVICE(S) <u>124</u>

COMMUNICATION
CONNECTION(S) <u>122</u>

NETWORK

Normal Tissue Toxicity Studies

| TIME POINT | DOSE (Gy) | CONV | FLASH | SP FLASH | SHAM | TOTAL | |
|---|---|---|---|---|---|---|---|
| 1 HOUR | 0 | | | | 6 | 6 | |
| | 15 | 10 | 10 | 10 | | 30 | |
| | | | | | | 36 | |
| 24 HOUR | 0 | | | | 6 | 6 | |
| | 15 | 10 | 10 | 10 | | 30 | |
| | | | | | | 36 | |
| 8 WEEK | 0 | | | | 6 | 6 | |
| | 15 | 10 | 10 | 10 | | 30 | |
| | | | | | | 36 | |
| 16 WEEK | 0 | | | | 6 | 6 | |
| | 15 | 20 | 20 | 20 | | 60 | |
| | | | | | | 66 | |
| 24 WEEK | 0 | | | | 6 | 6 | |
| | 15 | 20 | 20 | 20 | | 60 | |
| | | | | | | 66 | |
| 36 WEEK | 0 | | | | 12 | 12 | |
| | 15 | 20 | 20 | 20 | | 60 | |
| | 17.5 | 20 | 20 | | | 40 | |
| | 20 | 20 | 20 | | | 40 | |
| | | | | | | 152 | |
| | | 130 | 130 | 90 | 42 | 392 | GRAND TOTAL |

392 age and sex matched mice

6 Cohorts: Sacrifice 1hr-36 wks after lung irradiation

4 Groups in each cohort
- Shame: no radiation
- Conventional: 1Gy/s
- FLASH: 40Gy/s beam on
- Split-FLASH: 4Gy/0.1 sec, pulsed delivery

*FIG. 5*

Lung Function

Penh (Typical Values):

| Baseline: | 100% |
|---|---|
| Mildly Challenged: | 250% |
| Moderately Challenged: | 400% |
| Severely Challenged: | 1000% |

Survival Study
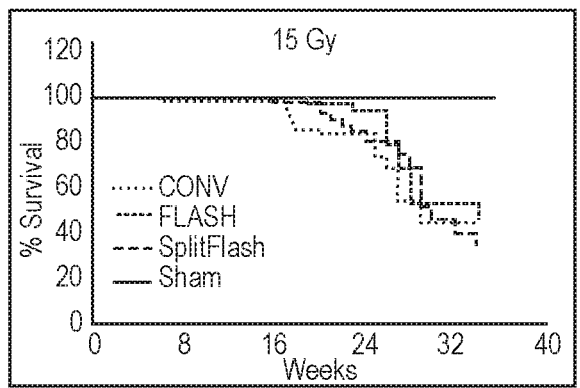
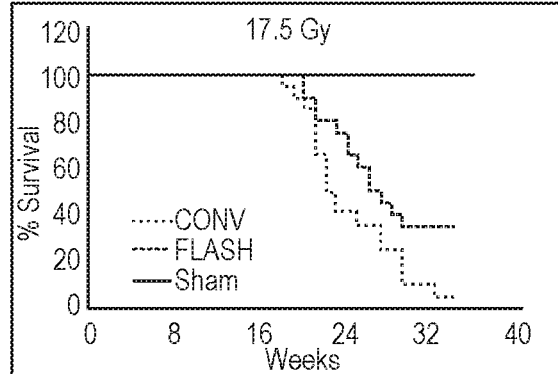
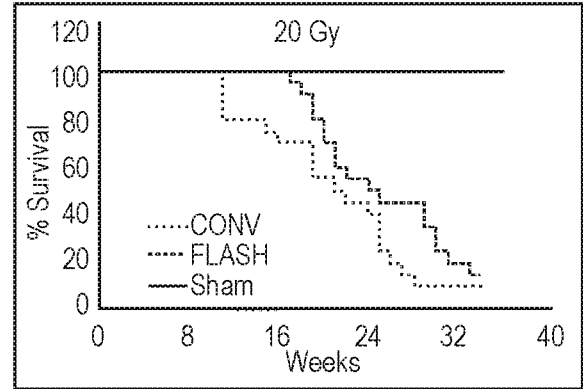
Median Survival
| Dose | Flash | Conv |
|---|---|---|
| 20 Gy | 24 wks | 21 wks |
| 17.5 Gy | 26 wks | 22 wks |
*FIG. 7*

Survival Study

Dermatitis

| ActualTreatement | Severe | Extreme |
|---|---|---|
| SplitFLASH | 1 | 1 |
| FLASH | 4 | 2 |
| Conventional | 7 | 10 |

*FIG 12A*
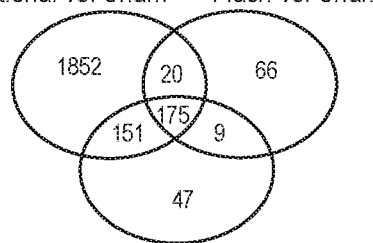
24 Hours
Conventional vs. Sham    Flash vs. Sham
Split Flash vs. Sham    25045
*FIG 12B*
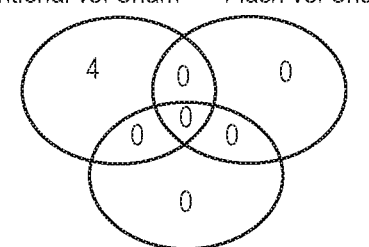
8 Weeks
Conventional vs. Sham    Flash vs. Sham
Split Flash vs. Sham    27361
*FIG 12C*
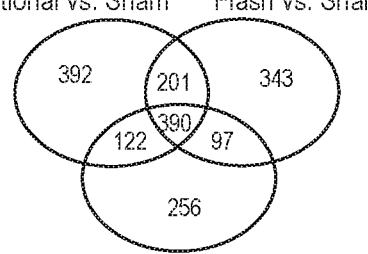
16 Weeks
Conventional vs. Sham    Flash vs. Sham
Split Flash vs. Sham    25564
*FIG 12D*
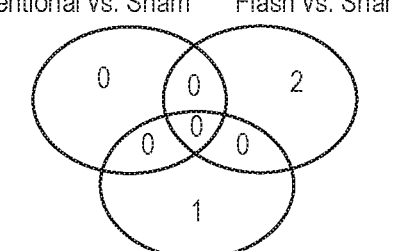
24 Weeks
Conventional vs. Sham    Flash vs. Sham
Split Flash vs. Sham    27362
*FIG. 12*

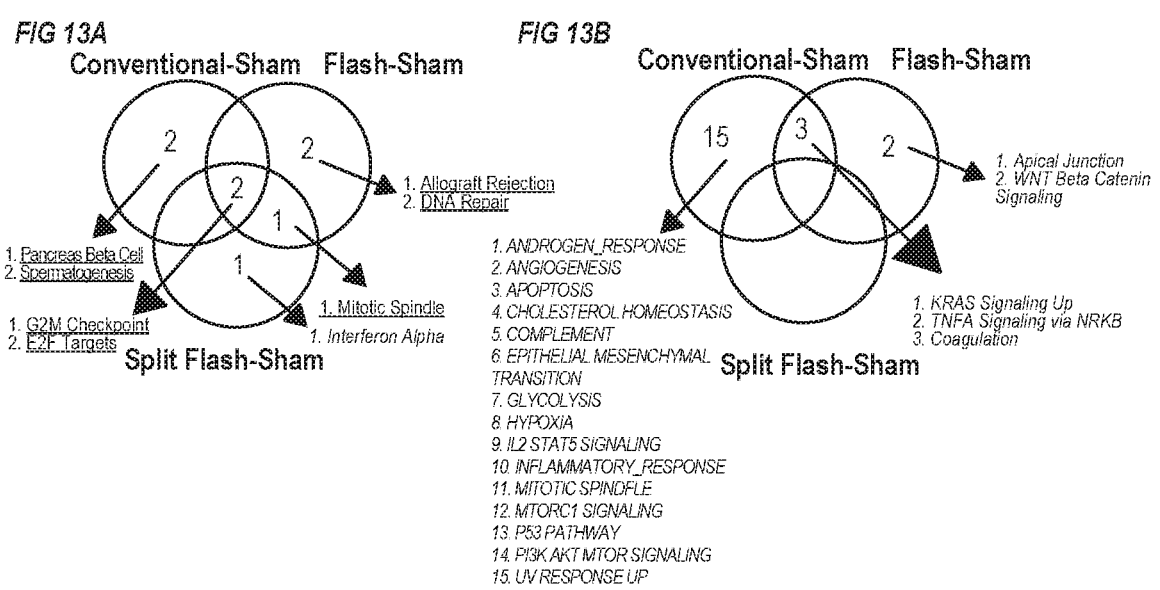
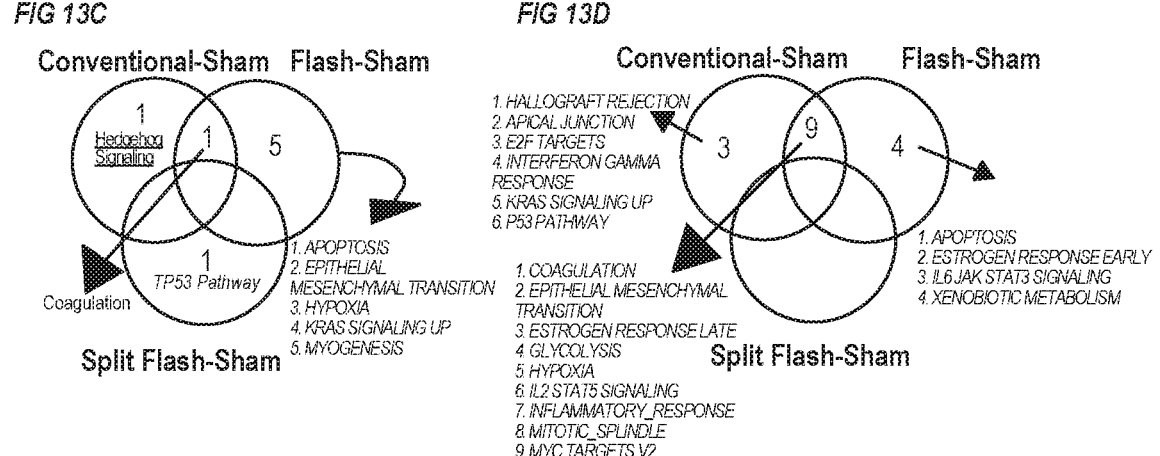
FIG. 13

*FIG 14A*
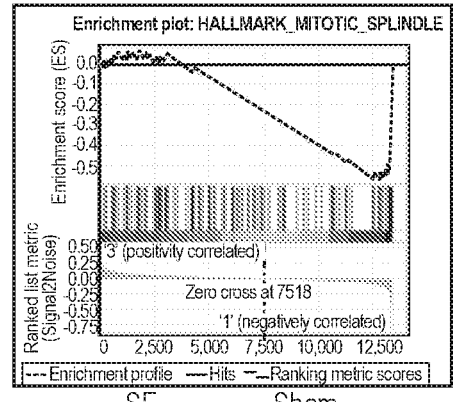
SF     Sham
*FIG 14B*
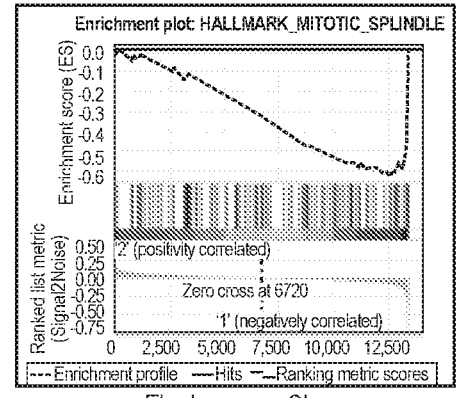
Flash     Sham
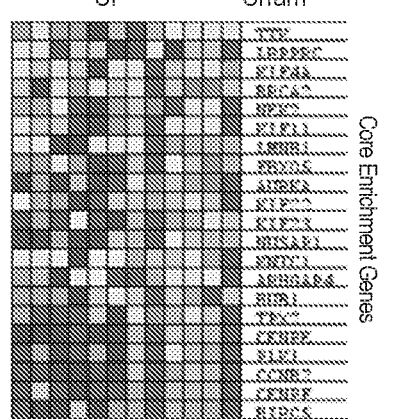
*FIG 14C*
Flash-Core-Genes     Split Flash-Core-Genes
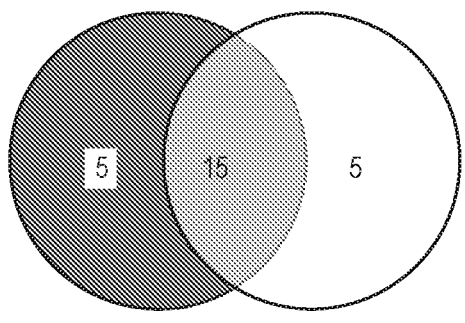
*FIG 14D*
| Flash | Overlap | Split-Flash | |
|---|---|---|---|
| ARHGAP10 | AURKA | ARHGAP4 | |
| CDC42EP1 | BIRC5 | BRCA2 | |
| CDC42EP2 | BUB1 | KNTC1 | |
| FSCN1 | CCNB2 | LRPPRC | |
| KIF15 | CENPE | NEK2 | |
| | CENPF | | |
| | FBXO5 | | |
| | KIF11 | | |
| | KIF22 | | |
| | KIF23 | | |
| | KIF4A | | |
| | LMNB1 | | |
| | NUSAP1 | | |
| | PLK1 | | |
| | TPX2 | | |
*FIG. 14*

FIG 15A
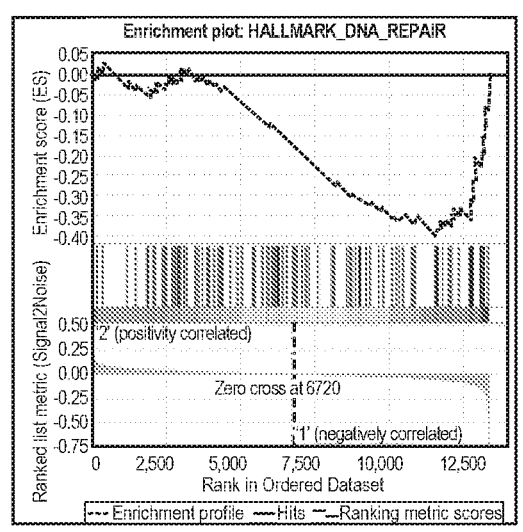
FIG 15B
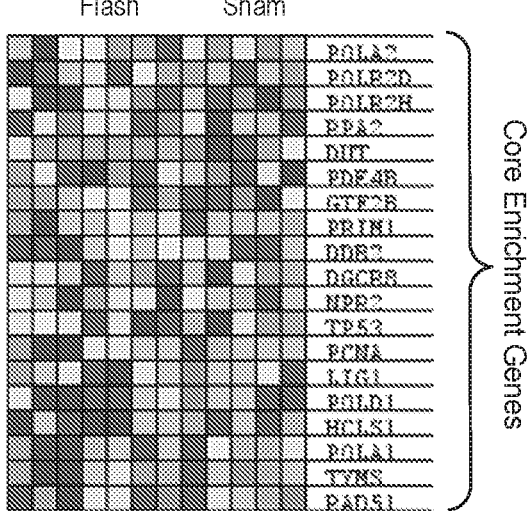
| GeneSet | DNA Repair |
|---|---|
| Norm. Enrichment Score | -1.50316 |
| Nominal p-value | 0.041016 |
| FDR q-value | 0.208294 |
FIG. 15

FIG 16A
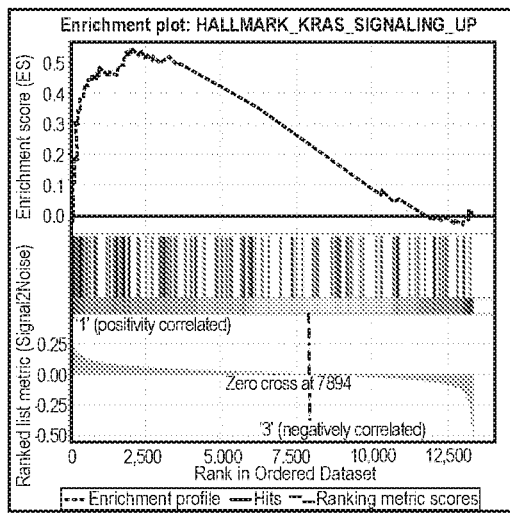
Flash 8 Weeks
| NES | 1.351275 |
|---|---|
| Nominal p-value | 0.043561 |
| FDR q-value | 0.228315 |
FIG 16B
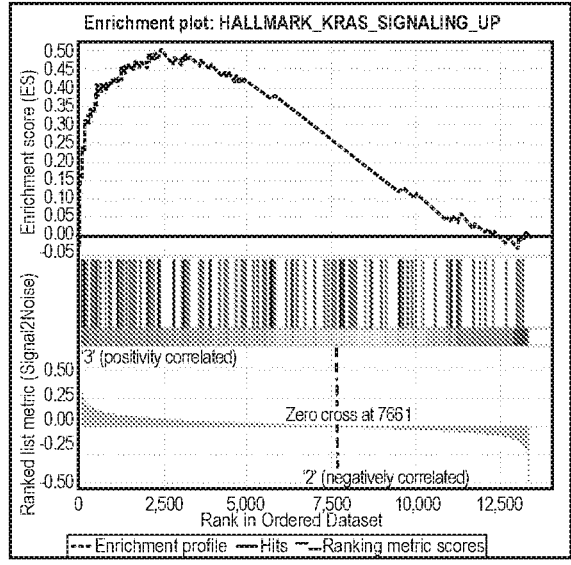
Flash 16 Weeks
| NES | 1.438819 |
|---|---|
| Nominal p-value | 0.0233463 |
| FDR q-value | 0.22549081 |
FIG 16C
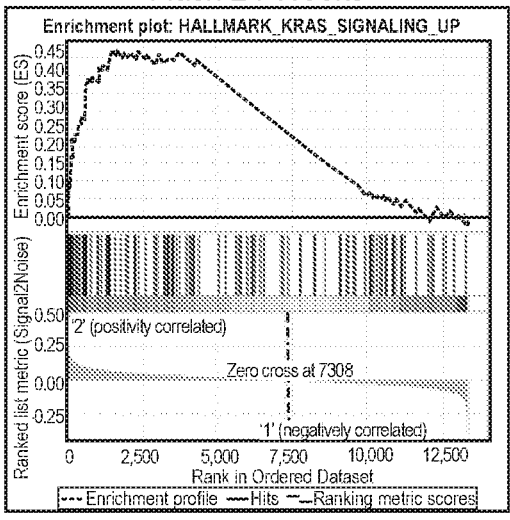
Flash 24 Weeks
| NES | 1.438819 |
|---|---|
| Nominal p-value | 0.0233463 |
| FDR q-value | 0.22549081 |
FIG. 16

*FIG 17A*
Conventional 24 Weeks
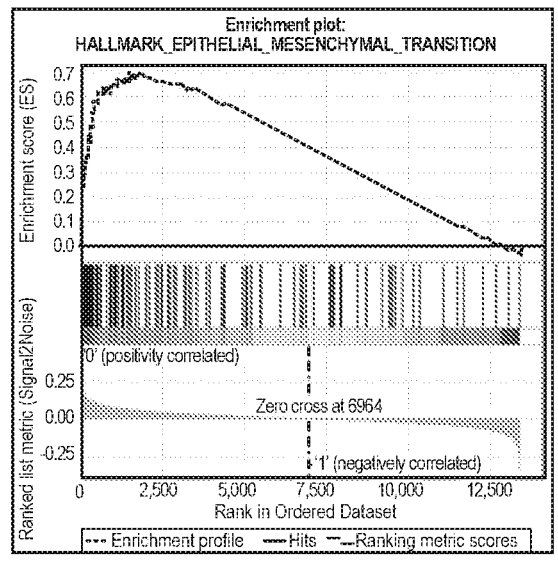
| GeneSet | EMT |
|---|---|
| NES | 1.715518 |
| Nominal p-value | 0.001 |
| FDR q-value | 0.066558 |
*FIG 17B*
Flash 24 Weeks
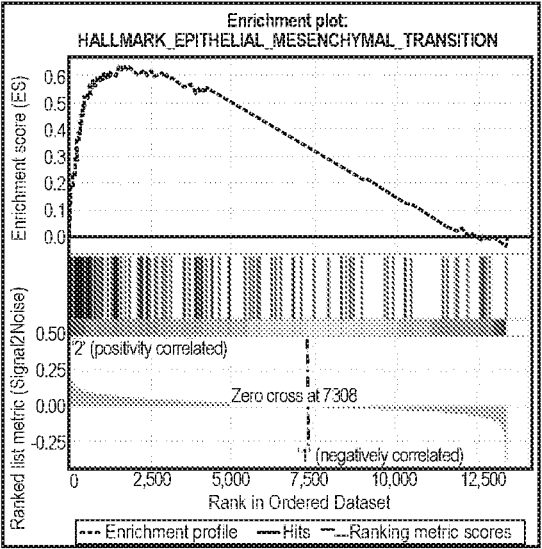
| GeneSet | EMT |
|---|---|
| NES | 1.743082 |
| Nominal p-value | 0.002066 |
| FDR q-value | 0.017006 |
*FIG 17C*
Conv EMT Core    Flash EMT Core
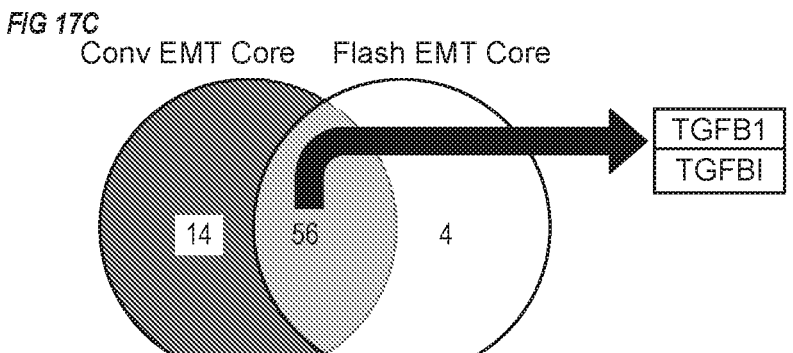
TGFB1
TGFBI
*FIG. 17*

24 Hr IPA data

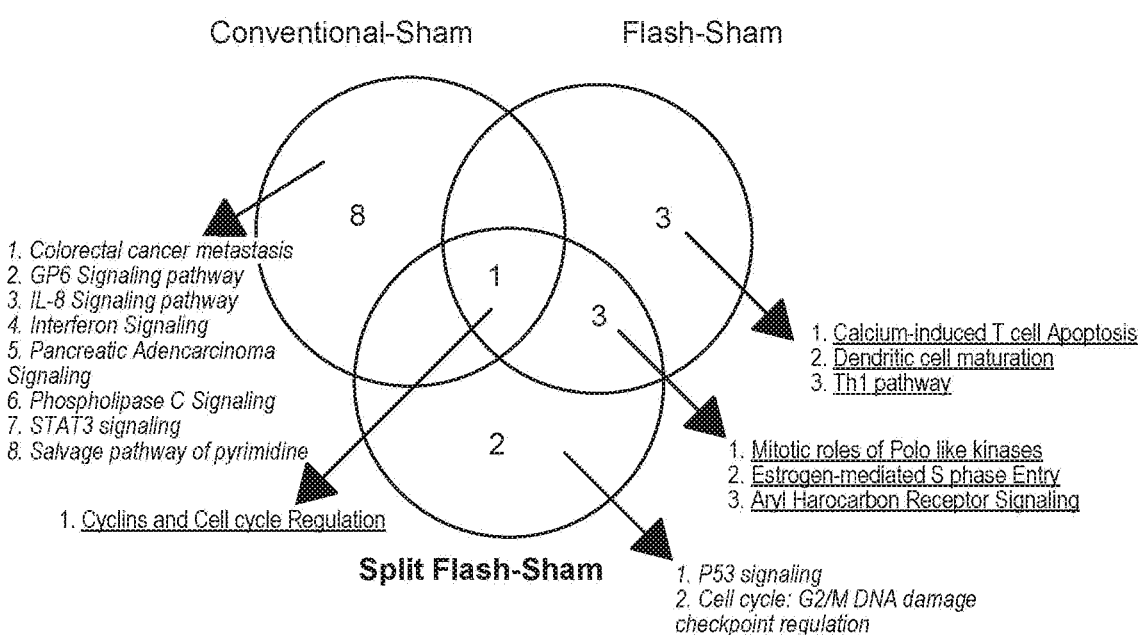

Conventional-Sham                    Flash-Sham 8          3

1          3

2

Split Flash-Sham

1. *Colorectal cancer metastasis*
2. *GP6 Signaling pathway*
3. *IL-8 Signaling pathway*
4. *Interferon Signaling*
5. *Pancreatic Adencarcinoma Signaling*
6. *Phospholipase C Signaling*
7. *STAT3 signaling*
8. *Salvage pathway of pyrimidine*

1. Cyclins and Cell cycle Regulation

1. Calcium-induced T cell Apoptosis
2. Dendritic cell maturation
3. Th1 pathway

1. Mitotic roles of Polo like kinases
2. Estrogen-mediated S phase Entry
3. Aryl Harocarbon Receptor Signaling 1. *P53 signaling*
2. *Cell cycle: G2/M DNA damage checkpoint regulation*

*FIG. 18*

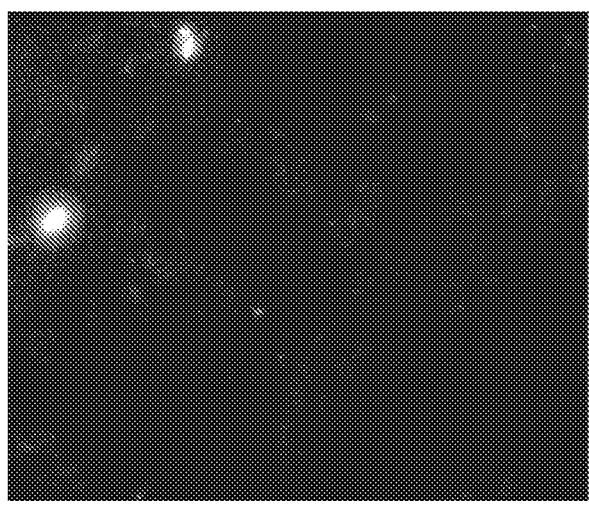
FIG. 23A
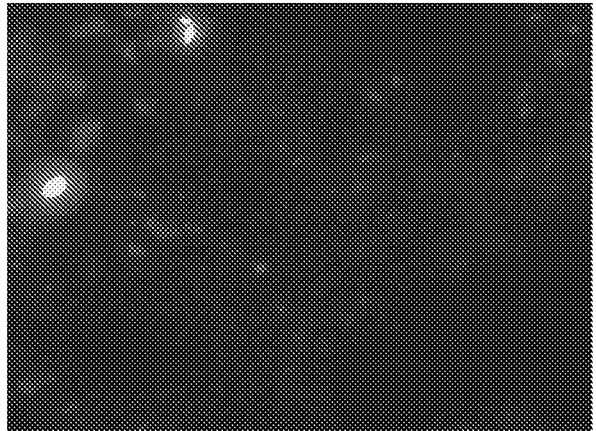
FIG. 23B
FIG. 23

Figure : Plot showing the results of the TUNEL counting statistics per animal as a function of treatment

METHODS OF USE OF ULTRA-HIGH DOSE RATE RADIATION AND THERAPEUTIC AGENT

CROSS-REFERENCE TO RELATED APPLICATIONS

The present application is a Continuation of U.S. application Ser. No. 17/486,169, filed on Sep. 27, 2021, entitled "METHODS OF USE OF ULTRA-HIGH DOSE RATE RADIATION AND THERAPEUTIC AGENT." (now U.S. Pat. No. 11,771,920, issued Oct. 3, 2023), which is a continuation of U.S. application Ser. No. 16/041,636, filed Jul. 20, 2018 entitled "METHODS OF USE OF ULTRA-HIGH DOSE RATE RADIATION AND THERAPEUTIC AGENT," (now U.S. Pat. No. 11,173,325, issued Nov. 16, 2021), which is a non-provisional application of and claims the benefit and priority under 35 U.S.C. 119 (e) of U.S. Provisional Application No. 62/535,682, filed Jul. 21, 2017 entitled "RADIATION TREATMENT PLANNING AND APPLICATION IN COMBINATION WITH IMMUNO-THERAPY," and U.S. Provisional Application No. 62/700,783, filed Jul. 19, 2018 entitled "METHODS OF USE OF ULTRA-HIGH DOSE RATE RADIATION AND THERA-PEUTIC AGENTS," the entire content of which are incorporated herein by reference for all purposes.

BACKGROUND OF THE INVENTION

Radiation therapy is a key therapeutic modality for patients with cancer. Radiation can be delivered to the tumor with submillimeter precision while mostly sparing normal tissue, ultimately leading to tumor cell killing. However, the tumor cell's ability to escape the cell killing effects of radiation and/or to develop resistance mechanisms can counteract the tumor cell killing action of radiotherapy, potentially limiting the therapeutic effect of radiotherapy to treat cancer. Furthermore, the potential for normal tissue toxicity can impact the therapeutic window of radiation therapy as a treatment paradigm.

Radiation-induced tumor cell death leads to release of tumor antigens from lysed cells, increased MHC-1 expression on antigen presenting cells, and enhanced diversity of the intratumoral T-cell population. These factors and others are key to initiate activation of the body's own immune systems to eradicate cancer cells. Immune modulators are being explored to activate the body's own immune system, but are known to have limitations as monotherapy (e.g., response rate in patients). The response rate of immune modulators when used as monotherapy is in the range of 20-30% of the targeted patient population. Combination approaches such as using two immune modulators or an immune modulator with a targeted anti-cancer drug have limitations due to systemic normal tissue toxicity.

BRIEF SUMMARY OF THE INVENTION

Treating tumors with ultra-high-dose-rate radiation (e.g., FLASH RT) may improve the therapeutic window by decreasing the normal tissue side effects while maintaining tumor toxicity when compared to conventional RT. It is possible to decrease normal tissue side effects by either increasing the dose rate or by limiting the time normal tissue is exposed to radiation. It is possible to enforce the increased therapeutic window by means of multiple discrete fields or continuous rotational delivery of ionizing radiation.

Reduced side effects to the normal tissue could also allow for dose escalation in the tumor leading to enhanced tumor kill and control.

Conventional radiation induces stromal, immunological, and vascular changes that can counteract the tumor cell killing effects of radiation. It was unexpectedly discovered that FLASH irradiation impacts the microenvironment differently, ultimately leading to a more immune competent tumor environment. As a result, FLASH irradiation combined with a therapeutic agent can increase tumor cell killing while minimizing normal tissue toxicity. In some embodiments, the therapeutic agent is an immune modulator, a senolytic agent, a radiosentizer, and/or a nanoparticle.

Several mechanisms are employed to foster immune suppression in the tumor microenvironment including, but not limited to, the recruitment of regulatory T cells (Tregs), tumor-associated macrophages (TAMs) and myeloid-derived suppressor cells (MDSCs). In addition, anti-inflammatory elements, such as transforming (or tumor) growth factor beta (TGF-beta) and IL-10, inhibit cytolytic activity of cytotoxic T-cells (CTLs). TAMs and MDSCs modify the metabolic milieu of the tumor microenvironment by producing arginase and nitric oxide that depletes L-arginine, an essential nutrient for T-cell function. Further, abnormal tumor angiogenesis results in hypoxia, which initiates the recruitment of immune-suppressive myeloid cells. Suppressive myeloid cells generate reactive oxygen and nitrogen species that modify receptors on cytotoxic lymphocytes (CTLs) both in the lymphoid organs and in the tumor itself, impacting the ability of CTL's to home to tumors and kill tumor cells.

When treating a patient with FLASH RT, the immune-suppressive microenvironment does not have an opportunity to fully develop. With a severely limited immune-suppressive tumor microenvironment, there will be an increased immunological response to the dying tumor cells that ultimately will improve tumor cell killing.

Other factors that play roles in the immune-suppressive microenvironment include tumor-infiltrating macrophages that can develop an M1-M2 phenotype switch that can impact the killing of tumor cells. These effects are not seen with FLASH RT. Another benefit of FLASH RT is that it spares circulating immune cells from radiation induced toxicity, leading to improved immune-related tumor cell killing effects.

The methods described herein provide the dual benefits of anti-tumor efficacy and normal tissue protection when combining a therapeutic agent with FLASH radiation to treat cancer patients. Methods described herein can be used to treat local and metastatic cancers by FLASH radiation therapy to deliver a highly conformal dose to the tumor, and an immune modulator. This combination therapy has the potential to improve both the efficacy of radiation therapy both locally and systemically, and the efficacy of the immune modulators while minimizing toxicity to normal tissues.

Protons deposit their energy most densely at the end of their path, a mechanism that has been used to its advantage in cancer radiotherapy (Jones et al., British Journal of Radiotherapy 2006, Jakel Radiat Protection Dosimetry 2009). The characteristic plot of absorbed dose as a function of penetration depth has a maximum at the location just before the particle stops, enabling the therapeutic targeting of tumors at specific depths. In contrast, dose deposition for electron/photon beam radiotherapy is maximal near the entrance surface of the tissue, e.g., the skin, followed by an exponential decrease with tissue depth. Due to these physical characteristics, proton therapy allows for high dose deposition in deep seated tumors.

The inventors surprisingly determined that an unexpected advantage of proton energy deposition is not only dependent on the absolute dose delivered to the target, but also on the dose rate (speed) used to deliver the dose. It was unexpected to observe a proton dose rate-dependent biology, e.g. different biological pathways are activated when protons are delivered at different dose rates. The dose rate dependent characteristics of proton deposition have major implications for cancer therapy and the development of novel treatment options, including dose rate dependent combination therapies.

Thus, in one aspect, provided herein is a method for treating a tumor in a subject with cancer comprising administering an effective amount of ultra-high-dose-rate (FLASH) radiation and a therapeutic agent to the tumor. In some embodiments, the method reduces damage to normal tissue when compared to administering conventional radiation (e.g., a dose of 0.5 Gy/sec) to the tumor. In some embodiments, dermatitis, lung fibrosis or lymphocyte apoptosis are decreased compare to administering conventional radiation.

In some embodiments, the FLASH radiation is administered at a dose rate equal to or greater than 40 Gy/sec, or the dose is administered in 1 second or less. In some embodiments, the FLASH radiation is administered in a single pulse or in multiple pulses. In some embodiments, the FLASH radiation comprises or consists of protons. In some embodiments, the FLASH radiation does not comprise electrons.

In some embodiments, the therapeutic agent is an immune modulator, a radiosentizer, or a nanoparticle.

In some embodiments, the therapeutic agent is a mitotic spindle inhibitor, a DNA damage repair and response inhibitor, a MAPK pathway inhibitor, an epithelial to mesenchymal (EMT) inhibitor, an activator of T helper type 1 (TH1) lymphocytes, an activator of the PTEN pathway, and inhibitor of the TGF-beta pathway, an activator of the type-1 interferon signaling pathway, an activator of dendritic cell maturation, an inhibitor of CD47/SIRP-alpha, or an inhibitor of the Aryl Hydrocarbon Receptor (ahR).

In some embodiments, the mitotic spindle inhibitor is selected from a CDK4/6 inhibitor, an AURKA inhibitor, a TPX2-AURKA complex inhibitor, or a taxane.

In some embodiments, the DNA damage repair and response inhibitor is selected from a PARP inhibitor, a RAD51 inhibitor, or an inhibitor of a DNA damage response kinase selected from CHCK1, ATM, or ATR.

In some embodiments, the MAPK pathway inhibitor is an inhibitor of EGFR, MEK, BRAF, or ERK.

In some embodiments, the EMT inhibitor is a TGFβ-pathway inhibitor selected from a compound, small molecule, antibodies or fragments thereof that bind TGF-beta.

In some embodiments, the activator of T helper type 1 (TH1) lymphocytes is a cytokine, a toll-like receptor agonist, a STAT3 modulator, compounds derived from inactivated bacteria/or parasites or their derivatives that trigger interferon gamma or IL-12 production, included but not limited to *Listeria monocytogenes, Leishmania major* and *Toxoplasma gondii, Mycobacterium tuberculosis*, staphylococcus enteroxin B and unmethylated CpG nucleotides that activate a Th1 response in the body, or gene therapy systems including bacterial or virus based gene expression systems that lead to production of IL2, IL-12 and IFN-gamma when injected at the tumor site.

In some embodiments, the activator of the PTEN pathway is selected from an mTOR inhibitor selected from rapamycin, temsirolimus, everolimus, sirolimus or AP-2357; Ublituximab, Rituximab, Sunitinib, (Induces PTEN), Trastuzumab and Pertuzumab (Increases PTEN through Src inhibition), Resistin (p38 MAPK modulator, increases PTEN), Simvastatin (NF0-kB inhibitor), Lovastatin and Rosiglitazone (PPAR-gamma modulators), NVP-AEW541 (IGF-1R modulator that increases PTEN), and PP1 Herbimycin (Src inhibitors) (see, e.g., Boosani et al Expert Opin Ther Pat. 2013 May; 23(5):569-580.)

In some embodiments, the inhibitor of the TGF-beta pathway is selected from a compound, small molecule, antibodies or fragments thereof that bind TGF-beta.

In some embodiments, the activator of the type-1 interferon signaling pathway is a STING agonist, an Toll-like receptor (TLR) agonist, or a MAVS agonist.

In some embodiments, the activator of dendritic cell maturation is a synthetic peptide vaccine. In some embodiments, the inhibitor of CD47/SIRP-alpha is selected from an antibody or fragment thereof, or a small molecule compound that inhibits the CD47/DSIRP-alpha interaction.

In some embodiments, the nanoparticle has a high effective atomic number, or comprises gold or gadolinium.

In some embodiments, the ahR inhibitor is SR1, CH-223191, UM729, or Galangin.

In some aspects, provided herein is a method for treating a tumor in a subject with cancer comprising administering ionizing FLASH radiation and an immune modulator to the tumor, wherein the immune modulator is selected from the group consisting of an inhibitor to an inhibitory checkpoint molecule, an activator of a stimulatory checkpoint molecule, a chemokine inhibitor, an inhibitor of macrophage migration inhibitory factor (MIF), a growth factor, a cytokine, an interleukin, an interferon, an antibody that binds to an immune system cell, a cellular immune modulator, a vaccine, an oncolytic virus, and any combination thereof. Administration of the immune modulator was unexpectedly found to increase the anti-tumor response when combined with FLASH radiation.

In some embodiments, the inhibitor to the inhibitory checkpoint molecule is a small molecule drug, or an antibody or a fragment thereof that specifically binds to the inhibitory checkpoint molecule and inhibits its activity, wherein the inhibitory checkpoint molecule is selected from the group consisting of PD-1, PD-L1, PD-L2, CTLA-4, BTLA, A2aR, B7-H2, B7-H3, B7-H4, B7-H6, CD47, CD48, CD160, CD244 (2B4), CHKE CHK2, CGEN-15049, ILT-2, ILT-4, LAG-3, VISTA, gp49B, PIR-B, TIGIT, TIM1, TIM2, TIM3, TIM4, and KIR, and ligands thereof. In some embodiments, the activator of the stimulatory checkpoint molecule is a small molecule drug, polypeptide-based activator, or polynucleotide-based activator that specifically binds to the stimulatory checkpoint molecule and increases its activity, wherein the stimulatory checkpoint molecule is selected from the group consisting of B7-1 (CD80), B7-2 (CD86), 4-IBB (CD137), OX40 (CD134), HVEM, inducible costimulator (ICOS), glucocorticoid-induced tumor necrosis factor receptor (GITR), CD27, CD28, CD40, and ligands thereof. In some instances, the chemokine inhibitor is a small molecule drug, or antibody or fragment thereof that specifically binds to the chemokine (or its receptor) and inhibits chemokine activity. In some embodiments, the chemokine is selected from the group consisting of CCL2, CCL3, CCL4, CCL5, CCL7, CCL8, CCL11, CCL12, CCL13, CCL14, CCL15, CCL16, CCL17, CCL18, CCL19, CCL20, CCL21, CCL22, CCL23, CCL24, CCL5, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL5, and CXCL16. In some embodiments, the chemokine inhibitor binds to a chemokine receptor selected from the group consisting of CCR1, CCR2, CCR3, CCR, 4, CCR5, CCR6, CCR7, CCR8, CCR9, CCR10, CXCR1, CXCR2, CXCR3, CXCR4, CXCR5, CXCR6, and CXCR7. In some cases, the inhibitor of MIF is a small molecule drug, or antibody or fragment thereof that specifically binds to MIF and inhibits MIF activity.

In some aspects, provided herein is a method for treating a tumor in a subject with cancer comprising administering FLASH radiation and an immune modulator to the tumor. In some embodiments, the immune modulator can be an antibody or antibody fragment targeting CD44, MMP9, ALDH1A1, Vimentin, hyaluronan, beta-catenin, MFG-E8, CD68, TGFβ, a TGFβ-pathway related biomarker, or any combination thereof.

Also provided herein are improved methods for treating a tumor that include administering an immune modulator and FLASH radiation to the subject with cancer. This combination therapy can elicit an increased anti-cancer response compared to immune modulator monotherapy or conventional radiation monotherapy.

Immunomodulatory agents to be combined with FLASH include, but are not limited to checkpoint inhibitors, co-stimulators, broad immune modulators modulating the adenosine pathway or STING (Stimulating Interferon Genes) pathways, bispecific antibodies targeting both immune cell antigens and cancer antigens, and cell therapy approaches (e.g., chimeric antigen receptor (CAR) therapies).

In some embodiments, the positive effects of FLASH RT are enhanced by combining FLASH RT with delivery of an immunotherapy agent as a concomitant, adjuvant, or neo-adjuvant procedure. Thus, the immunomodulating properties of FLASH RT described herein can be enhanced and provide further benefit to a patient or subject in need of treatment when used in combination with immunomodulatory agents. The combination of FLASH RT and immunotherapy can be incorporated into radiation treatment planning as well as in the treatments themselves.

The combination of FLASH RT and an immune modulator described herein can also be combined with personalized medicine treatment protocols. Thus, in some embodiments, the methods include detecting the expresssion of one or more biomarkers in the subject. In some embodiments, the one or more biomarkers are selected from CD44, MMP9, ALDH1A1, Vimentin, hyaluronan, beta-catenin, MFG-E8, CD68, TGFβ, a TGFβ-pathway related biomarker, or any combination thereof. In some embodiments, methods include radiomics information such as tumor phenotype. In some embodiments, methods include functional imaging information, including but not limited to PET, SPECT, and fMRI.

In some aspects, provided herein is a method for treating a tumor in a subject with cancer comprising administering ionizing FLASH radiation and an immune modulator to the tumor. The method comprises (a) determining an expression level of one or more biomarkers in a tumor sample from the subject, wherein the one or more biomarkers are selected from the group consisting of an immune cell marker(s), tumor cell marker(s), circulating marker(s), and any combination thereof; (b) comparing the expression level of the one or more biomarkers to an expression level of the one or more biomarkers in a normal tissue sample; and (c) administering to the tumor in the subject a treatment comprising ionizing FLASH radiation and an immune modulator if the expression level of the one or more biomarkers in the tumor sample is modified compared to the expression level in the normal tissue sample. The biomarker can be CD44, MMP9, ALDH1A1, Vimentin, hyaluronan, beta-catenin, MFG-E8, CD68, TGFβ, a TGFβ-pathway related biomarker, or any combination thereof.

In certain aspects, provided herein is a method of identifying a subject with cancer as a candidate for treatment comprising ionizing FLASH radiation and an immune modulator. The method includes: (a) determining an expression level of one or more biomarkers in a tumor sample from the subject, wherein the one or more biomarkers are selected from the group consisting of an immune cell marker(s), tumor cell marker(s), circulating marker(s), imaging marker(s), and any combination thereof; (b) comparing the expression level of the one or more biomarkers to an expression level of the one or more biomarkers in a normal tissue sample; and (c) classifying the subject as a candidate for treatment comprising ionizing FLASH radiation and the immune modulator if the expression level of the one or more biomarkers in the tumor sample is modified compared to the expression level in the normal tissue sample. The biomarker can be CD44, MMP9, ALDH1A1, Vimentin, hyaluronan, beta-catenin, MFG-E8, CD68, TGFβ, a TGFβ-pathway related biomarker, or any combination thereof.

In other aspects, provided herein is a method of selecting a treatment for a subject with cancer. The method comprises: (a) determining an expression level of one or more biomarkers in a tumor sample from the subject, wherein the one or more biomarkers are selected from the group consisting of an immune cell marker(s), tumor cell marker(s), circulating marker(s), and any combination thereof; (b) comparing the expression level of the one or more biomarkers to an expression level of the one or more biomarkers in a normal tissue sample; and (c) selecting a treatment comprising ionizing FLASH radiation and an immune modulator if the expression level of the one or more biomarkers in the tumor sample is modified compared to the expression level in the normal tissue sample. The biomarker can be CD44, MMP9, ALDH1A1, Vimentin, hyaluronan, beta-catenin, MFG-E8, CD68, TGFβ, a TGFβ-pathway related biomarker, or any combination thereof.

In some embodiments, the subject is administered ionizing FLASH radiation and/or combination therapy comprising ionizing FLASH radiation and an immune modulator if the expression level of CD44 is increased and/or the expression level of MFG-E8 is decreased relative to the expression level in a normal or control sample. In some embodiments, the amount of ionizing FLASH radiation and/or the amount of an immune modulator administered to the subject is increased if the expression level of CD44 is increased and/or the expression level of MFG-E8 is decreased relative to the expression level in a normal or control sample. On the other hand, the amount of ionizing FLASH radiation and/or the amount of an immune modulator administered to the subject can be decreased if the expression level of CD44 is decreased and/or the expression level of MFG-E8 is increased relative to the expression level in a normal or control tissue sample.

In some embodiments, the subject is administered ionizing FLASH radiation and/or combination therapy comprising ionizing FLASH radiation and an immune modulator if the expression level of CD68 is increased relative to the expression level in a normal or control tissue sample. In some embodiments, the amount of ionizing FLASH radiation and/or the amount of an immune modulator administered to the subject is increased if the expression level of CD68 is increased relative to the expression level in a normal or control tissue sample. On the other hand, the amount of ionizing FLASH radiation and/or the amount of an immune modulator administered to the subject can be decreased if the expression level of CD68 is decreased relative to the expression level in a normal or control tissue sample.

In some aspects, provided herein is use of FLASH radiation and a therapeutic agent for treating a tumor in a subject. In some embodiments, the use comprises a combination of ionizing FLASH radiation and a therapeutic agent selected from an immune modulator described herein, a senolytic agent, and/or a radiosensitizer described herein.

In another aspect, the disclosure provides a therapeutic agent for use in a method of treating a tumor in a subject with cancer, characterized in that the method comprises administering FLASH radiation and the therapeutic agent to the tumor. In some embodiments, a therapeutic agent in combination with ultra-high dose rate (FLASH) radiation for use in the treatment of cancer or a tumor is provided.

In another aspect, provided herein is a therapeutic agent for use in a method of treating a tumor in a subject with cancer, characterized in that the method comprises:

(a) determining an expression level of one or more biomarkers in a tumor sample from the subject, wherein the one or more biomarkers are selected from the group consisting of an immune cell marker(s), tumor cell marker(s), circulating marker(s), and any combination thereof;

(b) comparing the expression level of the one or more biomarkers to an expression level of the one or more biomarkers in a normal tissue sample; and (c) administering to the tumor in the subject a treatment comprising ionizing FLASH radiation and the therapeutic agent if the expression level of the one or more biomarkers in the tumor sample is modified compared to the expression level in the normal tissue sample.

In another aspect, a method for treating a tumor in a subject is described, the method comprising:

i) detecting expression of a biomarker described herein in the tumor microenvironment or a tumor sample from a subject, and ii) administering an effective amount of FLASH radiation and a therapeutic agent to the subject, thereby treating the tumor.

In some embodiments, the expression level of the biomarker(s) described herein is compared to the expression level detected in a normal or control (e.g., non-tumor) tissue in the subject.

In another aspect, a method for treating a tumor in a subject is described, the method comprising:

i) contacting a tumor sample from the subject with an antibody that binds to a biomarker described herein;

ii) detecting modified expression of the biomarker in the tumor sample, and iii) administering an effective amount of FLASH radiation and a therapeutic agent to the subject, thereby treating the tumor.

In some embodiments, the modified biomarker expression comprises increased and/or decreased expression levels of the biomarker. In some embodiments, the biomarker is selected from the group consisting of CD44, MMP9, ALDH1A1, Vimentin, hyaluronan, beta-catenin, MFG-E8 and CD68. In some embodiments, the expression level of biomarker CD68 is increased in the tumor environment or in the tumor sample. In some embodiments, the expression level of biomarker CD44 is increased in the tumor environment or in the tumor sample. In some embodiments, the expression level of biomarker CD44 is increased and the expression level of MFG-E8 is decreased in the tumor environment or in the tumor sample.

In some embodiments, the method further comprises detecting the expression level of a biomarker described herein in a normal tissue sample. In some embodiments, the expression level of the biomarker is detected with an antibody that binds to the biomarker(s).

In another aspect, a radiation treatment system is provided. In some embodiments, the radiation treatment system provides radiation treatment for a subject or patient in need thereof. In some embodiments, the radiation treatment system further comprises an immunotherapy system that treats the patient with a therapeutic agent in coordination with the radiation treatment. In some embodiments, the radiation treatment is FLASH RT.

In another aspect, a radiation treatment planning system is described, the radiation treatment planning system operable for generating a radiation treatment plan that also includes immunotherapy performed in coordination with the radiation treatment. In some embodiments, the radiation treatment is FLASH RT.

In another aspect, a non-transitory computer-readable storage medium having computer-executable instructions for causing a computing system to perform a method of ultra-high-dose-rate (FLASH) radiation treatment planning for treating a tumor in combination with a therapeutic agent is described.

In some embodiments, provided is a non-transitory computer-readable storage medium having computer-executable instructions for causing a computing system to perform a method of ultra-high-dose-rate (FLASH) radiation treatment planning for treating a tumor in combination with a therapeutic agent, the method comprising:

accessing values of parameters from memory of the computing system, wherein the parameters comprise directions of beams to be directed into sub-volumes in a target and beam energies for the beams;

accessing information that specifies limits for the radiation treatment plan, wherein the limits are based on a dose threshold and comprise a limit on irradiation time for each sub-volume outside the target;

wherein the information that specifies limits comprises information about treatment of the tumor with a therapeutic agent; and adjusting the values of the parameters that affect a calculated amount of dose to be delivered by the beams until differences between respective total values for the sub-volumes satisfy a threshold value.

In some embodiments, each portion of the beams that is in the target is represented as a respective set of longitudinal beam regions, and wherein the method further comprises:

for each of the beam regions, computing an amount of dose to be delivered by a beam region and assigning a value to the beam region corresponding to the amount; and for each of the sub-volumes, computing a total value for the sub-volume by adding together the value for each beam region of each beam that reaches the sub-volume; wherein said adjusting further comprises adjusting the parameters that affect the calculated amounts of dose to be delivered by the beam regions until differences between respective total values for the sub-volumes satisfy the threshold value.

In some embodiments, said adjusting further comprises: determining whether a beam overlaps any other beams outside the target; and weighting beam intensities for beam segments of the beam according to how many other beams are overlapped by the beam outside the target.

In some embodiments, the method further comprises performing a dose calculation for an outside-the-target sub-volume, wherein said performing a dose calculation comprises:

accessing a value for a dose calculation factor for the outside-the-target sub-volume, wherein the value for the dose calculation factor is determined according to how many beams reach the outside-the-target sub-volume;

calculating a dose for the outside-the-target sub-volume; and applying the value of the dose calculation factor to the dose calculated for the outside-the-target sub-volume.

In some embodiments, the dose calculation factor reduces the dose calculated for the outside-the-target sub-volume if only one beam reaches the outside-target sub-volume.

In some embodiments, the limits are selected from the group consisting of: a limit on irradiation time for each sub-volume in the target; a limit on dose rate for each sub-volume in the target; and a limit on dose rate for each sub-volume outside the target.

In some embodiments, the dose threshold is further dependent on tissue type. In some embodiments, the beams comprise a type of beam selected from the group consisting of: proton; electron; photon; atom nuclei; and ion.

In another aspect, a computer-implemented method of radiation treatment planning for a treating a tumor in combination with a therapeutic agent is described.

In some embodiments, the computer-implemented method of radiation treatment planning comprises:

determining a prescribed dose of ultra-high-dose-rate (FLASH) radiation to be delivered into and across a tumor target, wherein the prescribed dose is determined based on a response of the tumor to a therapeutic agent;

accessing values of parameters comprising a number of beams in a plurality of beams to be directed into sub-volumes in the target, directions of the plurality of beams, and beam energies for the plurality of beams, wherein each of the beams comprises a plurality of beam segments;

identifying any overlapping beams in the plurality of beams that have respective beam paths that overlap outside the target;

for each beam in the plurality of beams, determining a maximum beam energy for the beam and determining beam energies for the beam segments of the beam as a percentage of the maximum beam energy for the beam; and for each overlapping beam of the overlapping beams that overlap outside the target, reducing the beam intensities for the beam segments of the overlapping beam by a dose calculation factor, wherein the beam intensities for the beam segments for the plurality of beams are determined such that a cumulative dose delivered to the target satisfies the prescribed dose.

In some embodiments, the method comprises:

representing each of the beams in the target as a respective set of longitudinal beam regions, wherein each beam region in the set has a value corresponding to a calculated amount of dose to be delivered by the beam region;

for each sub-volume in the target, adding together the value for each beam region of each beam that reaches the sub-volume to determine a total value for the sub-volume, to produce respective total values for the sub-volumes in the target; and adjusting the values of the parameters that affect the calculated amounts of dose to be delivered by the beam regions until differences between the total values for the sub-volumes satisfy a threshold value.

In some embodiments, the method comprises:

accessing a value for the dose calculation factor for an outside-the-target sub-volume, wherein the value for the dose calculation factor is determined according to how many beams reach the outside-the-target sub-volume;

calculating a dose for the outside-the-target sub-volume; and applying the value of the dose calculation factor to the dose calculated for the outside-the-target sub-volume, wherein the dose calculation factor reduces the dose calculated for the outside-the-target sub-volume if only one beam reaches the outside-target sub-volume.

In some embodiments, the method comprises using a dose threshold to specify limits for the radiation treatment plan, wherein the limits are selected from the group consisting of: a limit on irradiation time for each sub-volume in the target; a limit on irradiation time for each sub-volume outside the target; a limit on dose rate for each sub-volume in the target; and a limit on dose rate for each sub-volume outside the target.

In some embodiments, the dose threshold is dependent on a plurality of biological factors including but not limited to tissue type and/or immunological profile.

In some embodiments, the beams comprise a type of beam selected from the group consisting of: proton; electron; photon; atom nuclei; and ion.

In another aspect, use of ultra-high-dose-rate (FLASH) radiation in combination with a therapeutic agent for treating cancer or a tumor in a subject in need thereof is provided.

In another aspect, ultra-high-dose-rate (FLASH) radiation in combination with a therapeutic agent for use in the treatment of cancer or a tumor is provided.

In any of the above aspects and embodiments, the therapeutic agent can be an immune modulator, a senolytic agent, a radiosensitizer, and/or a nanoparticle.

BRIEF DESCRIPTION OF THE DRAWINGS

FIG. 5 shows the experimental design for normal tissue toxicty studies in control mice (sham treated) and mice treated with conventional, FLASH, and split-Flash radiation.

FIG. 7 shows an improved median survival for FLASH over Conventional radiation treament groups: 20.0 Gy: 14% increase; 17.5 Gy: 18% increase.

FIG. 12A-D shows Venn Diagrams of Differentially Expressed genes at each time point. A) DE genes at 24 hours B) 8 weeks C) 16 weeks D) 24 weeks with adjusted p-values less than or greater than 0.05.)

FIG. 13A-D shows overlap of GSEA Hallmark pathways between three treatment groups. A) GSEA at 24 hours B) 8 weeks C) 16 weeks D) 24 weeks with FDR-q values<0.25 and adjusted p-values<0.05. Underlined text denotes downregulated while italicized text denotes upregulated pathways relative to Sham treated samples.

FIG. 14A-D shows Hallmark Mitotic Spindle enrichment plots and core enrichment genes for Split Flash-Sham and Flash-Sham GSEA analysis. Enrichment plot for Hallmark Mitotic Spindle for A) Split-Flash and B) Flash treatment group gene expression heatmaps of core enrichment genes for Split-Flash and Flash. C) Overlap between split flash and flash treatment groups. D) List of genes from FIG. 14C, BOLD genes are key players in Mitotic Spindle assembly.

FIGS. 15A and 15B show Flash Specific DNA repair signature and core enrichment genes: A) (Top left): Enrichment plot of DNA repair signature (Bottom Left): Enrichment statistics for DNA Repair Signature. B) Gene expression heatmap of core Enrichment genes in the Hallmark DNA repair signature.

FIG. 16A-C shows Flash Specific KRAS Signaling Up 8 Weeks-24 Weeks: (Top): Enrichment plot of KRAS signaling Up signature & enrichment statistics for A) 8 Weeks B) 16 weeks and C) 24 weeks for flash treated mice.

FIG. 17A-C shows EMT Signature and Core enrichment gene analysis: EMT Enrichment plot and statistics for 24 week A) Conventional B) Flash treated cells. C) Overlap of Core enrichment genes between Conventional and Flash, highlighting TGF Beta genes. See Supplemental Table 1 for details core enrichment genes and full list of overlap.

FIG. 18 shows a pie chart representing various canonical pathways found to be regulated by different radiation regimens at 24 Hr. Analysis was done on filtered list of genes having p value of <0.05. samples. Pathways presented her and listed in Table 1 are have p value<0.05, FDR<0.1 and Z score of >1.5. Underlined text denotes downregulated while italicized text denotes upregulated pathways relative to Sham treated samples.

FIGS. 23A and B shows (A) the original FITC image, and (B) the segmented TUNEL positive cells. The Fiji distribution of ImageJ was used to quantify the number of TUNEL positive cells in each field of view. A gaussian blur was first applied to the image, and then thresholding was used to segment the objects.

DEFINITIONS

Figure 1:
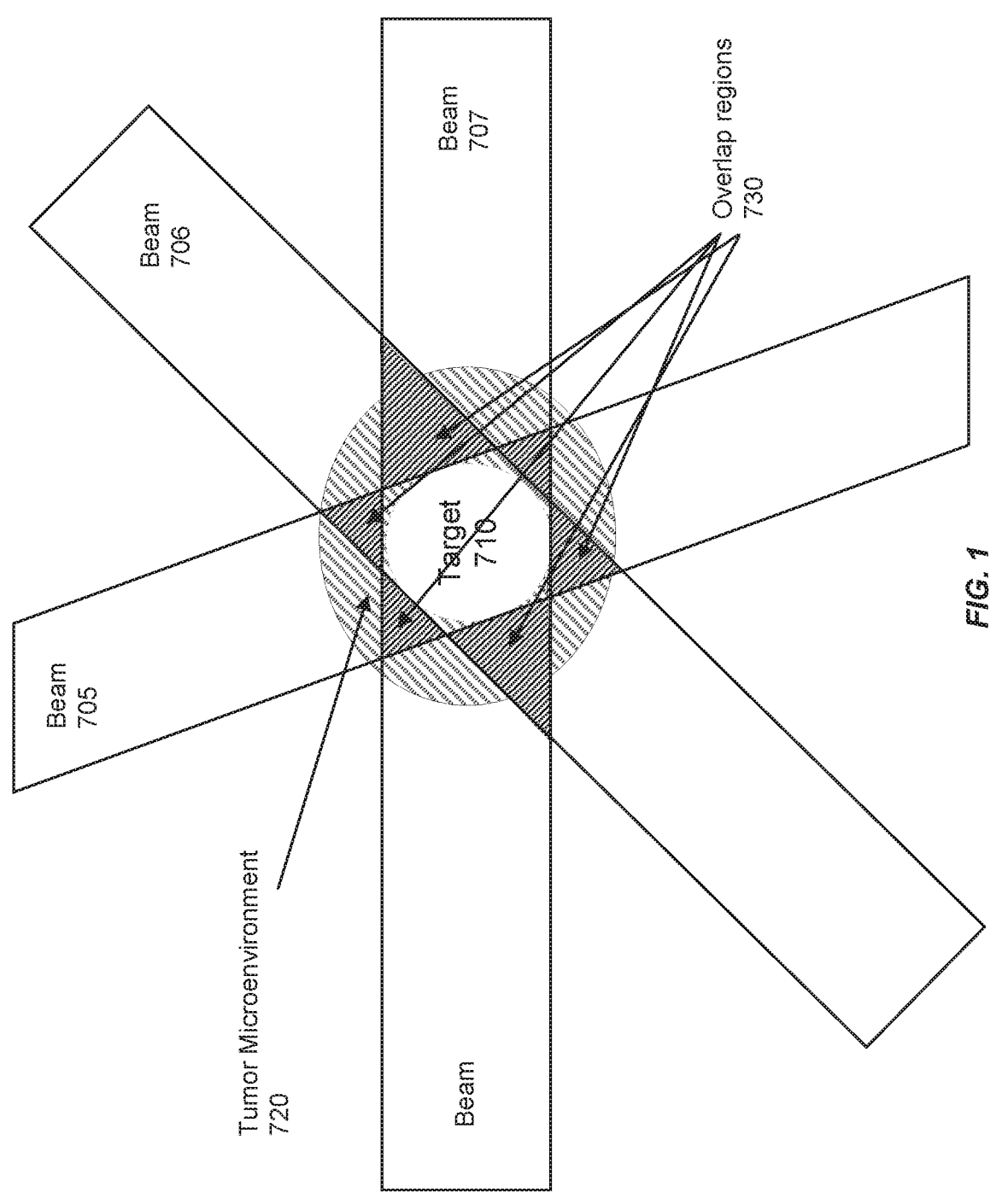
FIG. 1. illustrates a cross-sectional view of a sample beam geometry in an embodiment described herein.

The term "treating" refers to administering a treatment to a tumor or the subject diagnosed with a tumor. The treatment can be administered in an amount or therapeutic dose that is sufficient or effective to kill tumor cells (i.e., a therapeutically effective amount), slow the growth of the tumor, reduce the size of the tumor, or eliminate the tumor from the subject entirely. Examples of treatments include ionizing radiation, such as FLASH radiation therapy, a therapeutic agent, an immune modulator agent, a senolytic agent, a radiosensitizer, a nanoparticle or combinations thereof. The term also includes selecting a treatment or treatment plan, and providing treatment options to a healthcare provider or the subject.

The term "therapeutic agent" refers to an agent such as a small molecule drug or biologic drug that can be used to treat a tumor, and can include an immune modulator, a senolytic agent, a radiosensitizer, or a nanoparticle. The therapeutic agent can be an agent approved by a regulatory agency for treating tumors or cancer, undergoing clinical trials prior to regulatory approval, or that is under investigation for treating tumors or cancer. The therapeutic agent can be combined with radiation therapy, such as conventional or FLASH radiation therapy, to treat a tumor. In some embodiments, the therapeutic agent is combined with FLASH radiation therapy to treat a tumor.

The term "ionizing radiation" refers to radiation comprising particles having enough kinetic energy to discharge an electron from an atom or molecule, thereby producing an ion. The term includes both directly ionizing radiation, such as that caused by atomic particles such as alpha particles (helium nuclei), beta particles (electrons), and protons, and indirectly ionizing radiation, such as photons, including gamma rays and x-rays. Examples of ionizing radiation used in radiation therapy include high energy x-rays, electron beams, ion beams, and proton beams.

The terms "FLASH", "FLASH radiation" or "FLASH Radiation Therapy (FLASH RT)" refers to ultra-high-dose-rate radiation that is administered to a subject or patient as therapy. In some embodiments, the dose can be administered to a subject or patient in need of treatment in one to many short pulses at an ultra-high dose rate. In some embodiments, the entire radiaiton dose is delivered in a total "beam-on" time of no more than one second.

FLASH refers to a mode of administering ionizing radiation at a dose rate which ensures all normal tissue irradiation occurs in 1 second or less for the delivery of the entire dose prescription. For example, a dose prescription of 20 Gray (Gy) would require a dose rate of at least 20 Gy per second for a single irradiation direction, 10 Gy per second for 2 irradiation directions, 5 Gy per second for 4 irradiation directions, and so on. The number of fields can reduce the dose rate to satisfy the FLASH irradiation conditions so long as either the fields do not overlap or overlapping fields are delivered in the 1 second or less time frame.

Pulsed FLASH is mode of administering ionizing radiation at a dose rate which results in the total active delivery time to normal tissue for a prescribed dose of ionizing radiation in 1 second or less, with allowance for repeated irradiation of the same normal tissue volume in a single treatment session or fraction. For example a 20 Gy prescription would be delivered in 1 second or less of active irradiation time, but could be divided in to 5 pulses of 4 Gy spaced 1 second apart, each pulse delivered in 0.2 seconds, or 20 Gy per second per pulse. Another example is 10 pulses of 2 Gy having a duration of 0.1 seconds spaced 2 seconds apart, or 20 Gy per second per pulse. Pulsed FLASH allows for freedom of duty cycle selection for the delivery so long as the total active delivery time of 1 second or less is enforced for a single treatment session. Pulse separation can vary from an interval between pulses of less than a second to several minutes.

Fractionated FLASH is the delivery of FLASH or pulsed FLASH ionizing radiation over the course of a longer time interval. This time interval can be hours to days following the established clinical protocols for fractionated radiation therapy, with the actual treatment delivery being either FLASH or pulsed FLASH.

The term "conventional radiation therapy" or "conventional irradiation" of tissues refers to a dose of 0.5 Gy per second, for example 20 Gy in 40 seconds, 17.5 Gy in 35 seconds, or 15 Gy in 30 seconds (0.5 Gy/sec).

The term "tumor environment" or "tumor micro-environment" refers to the immediate small-scale environment of an organism or part of an organism, especially as a distinct part of a larger environment, for example, the immediate small-scale environment of the tumor. The term includes not only the tumor cells themselves, but associated blood-vessels (including endothelial cells and smooth muscle cells), immune system cells and secreted cytokines, epithelial cells, fibroblasts, connective tissue, and/or extracellular matrix that is associated with or surrounds the tumor. The term also refers to the cellular and extracellular environment in which the tumor is located.

The term "standard of care" or "standard radiation treatment protocol" in radiation therapy generally refers to the ionizing radiation dose and administration interval that is generally accepted in the medical field as appropriate treatment for a given tumor, based on the tumor type, size, tissue location, and various other biological parameters. The standard of care or standard treatment protocol varies and is dependent on several factors. For example, for radiation therapy of lung cancer, the standard of care includes multiple fractions (e.g., approximately 30 fractions of low dose radiation, or approximately 60 Gy over 6 weeks) or a smaller number of fractions (e.g., 1-5 fractions) of biologically active doses (e.g., 54 GY in 3 fractions for peripheral tumors, or 48-60 Gy in 4-8 fractions for central tumors) administered to the tumor.

The term "similar dose of ionizing radiation" refers to a dose of ionizing radiation that is identical to, nearly the same, or substantially the same as the effective dose administered to a tumor in another subject, or administered to a tumor in the same subject undergoing an existing course of treatment. The term encompasses the normal and expected variation in ionizing radiation doses delivered by a medical technician skilled in the art of administering ionizing radiation to a tumor in a subject. For example, the term encompasses variation in the effective dose administered to a tumor of less than 10%, less than 5%, or less than 1%. The subject can be a human or non-human animal, such as a companion animal (e.g., cat, dog) or farm animal (e.g., cow, horse, etc.).

The term "expression level" refers to the amount or level and/or the presence or absence of a biomarker described herein.

The term "small molecule drug" refers to an organic compound having a molecular weight of less than about 50 kDa, less than about 10 kDa, less than about 1 kDa, less than about 900 daltons, or less than about 500 daltons. The term includes drugs having desired pharmacological properties, and includes compounds that can be administered orally or by injection.

The term "radiosensitizer" refers to any substance that makes tumor cells easier to kill with radiation therapy. Exemplary radiosensitizers include hypoxia radiosensitizers such as misonidazole, metronidazole, and trans-sodium crocetinate, and DNA damage response inhibitors such as Poly (ADP) ribose polymerase (PARP) inhibitors.

The term "reduced tissue damage" or "reduces damage to normal tissue" refers to a decrease in tissue damage when administering FLASH radiation versus conventional radiation to a subject. The decreased tissue damage can be determined by measuring or quantifying a cellular or tissue response to irradiation, such as but not limited to dermatitis, fibrosis, cell death, or respiratory disorder. In some embodiments, reduced tissue damage refers to a decrease in tissue damage of at least about 10%, 15%, 20%, 25%, 30%, 35%, 40%, 45%, 50% or more in the cellular or tissue response to irradiation when administering FLASH versus conventional radiation to a subject."

The terms "sample," "biological sample," and "tumor sample" refer to bodily fluid, such as but not limited to blood, serum, plasma, or urine, and/or cells or tissues obtained from a subject or patient. In some embodiments, the sample is a formalin-fixed and paraffin embedded tissue or tumor sample. In some embodiments, the sample is a frozen tissue or tumor sample. In some embodiments, the tumor sample can be a biopsy comprising tumor cells from the tumor. In some embodiments, the subject or patient is an animal or mammal. In some embodiments, the subject or patient is a human.

The term "about" refers to variation in measurements of any value described herein, or administered doses described herein, typically encountered by one of ordinary skill in the art. Thus, the term "about" includes variation of plus or minus 0.1, 0.5, 1.0, 2.0, 3.0, 4.0, 5.0, 6.0, 7.0, 8.0, 9.0, or 10.0 percent of any value described herein. Any value described herein is considered modified by the term "about" whether or not the term "about" is used. Any numerical range described herein includes the endpoints and all values in between the endpoints. For example, the range of about 1 to 10 includes about 1.0, about 1.1, about 1.2, . . . about 9.8, about 9.9, or about 10.0.

DETAILED DESCRIPTION OF THE INVENTION

The methods described herein provide the advantages of anti-tumor efficacy and normal tissue protection when combining a therapeutic agent such as an immune modulator, senolytic agent, radiation sensitizer or nanoparticle with FLASH radiation to treat cancer patients. The methods described herein provide the unexpected result that FLASH radiation in combination with a therapeutic agent (e.g., immune modulator therapy) can increase the anti-tumor response compared to treatment with FLASH radiation therapy or the therapeutic agent therapy alone (mono-therapy). The increase in the anti-tumor response can enhance or increase the inhibition of tumor growth that is provided by either monotherapy alone. Methods described herein can be used to treat local and metastatic cancers by administering FLASH radiation therapy to deliver a highly conformal dose to the tumor, and a therapeutic agent. The combination therapy described herein can improve both the efficacy of FLASH radiation therapy (locally and systemi-cally) and the efficacy of the therapeutic agent therapy. In some embodiments, the therapeutic agent or immune modu-lator also enhances the anti-cancer response when adminis-tered in combination with FLASH radiation, compared to administration of either the therapeutic agent alone or FLASH radiation monotherapy. The methods described herein can also increase the anti-tumor response compared to treatment with conventional radiation therapy or thera-peutic agent therapy alone (monotherapy).

In one aspect, a method for treating a tumor in a subject with cancer comprising administering FLASH RT and an immune modulator to the tumor is provided. The immune modulator can be selected from the group consisting of an inhibitor to an inhibitory checkpoint molecule, an activator of a stimulatory checkpoint molecule, a chemokine inhibi-tor, an inhibitor of macrophage migration inhibitory factor (MIF), a growth factor, a cytokine, an interleukin, an inter-feron, an antibody that binds to an immune system cell, such as a bispecific antibody that binds to T-cells and a tumor antigen, a cellular immune modulator such as a CAR-T cell, a vaccine, an oncolytic virus, and any combination thereof. In some embodiments, the inhibitor to the inhibitory check-point molecule is a small molecule drug, or an antibody or a fragment thereof that specifically binds to the inhibitory checkpoint molecule and inhibits its activity, wherein the inhibitory checkpoint molecule is selected from the group consisting of PD-1, PD-L1, PD-L2, CTLA-4, BTLA, A2aR, B7-H2, B7-H3, B7-H4, B7-H6, CD47, CD48, CD160, CD244 (2B4), CHK1, CHK2, CGEN-15049, ILT-2, ILT-4, LAG-3, VISTA, gp49B, PIR-B, TIGIT, TIM1, TIM2, TIM3, TIM4, and KIR, and ligands thereof. In other embodiments, the activator of the stimulatory checkpoint molecule is a small molecule drug, polypeptide-based activator, or poly-nucleotide-based activator that specifically binds to the stimulatory checkpoint molecule and increases its activity, wherein the stimulatory checkpoint molecule is selected from the group consisting of B7-1 (CD80), B7-2 (CD86), 4-IBB (CD137), OX-40 (CD134), HVEM, inducible costimulator (ICOS), glucocorticoid-induced tumor necrosis factor receptor (GITR), CD27, CD28, CD40, and ligands thereof. In certain embodiments, the chemokine inhibitor is a small molecule drug, or antibody or fragment thereof that specifically binds to the chemokine (or its receptor) and inhibits chemokine activity. In some embodiments, the chemokine is selected from the group consisting of CCL2, CCL3, CCL4, CCL5, CCL7, CCL8, CCL11, CCL12, CCL13, CCL14, CCL15, CCL16, CCL17, CCL18, CCL19, CCL20, CCL21, CCL22, CCL23, CCL24, CCL5, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL5, and CXCL16. In some embodiments, the chemokine inhibitor binds to a chemokine receptor selected from the group consisting of CCR1, CCR2, CCR3, CCR, 4, CCR5, CCR6, CCR7, CCR8, CCR9, CCR10, CXCR1, CXCR2, CXCR3, CXCR4, CXCR5, CXCR6, and CXCR7. The inhibitor of MIF can be a small molecule drug, or antibody or fragment thereof that specifically binds to MIF and inhibits MIF activity. Other inhibitors of macrophage migration can also be used. In some embodiments, the immune modulator is an inhibitor of indoleamine 2,3-dioxygenase (IDO).

The method can further include: (a) detecting an expres-sion level of one or more biomarkers in a tumor sample from the subject, wherein the one or more biomarkers, e.g., 1, 2, 3, 4, 5 or more biomarkers are selected from the group consisting of an immune cell marker(s), tumor cell marker (s), circulating marker(s), and any combination thereof; (b) comparing the expression level of the one or more biomark-ers, e.g., 1, 2, 3, 4, 5 or more biomarkers to the expression level of the one or more biomarkers, e.g., 1, 2, 3, 4, 5 or more biomarkers in a normal tissue sample; and (c) treating the tumor with FLASH RT and an immune modulator if the expression level of the one or more biomarkers, e.g., 1, 2, 3, 4, 5 or more biomarkers is modified compared to the expression level in the normal tissue sample. In some instances, the expression level of the one or more biomark-ers, e.g., 1, 2, 3, 4, 5 or more biomarkers is modified if the expression level of at least one of the biomarkers is increased, or the expression level of at least one of the biomarkers is decreased, or the expression level of at least one of the biomarkers is increased and the expression level of at least one of the biomarkers is decreased compared to the expression level in a normal tissue sample. The expres-sion level of the one or more biomarkers, e.g., 1, 2, 3, 4, 5 or more biomarkers can be ranked or weighted.

In some embodiments, the immune cell biomarker(s) or the tumor cell biomarker(s) or the circulating biomarker(s) is a polynucleotide or a protein. The step of detecting can be performed by using an assay selected from the group con-sisting of immunohistochemistry, ELISA, Western analysis, HPLC, proteomics, PCR, RT-PCR, Northern analysis, and a microarray.

The tumor sample can be a biopsy comprising tumor cells. The normal tissue sample can comprise non-tumor cells from the same tissue type as the tumor.

In another aspect, provided herein is a method of treating a tumor in a subject with cancer comprising: (a) determining an expression level of one or more biomarkers, e.g., 1, 2, 3, 4, 5 or more biomarkers in a tumor sample from the subject, wherein the one or more biomarkers, e.g., 1, 2, 3, 4, 5 or more biomarkers are selected from the group consisting of an immune cell marker(s), tumor cell marker(s), circulating marker(s), and any combination thereof; (b) comparing the expression level of the one or more biomarkers, e.g., 1, 2, 3, 4, 5 or more biomarkers to an expression level of the one or more biomarkers, e.g., 1, 2, 3, 4, 5 or more biomarkers in a normal tissue sample; and (c) administering to the tumor in the subject a treatment comprising FLASH RT and a thera-peutic agent if the expression level of the one or more biomarkers, e.g., 1, 2, 3, 4, 5 or more biomarkers in the tumor sample is modified compared to the expression level in the normal tissue sample.

In some instances, the step of administering FLASH RT comprises contacting the tumor with a radiosensitizer. The FLASH RT can be administered at a higher dose compared to a standard treatment protocol if the expression level of the one or more biomarkers, e.g., 1, 2, 3, 4, 5 or more biomark-ers in the tumor sample is modified compared to the expression level in the normal tissue sample. The FLASH RT can be administered as a hypofractionated radiation treatment if the expression level of the one or more biomarkers, e.g., 1, 2, 3, 4, 5 or more biomarkers in the tumor sample is modified compared to the expression level in the normal tissue sample. In other cases, the FLASH RT is administered as a hyperfractionated radiation treatment if the expression level of the one or more biomarkers, e.g., 1, 2, 3, 4, 5 or more biomarkers in the tumor sample is modified compared to the expression level in the normal tissue sample.

In yet another aspect, provided herein is a method of identifying a subject with cancer as a candidate for treatment comprising FLASH RT and a therapeutic agent. The method comprises (a) determining an expression level of one or more biomarkers, e.g., 1, 2, 3, 4, 5 or more biomarkers in a tumor sample from the subject, wherein the one or more biomarkers are selected from the group consisting of an immune cell marker(s), tumor cell marker(s), circulating marker(s), imaging marker(s), and any combination thereof; (b) comparing the expression level of the one or more biomarkers, e.g., 1, 2, 3, 4, 5 or more biomarkers to an expression level of the one or more biomarkers, e.g., 1, 2, 3, 4, 5 or more biomarkers in a normal tissue sample; and (c) classifying the subject as a candidate for treatment comprising FLASH RT and the therapeutic agent if the expression level of the one or more biomarkers, e.g., 1, 2, 3, 4, 5 or more biomarkers in the tumor sample is modified compared to the expression level in the normal tissue sample. In some instances, the expression level of the one or more biomarkers, e.g., 1, 2, 3, 4, 5 or more biomarkers is modified if the expression level of at least one of the biomarkers is increased, or the expression level of at least one of the biomarkers is decreased, or the expression level of at least one of the biomarkers is increased and the expression level of at least one of the biomarkers is decreased compared to the expression level in a normal tissue sample. In certain cases, the expression level of the one or more biomarkers, e.g., 1, 2, 3, 4, 5 or more biomarkers is ranked or weighted. In some cases, the method further comprises performing functional imaging of the tumor.

In another aspect, provided herein is a method of selecting a treatment for a subject with cancer comprising (a) determining an expression level of one or more biomarkers, e.g., 1, 2, 3, 4, 5 or more biomarkers in a tumor sample from the subject, wherein the one or more biomarkers are selected from the group consisting of an immune cell marker(s), tumor cell marker(s), circulating marker(s), and any combination thereof; (b) comparing the expression level of the one or more biomarkers, e.g., 1, 2, 3, 4, 5 or more biomarkers to an expression level of the one or more biomarkers, e.g., 1, 2, 3, 4, 5 or more biomarkers in a normal tissue sample; and (c) selecting a treatment comprising FLASH RT and a therapeutic agent if the expression level of the one or more biomarkers, e.g., 1, 2, 3, 4, 5 or more biomarkers in the tumor sample is modified compared to the expression level in the normal tissue sample. In some embodiments, the method comprises performing functional imaging of the tumor; and selecting the treatment comprising FLASH RT and a therapeutic agent based on the functional imaging of the tumor. In some cases, the FLASH RT comprises contacting the tumor with a radiosensitizer.

In any of the above aspects and embodiments, the expression level of the one or more biomarkers, e.g., 1, 2, 3, 4, 5 or more biomarkers is modified if the expression level of at least one of the biomarkers is increased, or the expression level of at least one of the biomarkers is decreased, or the expression level of at least one of the biomarkers is increased and the expression level of at least one of the biomarkers is decreased compared to the expression level in a normal tissue sample. The expression level of the one or more biomarkers, e.g., 1, 2, 3, 4, 5 or more biomarkers can be ranked or weighted.

In any of the above aspects and embodiments, the FLASH RT is administered at a higher dose compared to a standard treatment protocol if the expression level of the one or more biomarkers, e.g., 1, 2, 3, 4, 5 or more biomarkers in the tumor sample is modified compared to the expression level in the normal tissue sample. In certain instances, the FLASH RT is administered as a hypofractionated radiation treatment if the expression level of the one or more biomarkers, e.g., 1, 2, 3, 4, 5 or more biomarkers in the tumor sample is modified compared to the expression level in the normal tissue sample. In other instances, the FLASH RT is administered as a hyperfractionated radiation treatment if the expression level of the one or more biomarkers, e.g., 1, 2, 3, 4, 5 or more biomarkers in the tumor sample is modified compared to the expression level in the normal tissue sample.

In any of the above aspects and embodiments, the therapeutic agent is an immune modulator selected from the group consisting of an inhibitor to an inhibitory checkpoint molecule, an activator of a stimulatory checkpoint molecule, a chemokine inhibitor, an inhibitor of macrophage migration inhibitory factor (MIF), a growth factor, a cytokine, an interleukin, an interferon, an antibody that binds to an immune system cell, a cellular immune modulator, a vaccine, an oncolytic virus, and any combination thereof.

In any of the above aspects and embodiments, the methods described herein can further comprise performing functional imaging of the tumor prior to administering the FLASH RT and/or the therapeutic agent.

The ionizing radiation (e.g., FLASH RT) and the therapeutic agent can be administered concomitantly. Alternatively, the FLASH RT and the therapeutic agent can be administered sequentially.

In another aspect, a kit is provided. The kit comprises reagents capable of detecting expression of the biomarkers described herein. In some embodiments, the kit comprises reagents capable of detecting nucleic acid (e.g., RNA) expression of the biomarkers. For example, the kit can comprise oligonucleotide primers that are capable amplifying a nucleic acid expressed by the biomarker genes described herein. In some embodiments, the kit further comprises an oligonucleotide probe that hybridizes to a biomarker nucleic acid or an amplified biomarker nucleic acid, or a complement thereof. Methods of amplifying and detecting nucleic acids are well known in the art, and can comprise PCR, RT-PCR real-time PCR, and quantitative real-time PCR, Northern analysis, sequencing of expressed nucleic acids, and hybridization of expressed and/or amplified nucleic acids to microarrays. In some embodiments, the kit comprises reagents that are capable of detecting proteins expression by the biomarkers described herein. In some embodiments, the reagents are antibodies that specifically bind to biomarker proteins. Methods of detecting protein expression are well known in the art, and include immunoassays, ELISA, Western analysis, and proteomic techniques.

In some embodiments of any of the above aspects and embodiments, the differences in the expression levels of each of the biomarkers in the tumor sample are increased or decreased by at least 10%, 20%, 30%, 40%, 50%, 60%, 70%, 80%, 90% or more compared to the expression level in normal tissue. In some embodiments, the expression levels of each of the biomarkers in the tumor sample are increased or decreased by at least 1-fold, 2-fold, 3-fold, 4-fold, 5-fold, 6-fold, 7-fold, 8-fold, 9-fold, 10 fold or more relative to the expression level in normal tissue.

In some embodiments, the average and/or ranked expression level of all the biomarkers in the tumor sample is increased or decreased relative to the expression level in normal tissue. Thus, in some embodiments, the average and/or ranked expression level of all the biomarkers in the tumor sample is increased or decreased by at least 10%, 20%, 30%, 40%, 50%, 60%, 70%, 80%, 90% or more compared to the expression level in normal tissue. In some embodiments, the expression levels in normal tissue are normalized to a control or baseline level. It will be understood that the expression level can also be compared to the expression level in the tumor sample before, after or during a treatment, course of treatment, or treatment plan. Thus, in some embodiments, the expression levels of each of the biomarkers in the tumor sample are increased or decreased by at least 10%, 20%, 30%, 40%, 50%, 60%, 70%, 80%, 90% or more compared to the expression level in the tumor sample before, during or after treatment.

Further, with regard to any of the above aspects and embodiments, the one or more biomarkers can comprise or consist of any combination of the biomarkers, for example, any of the biomarkers described herein, any combination of two or more biomarkers, any combination of three or more biomarkers, any combination of four or more biomarkers, any combination of five or more biomarkers, any combination of six or more biomarkers, and any combination of seven or more biomarkers.

In another aspect, the expression level of at least one, two, three, four or more of the biomarkers described herein is determined. The combination of expression levels of two or more biomarkers, e.g., 2, 3, 4, 5, 6 or more biomarkers can indicate that the subject with cancer is more sensitive to radiation compared to a control subject. This subject may be administered a reduced or decreased dose of radiation compared to a standard dose. In other instances, if the combination of expression levels of two or more biomarkers, e.g., 2, 3, 4, 5, 6 or more biomarkers can indicate that the subject with cancer is less sensitive to radiation compared to a control subject. A subject who is less sensitive to radiation may be administered an increased dose, a hypofractionated dose or a hyperfractionated dose of radiation. Optionally, radiation therapy may be administered in combination with an immune modulator, such as but not limited to, an anti-TIM4 antibody, an anti-MFG-E8 antibody, an anti-M199 antibody, and any combination thereof.

In some embodiments, the biomarker is CD44, MFG-E8, CD68, TGFβ, or any combination thereof. In certain embodiments, if a first biomarker has a high level of expression and a second biomarker has a low level of expression in a sample obtained from a subject with cancer relative to a control sample, then it is predicted that radiation treatment monotherapy may result in local tumor control failure. As such, this biomarker profile can indicate that the subject should be administered radiation treatment in combination with an immune modulator. Alternatively, this biomarker profile can indicate that the dose of radiation be increased (i.e., increased over a standard protocol dose). For instance, if the level of CD44 is high and the level of MFG-E8 is low in a subject's tumor sample compared to a control sample, then it is predicted that radiation treatment alone will not lead to a clinical response. In other words, a tumor sample having a high level of CD44 and a low level of MFG-E8 is likely to be insensitive or have a low sensitivity to ionizing radiation or FLASH radiation therapy.

In some cases, the biomarker profile described herein indicates that the subject should receive an increased dose of radiation and/or combination therapy comprising FLASH RT and an immune modulator, such as an anti-TIM4 antibody, anti-MFG-E8 antibody, anti-M199 antibody, and any combination thereof.

In other embodiments, if the level of CD44 is low compared to a normal sample and/or the level of MFG-E8 is high compared to a normal sample, the subject is likely to have a clinical response to ionizing radiation or FLASH monotherapy. In some cases, it is predicted that a subject with low level of CD44 and/or a high level of MFG-E8 is likely to be sensitive to ionizing radiation or FLASH radiation therapy.

In some embodiments, if a subject's tumor has a high level of CD68 compared to a control sample, the subject is predicted to have decreased survival after radiation monotherapy. As such, this subject can be administered a combination therapy comprising FLASH RT and an immune modulator. In other instances, if a subject's tumor has a low level of CD68 compared to a control sample, the subject is likely to have a clinical response to radiation monotherapy. It is predicted that this subject is sensitive to radiation. In certain cases, it may be indicated that the subject be administered a low dose or reduced dose of radiation compared to a standard protocol dose.

Flash Radiation

FLASH radiation can be administered to tissue (e.g., tumor cells) in a single pulse, or any sequence of pulses, with an interval between pulses of less than a second to several minutes. The dose of FLASH radiation can range from about 40 to greater than 500 Gy/sec. In embodiments, FLASH radiation allows for dose deposition up to 200 centimeters in living tissue at FLASH rates. In some embodiments, the dose of FLASH radiation is sufficient to kill tumor cells located up to 200 centimeters deep in human or animal tissue, for example, from 1 Gy up to more than 500 Gy, with a total beam-on delivery time of not more than 1 second. Each pulse within a FLASH sequence can be continuous or a sequence of shorter micro-pulses. In some embodiments, the dose per pulse is at least 0.1 Gy, and the dose rate per pulse is at least 40 Gy/sec (i.e. 0.1 Gy in 2.5 ms, 4 Gy in 10 ms, 20 Gy in 0.5 sec, etc.) and up to 1e7 Gy/sec as specified herein. The pulse duty cycle (i.e. temporal spacing) can have any value from 1 to 1e−9.

In some embodiments, FLASH radiation is delivered using high-energy particles or waves, such as x-rays, gamma rays, electron beams, or protons. In some embodiments, FLASH radiation is delivered as proton therapy. In some embodiments, the FLASH radiation is not delivered using electrons. In some embodiments, the proton therapy is delivered according to the following schedule:

FLASH:
    1. 20 Gy in 0.5 seconds (40 Gy/sec)
    2. 17.5 Gy in 0.4375 seconds (40 Gy/sec)
    3. 15 Gy in 0.375 seconds (40 Gy/sec)

Pulsed-FLASH:
    1. 10 pulses of 1.5 Gy in 10 seconds with a duty cycle of 0.1 or 10%
    2. 10 pulses of 1.75 Gy in 10 seconds with a duty cycle of 0.1 or 10%
    3. 10 pulses of 2 Gy in 10 seconds with a duty cycle of 0.1 or 10%

In contrast, conventional proton radiation therapy can be delivered according to the following schedule:

1. 20 Gy in 40 seconds (0.5 Gy/sec)
2. 17.5 Gy in 35 seconds (0.5 Gy/sec)
3. 15 Gy in 30 seconds (0.5 Gy/sec)

FLASH irradiation using electrons delivered by a linear electron accelerator is described, for example, in V. Favaudon, L. Caplier, V. Monceau, F. Pouzoulet, M. Sayarath, C. Fouillade, M.-F. Poupon, I. Brito, P. Hupé, J. Bourhis, J. Hall, J.-J. Fontaine, M.-C. Vozenin, Ultrahigh dose-rate FLASH irradiation increases the differential response between normal and tumor tissue in mice. Sci. Transl. Med. 6, 245ra93 (2014). Systems for producing FLASH radiation are described in U.S. patent application Ser. No. 15/089,330 (filed Apr. 1, 2016), which is incorporated by reference herein in its entirety for all purposes. Thus, in some embodiments, the radiation therapy or treatment system is a proton pencil beam scanning system that can be used for FLASH RT. More specifically, the system can include an accelerator and beam transport system and a nozzle that can be aimed toward an object. The nozzle includes a beam energy adjuster configured to adjust the beam by, for example, placing different thicknesses of material in the path of the beam to affect the energies of the particles in the beam. The nozzle is capable of quickly adjusting the particles in the beam to create a scanned beam (as opposed to a scattered beam) that delivers an entire, relatively high therapeutic radiation dose in the target volume. For example, a dose of four grays or more can be delivered along a specified beam direction (e.g., a given ray) in less than one second.

Each ray is a part of a scan pattern and irradiates tissue along a different line segment through the target volume (a "target line segment"). A high dose that can be delivered in a short period of time along a target line segment may be referred to as a "shot." In an embodiment, a shot can be adjusted in energy (intensity) or range and delivered to the target volume with a Spread Out Bragg Peak (SOBP) that provides a uniform and otherwise suitably modified dose to an entire target line segment.

Other types of radiation treatment systems that can be used for FLASH RT are described in the co-pending provisional application Ser. No. 62/434,053, filed Dec. 14, 2016, and entitled "Dynamic Three-Dimensional Compensator," which is hereby incorporated by reference in its entirety.

In some embodiments the radiation therapy or treatment system comprises an accelerator, a beam transport system, and a beam shaping system. In an embodiment, the accelerator may be radio frequency (RF) (linear accelerator, cyclotron, or synchrotron) or laser-based accelerator. The accelerator may deliver the dose in a pulsed, continuous or quasi-continuous manner. The beam transport may include magnetic elements (dipole, quadrupole, multipole), electrostatic elements, and slits or collimators. The beam shaping can be performed by a combination of magnetic, electrostatic and mechanical elements with the purpose of maximizing the conformality of the dose to the tumor. Embodiments include systems capable of delivering 3D conformal dose to the tumor in a single field or as a combination of multiple beamlets.

FLASH RT doses can be delivered as a single dose (a single fraction), or the total dose can be divided into multiple fractions that are delivered over time. In an embodiment, continuous monitoring of the tumor using, for example x-ray or magnetic resonance imaging (MRI) may be used by a medical technician to help determine when to turn on the beam when the target is in the defined target field, to further ensure optimal dose conformality.

FLASH RT can use very high energy charged particles (VHECPs) including, but not limited to, electrons, protons, and heavy ions, high energy photons (x-rays, gamma rays), or any high energy neutral particle, such as neutrons. High energy is defined as any energy which allows for dose deposition up to 200 centimeters in living tissue at FLASH rates. Intensity modulated (IM) FLASH RT and modulated arc (MA) FLASH RT provide means for achieving optimal dose conformity.

Radiation Treatment Planning Systems

In intensity modulated radiation therapy (IMRT) such as intensity modulated particle therapy (IMPT), beam intensity is varied across each treatment region (target) in a patient. Instead of being treated with a relatively large and uniform field, the patient is treated with a number of smaller beams (e.g., beam segments or beamlets), each of which can have its own energy and/or intensity value, and each of which can be delivered from a different direction or angle (which may be referred to as beam geometry). Because of the many possible beam geometries, the number of beams, and the range of beam energies or intensities across the beams and within each beam, there is effectively an infinite number (or at least a very large number) of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, and particularly considering the large number of patients that are undergoing or need to undergo radiation therapy during any given time period.

FIG. 1 shows a cross-sectional view of a possible beam geometry to a tumor (target 710) and the surrounding tumor microenvironment 720. In FIG. 1, a prescribed dose to be delivered into and across the target 710 is determined. Each portion of the target 710 can be represented by at least one 3D element known as a voxel; a portion may include more than one voxel. A portion of a target 710 or a voxel may also be referred to herein as a sub-volume; a sub-volume may include one or more portions or one or more voxels. As will be described in detail below, each portion or voxel may receive radiation from one or more beams delivered from different directions. The prescribed dose defines, for example, a dose value, or a minimum dose value and a maximum dose value, for each portion or voxel of the target 710. In an embodiment, the prescribed dose is the same for all portions (sub-volumes or voxels) of the target 710, such that a uniform dose is prescribed for the entire target 710.

In FIG. 1, directions (e.g., gantry angles relative to the patient or target, or nozzle directions relative to the patient or target) for delivering beams 705-707 into the target 710 are determined. The beams 705-707 can be proton beams, electron beams, photon beams, ion beams, or atom nuclei beams. The operation of determining beam directions can include determining the number of beams (the number of directions from which beams are to be delivered). The beams' paths may or may not overlap within the target 710, and may or may not overlap outside the target 710. In general, when generating the radiation treatment plan, one goal is to determine beam paths that minimize the irradiation dose of each sub-volume or voxel of the tissue outside the target 710. In some cases, organs deemed critical by the radiation oncologist may be required to receive less dose than other organs in the vicinity. Therefore, conventional treatment planning is driven by prescription thresholds of the calculated integral dose to the tumor and surrounding organs.

Figure 2:
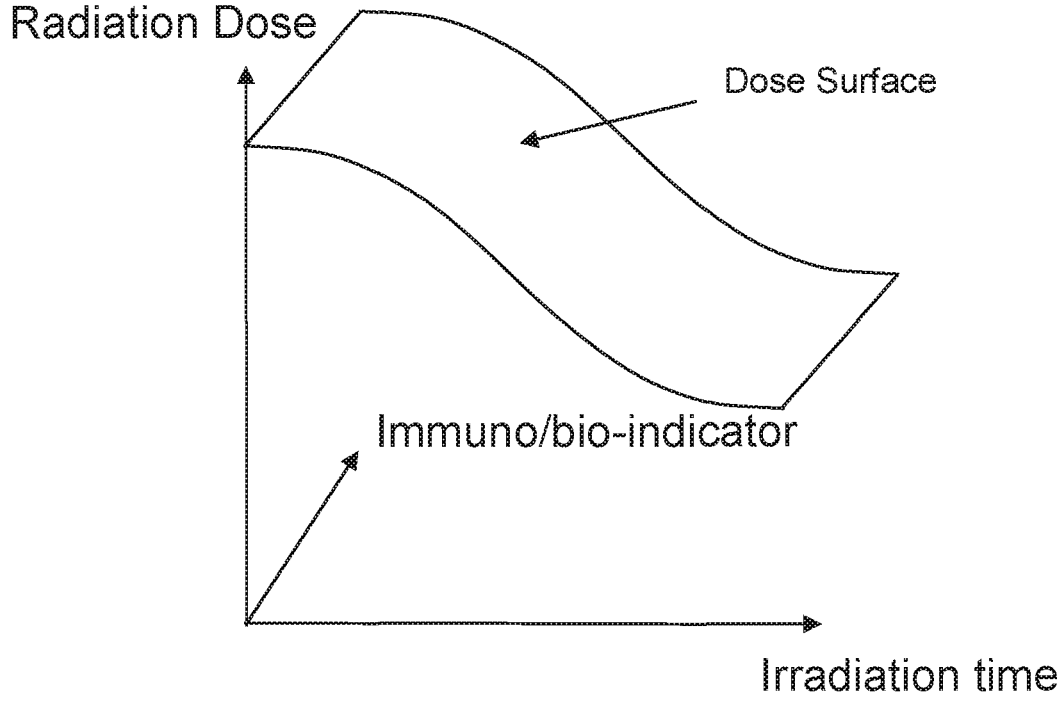
FIG. 2. shows a representative dose surface plot as an example of the variables used to determine dose threshold in an embodiment described herein.

The current disclosure provides additional criteria for determining the organ dose thresholds outside the target 710. FIG. 2 contains a 3-dimensional surface plot of dose vs time and one other variable. The dose delivered to a tumor will depend on more variables, but two are selected for the purposes of describing the embodiments without added complexity. In general the dose surface can depend on any number of variables, and will in generally be n-dimensional with n being greater than or equal to 1. In the case of the tumor microenvironment 720, the other parameters could be immune-sensitivity, response of the tumor to an immune modulator, or some other biological parameter. While in general the shape of this surface can vary, FIG. 2 shows an increasing dose threshold with decreasing irradiation time, and a slightly increasing dose threshold with increasing "immune-biological indicator".

In an embodiment, the time constraint can be met through geometrical construction of the beam configuration. Ideally, each sub-volume or voxel outside the target 710 is intersected, at most, by only a single beam. If some overlap between beam paths is permitted, then ideally each sub-volume or voxel outside the target 710 is intersected by not more than two beams, with most intersected by only a single beam. In an embodiment, as one means of achieving the aforementioned goal, the beam directions are determined such that the total amount of overlap between the beams' paths is minimized outside the target 710. In one such embodiment, the directions are determined such that the paths of the beams overlap within the target 710 and such that the total amount of overlap of the beams' paths outside the target 710 is less than the total amount of the overlap of the beams' paths within the target 710. In another such embodiment, the directions are determined so that the paths of the beams do not overlap at all outside the target 710. The beams' paths can lie within the same plane, or they can be in different planes.

The beams (705-707) are shown as passing through the patient, however this disclosure is not so limited. The beams 705-707 may also terminate within the target 710 as would be the case for ion and proton beams. In this case, beam energy determines the termination point within the target 710, which would need to be considered by the calculation engine and optimizer. Otherwise all other optimization parameters are the same.

While the operations in FIG. 1 are presented as occurring in series and in a certain order, the present disclosure is not so limited. The operations may be performed in a different order and/or in parallel, and they may also be performed in an iterative manner, as the number of beams (and accordingly, the number of directions), the beam directions, and the beam energies or intensities (and/or beam segment energies or intensities) used to deliver the prescribed dose are inter-related. As noted above, because of the different parameters that need to be considered, the range of values for those parameters, the interrelationship of those parameters, the need for treatment plans to be effective yet minimize risk to the patient, and the need to generate high-quality treatment plans quickly, the use of the treatment planning system 150 executing consistently on the computing system 100 (FIG. 3) for radiation treatment planning as disclosed herein is important.

Although multiple beams 705-707 are shown in FIG. 1, this does not mean that all beams are necessarily delivered at the same time or in overlapping time periods, although they can be. The number of beams delivered at any one time depends on the number of gantries or nozzles in the radiation treatment system and on the treatment plan.

In operation, in an embodiment, the beam segments are delivered sequentially. For example, the beam segment 705 is delivered to the target (turned on) and then turned off, then the beam segment 706 is turned on then off, then the beam segment 707 is turned on then off, and so on. Each beam segment may be turned on for only a fraction of a second (on the order of milliseconds). In an embodiment, all beams 705-707 may be turned on simultaneously.

As shown in FIG. 1, a sub-volume can be traversed by more than two beams, in which case the cumulative dose for the sub-volume is represented by adding the appropriate value for each beam that reaches the sub-volume. Such sub-volumes are known as overlap regions 730. That is, a total value is determined for each sub-volume in the target 710 by adding together the values for each beam region of each beam that reaches the sub-volume. Dose in the overlap regions can also be optimized by the constraints defined by the surface in FIG. 2.

The optimizer model can adjust the parameters that affect the calculated doses delivered to the target 710 to achieve a satisfactorily uniform cumulative dose across the target 710. A satisfactorily uniform cumulative dose is indicated when all the total values per sub-volume in the target 710 are the same or when the differences between the total values per sub-volume satisfy a threshold value.

The threshold value can be, for example, a value that specifies the range of differences that is permitted or that specifies a maximum permitted difference.

Dose limits can include, but are not limited to: a limit on irradiation time for each sub-volume (voxel) in the target (e.g., for each voxel of target tissue, treatment time<0.5 seconds); a limit on irradiation time for each sub-volume (voxel) outside the target (e.g., for each voxel of normal tissue, treatment time<0.5 second2); a limit on dose rate for each sub-volume (voxel) in the target (e.g., for each voxel of target tissue, dose rate>40 Gy/sec); and a limit on dose rate for each sub-volume (voxel) outside the target (e.g., for each voxel of normal tissue, dose rate>40 Gy/sec), a limit on dose and dose rate in the tumor micro-environment. In general, the limits are intended to minimize the amount of time that normal tissue is irradiated and maximize the immunological response.

In summary, embodiments described herein improve radiation treatment planning and the treatment itself by expanding FLASH RT to a wider variety of treatment platforms and target sites as well as optimizing delivery of FLASH RT to enhance the immune response. Treatment plans generated as described herein are superior for sparing normal tissue from radiation in comparison to conventional techniques even for non-FLASH dose rates by reducing, if not minimizing, the magnitude (and the integral in some cases) of the dose to normal tissue (outside the target) by design. When used with FLASH dose rates, management of patient motion is simplified. Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

In some embodiments, the methods described herein can be used with other types of external beam radiotherapy such as, but not limited to, IMPT, intensity modulated radiation therapy (IMRT), image-guided radiotherapy (IGRT), RapidArc™ radiotherapy, stereotactic body radiotherapy (SBRT), and stereotactic ablative radiotherapy (SABR).

Figure 3:
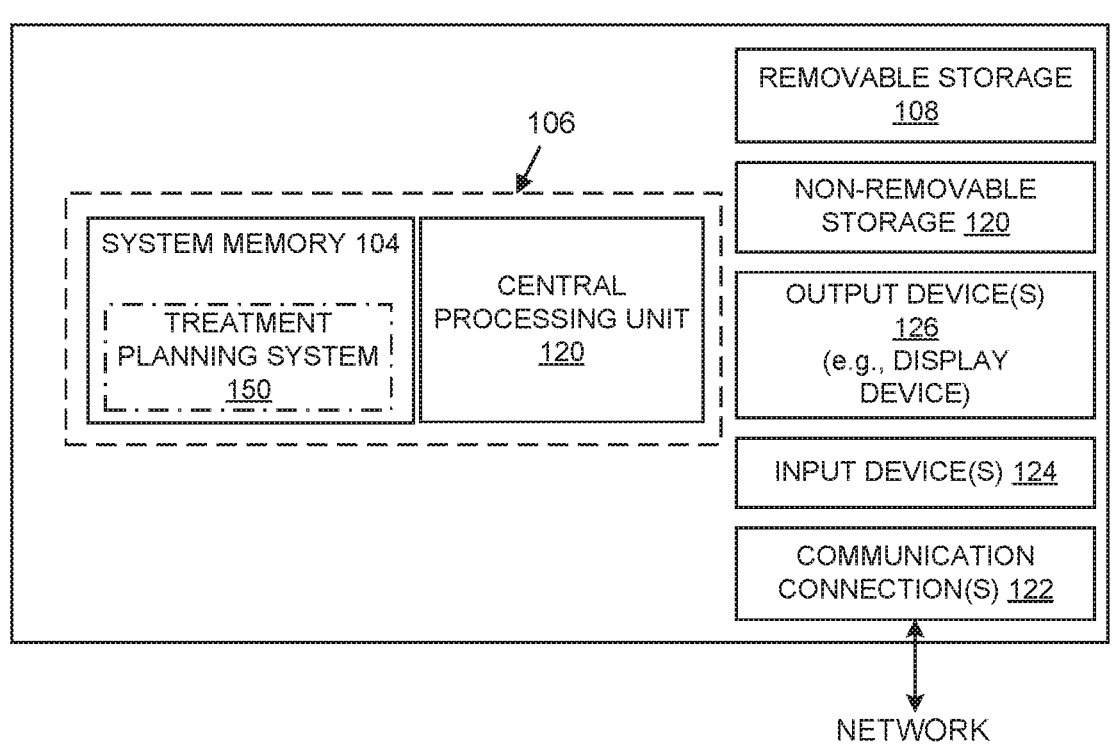
FIG. 3. is a block diagram of an example of a computing system upon which the embodiments described herein may be implemented.

FIG. 3 shows a block diagram of an example of a computing system 100 that can be used for radiation treatment planning. In its most basic configuration, the computing system 100 includes at least one processing unit 102 and system memory 104. This most basic configuration is illustrated in FIG. 3 by dashed line 106. The computing system 100 may also have additional features and/or functionality. For example, the computing system 100 may also include additional storage (removable and/or non-removable) including, but not limited to, magnetic or optical disks or tape. Such additional storage is illustrated in FIG. 3 by removable storage 108 and non-removable storage 120. The computing system 100 may also contain communications connection(s) 122 that allow the computing system 100 to communicate with other devices, e.g., in a networked environment using logical connections to one or more remote computers.

The computing system 100 also includes input device(s) 124 such as keyboard, mouse, pen, voice input device, touch input device, etc. Output device(s) 126 such as a display device, speakers, printer, etc., are also included.

In the example of FIG. 3, the memory system 104 includes computer-readable instructions, data structures, program modules, and the like associated with a treatment planning system 150. However, the treatment planning system 150 may instead reside in any one of the computer storage media used by the computing system 100, or may be distributed over some combination of the computer storage media, or may be distributed over some combination of networked computers.

The treatment planning system 150 can be used to develop a radiation treatment plan for a particular patient by receiving patient-specific information (e.g., geometry information) that is input to and processed by the treatment planning system. The input patient-specific information may contain any combination of parameters that can practically affect the radiation treatment plan. For example, the patient-specific information may be organized as a vector or a data structure including feature elements for: size and shape of the target volume; location of the target volume; size and shape of an organ at risk; type of an organ at risk; a part of the target volume that overlaps an organ; and a part of an organ that overlaps the target volume.

The treatment planning system 150 may be used to predict dose parameters for a treatment plan corresponding to a particular patient. The dose treatment planning system 150 may include a dose-volume histogram (DVH) estimation model, where the predicted quantity is a dose volume histogram. In other embodiments, the treatment planning system 150 also generates a prediction based on a distance to a target (DTH) histogram, which expresses the distance from a region of interest (ROI) to a radiation target. In general, the treatment planning system 150 is implemented as any model suitable for predicting dosage (as a dose histogram or spatial 3D dose distribution) for a radiation treatment plan.

As mentioned above, the radiation treatment planning system 150 can account for both the spatial domain and the time domain. A time-dependent component can be included in treatment planning for IM or MA FLASH RT with VHECPs, for example.

In some embodiments, the treatment planning system 150 considers the combination of FLASH RT and immunotherapy. The treatment planning system 150 incorporates immunotherapy into treatment planning, including how immunotherapy affects the dose regimen and the impact of immunotherapy on radiation delivery and dose rate. In general, treatment planning system 150 determines a final radiation treatment plan that integrates FLASH RT and immunotherapy. For example, the treatment planning system 150 can iteratively evaluate the FLASH aspects of radiation treatment and the immunotherapy/biological aspects of radiation treatment to generate a final radiation treatment plan that optimizes the combination of both aspects.

For example, the planner defines a set of quality metrics. For planning, the metrics are defined such that a smaller value is preferred over a larger value. The planner also defines a relative priority or weight (wi) for each of the quality metrics. The task of developing an optimal plan is then formulated as a quadratic cost function C: $C=\text{sum}(wi(Qi-qi)2)$, where qi is the value of the quality metric that can be achieved for a particular treatment plan. The optimal plan is determined by minimizing the cost function C.

Another way to assist the planner is to use a multi-criteria optimization (MCO) approach for treatment planning. Pareto surface navigation is an MCO technique that facilitates exploration of the tradeoffs between clinical goals. For a given set of clinical goals, a treatment plan is considered to be Pareto optimal if it satisfies the goals and none of the metrics can be improved without worsening at least one of the other metrics. The set of Pareto optimal plans define a Pareto surface related to the set of clinical goals. Movement along the Pareto surface results in tradeoffs between the clinical goals; some metrics will improve at the cost of worsening one or more other metrics. The planner can navigate along the Pareto surface and choose a final (optimized) radiation treatment plan that seems to be the best according to the criteria applied by the planner, or a treatment plan can be selected automatically based on its proximity to the Pareto surface.

Metrics associated with the combination of FLASH RT and immunotherapy include metrics associated with, for example, target homogeneity, critical organ sparing, prescribed doses, dose delivery rates, normal and tumor tissue toxicity, etc.

Figure 4:
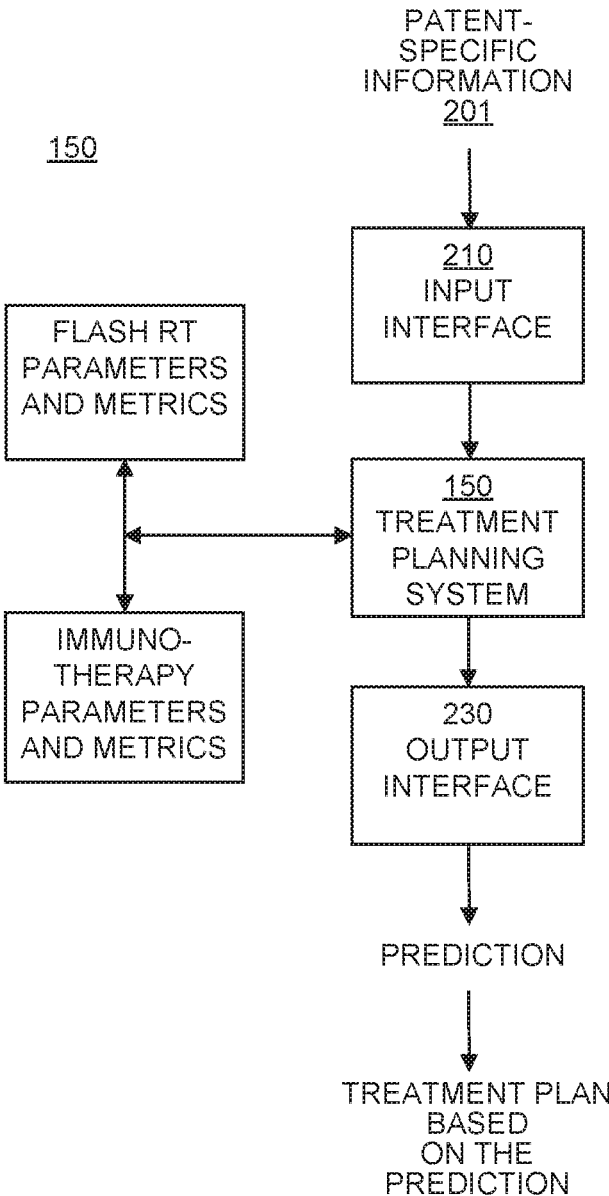
FIG. 4. is a block diagram illustrating an example of an automated radiation treatment planning system in an embodiment described herein.

FIG. 4 is a block diagram illustrating an embodiment of an automated radiation therapy treatment planning system 150. The treatment planning system 150 includes an input interface 210 to receive patient-specific information (data) 201, and an output interface 230. The treatment planning system 150 in whole or in part may be implemented as a software program, hardware logic, or a combination thereof on/using the computing system 100 (FIG. 3).

The radiation therapy treatment planning system 150 also receives or accesses FLASH RT parameters and metrics and immunotherapy parameters and metrics. Examples of the metrics are described herein. FLASH RT parameters can include, for example, beam type, beam energy, the angle of the beam relative to the patient/target volume, beam shape, dose delivery schedule, total dose and irradiation time for any given normal tissue volume outside the tumor, as well as dose and irradiation time within the tumor microenvironment which optimizes the immunological response. Immunotherapy parameters can include, for example, the type of drug or immune modulator administered to the subject, tumor antigen, neoantigen, or antibody administered, dosage, and delivery schedule (e.g., before, after, and/or during FLASH RT).

The treatment planning system 150 yields a prediction result, e.g., an achievable dose distribution prediction. A treatment plan based on the prediction result can then be generated. In an embodiment, the prediction result is accompanied by parameters indicative of the quality of the prediction, such as reliability of the result, complexity of the predicted plan, and probability of the result.

In some embodiments, the radiation treatment planning systems described herein will result in a prediction that a lower effective dose of radiation, e.g., FLASH radiation, can be administered to a subject based on a response of the subject to immunotherapy. For example, in some embodiments, the radiation treatment planning system(s) will predict that a lower effective dose of radiation, e.g., FLASH radiation, can be administered to a subject if the tumor in the subject responds favorably to immunotherapy, e.g., the tumor is reduced in size following immunotherapy.

In some embodiments, the radiation treatment planning systems described herein will result in a prediction to change the effective dose of radiation, e.g., FLASH radiation, based on parameters that enhance the immune response, e.g., increase the delivery or activity of an immune modulator to more effectively treat a tumor in a subject.

Biomarkers for Radiotherapy Selection

The biomarkers described herein can be used to stratify patients to receive individualized, tailored radiotherapy (e.g., FLASH RT) in combination with an immune modulator agent. The biomarkers can also be used to monitor the efficacy of immune modulator therapy on patients with cancer. The biomarkers include, but are not limited to, one or more immune cell biomarkers, one or more tumor cell biomarkers, one or more circulating biomarkers, one or more imaging biomarkers, and any combination thereof. For instances, an immune cell biomarker can provide information about the location and/or activity of a specific cell population, such as a T cell population. An immune cell biomarker or tumor cell biomarker can be a genetic biomarker, polynucleotide biomarker, or a protein biomarker. In some embodiments, an immune cell biomarker is a specific polynucleotide (e.g., RNA and microRNA) or protein that is expressed at a higher level by a particular immune cell compared to a non-immune cell or a different type of immune cell. Similarly, a tumor cell biomarker can a specific polynucleotide (e.g., RNA and microRNA) or protein that is expressed at a higher level by a tumor cell compared to a non-tumor cell. For example, the tumor cell biomarker can be a protein or a polynucleotide encoding said protein that is associated with proliferation and/or metastasis of a tumor cell. In some cases, the protein can be involved in angiogenesis or other processes that are activated by a tumor cell. The tumor biomarker can be an oncogene or a tumor suppressor. In some instances, a tumor cell biomarker is a gene variation, gene mutation, copy number variant (CNV), single nucleotide polymorphism (SNP), and the like that is present in a tumor cell, but not in a non-tumor cell. In some embodiments, a circulating biomarker is an exosome (i.e., a cell-derived vesicle that can be found in a body fluid). Examples of useful biomarkers includes those described in U.S. Patent Appl. Publ. No. 20160024594, the disclosure of which is hereby incorporated by reference for all purposes.

The biomarker set can include, but is not limited to, CD44, milk fat globule-EGF factor 8 (MFG-E8), CD68 and TGFβ. CD44 is a cell-surface glycoprotein that plays a role in cell proliferation, cell-cell interactions, cell adhesion, and cell migration of various cell types including lymphocytes and cancer cells. The human CD44 polypeptide sequence is set forth in, e.g., GenBank Accession No. NP_000601. The human CD44 mRNA (coding) sequence is set forth in, e.g., GenBank Accession No. NM_000610. Milk fat globule-EGF factor 8 protein (MFG-E8) is a macrophage-produced protein that promotes engulfment and clearance of apoptotic cells in tumors. The human MFG-E8 polypeptide sequence is set forth in, e.g., GenBank Accession No. NP_005919. The human MFG-E8 mRNA (coding) sequence is set forth in, e.g., GenBank Accession No. NM_005928. CD68 is a 110-kD transmembrane glycoprotein that is highly expressed by human monocytes and tissue macrophages. The protein primarily localizes to lysosomes and endosomes with a smaller fraction circulating to the cell surface. It is a type I integral membrane protein with a heavily glycosylated extracellular domain and binds to tissue- and organ-specific lectins or selectins. CD68 is also a member of the scavenger receptor family. The human CD68 polypeptide sequence is set forth in, e.g., GenBank Accession No. NP_001242. The human CD68 mRNA (coding) sequence is set forth in, e.g., GenBank Accession No. NM_001251. TGFβ is a cytokine that is involved in cell growth, cell proliferation, cell differentiation, apoptosis, homeostasis and many other cellular processes. The human TGFβ polypeptide sequence is set forth in, e.g., GenBank Accession No. NP_000651. The human TGFβ mRNA (coding) sequence is set forth in, e.g., GenBank Accession No. NM_000660.

It will be understood that the expression levels of each of the biomarkers described herein in the patient sample can increase or decrease relative to the expression level of the tumor biomarker in a normal or control tissue sample. For example, the expression level of one tumor biomarker can increase in the tumor sample compared to the expression level in a normal tissue, whereas the expression level of a second biomarker can decrease in the tumor sample compared to the expression level in a normal tissue. The expression level can also be based on the average, combination or sum of the all the tumor biomarker expression levels in the patient sample. For example, the expression level of each biomarker in the patient sample can be ranked or weighted to produce a ranked value that is higher or lower than the normal tissue value (which can be a normalized value, for example, set to 1).

In some embodiments, biomarker expression is determined in a biological sample from the subject having a tumor. In some embodiments, the biological sample is a tumor sample. The tumor sample can be a biopsy comprising tumor cells from the tumor. In some embodiments, the biological sample comprises a bodily fluid, such as but not limited to blood, serum, plasma, or urine, and/or cells or tissues from the subject. In some embodiments, the biological sample is a formalin-fixed and paraffin embedded tissue or tumor sample. In some embodiments, the biological sample is a frozen tissue or tumor sample. Thus, in some embodiments, one or more steps of the methods described herein are carried out in vitro. For example, in some embodiments, biomarker expression is determined in vitro.

In some embodiments, the normal tissue sample comprises non-tumor cells from the same tissue type as the tumor. In some embodiments, the normal tissue sample is obtained from the same subject diagnosed with the tumor. A normal tissue sample can also be a control sample of the same tissue-type from a different subject. The expression level of the normal tissue sample can also be an average or mean value obtained from a population of normal tissue samples.

The level of expression of the biomarkers described herein can be determined using any method known in the art. For example, the level of expression can be determined by detecting the expression of a nucleic acid (e.g., RNA, mRNA or microRNA) or the protein encoded by the nucleic acid.

Exemplary methods for detecting expression levels of nucleic acids include, without limitation, Northern analysis, polymerase chain reaction (PCR), reverse transcription PCR (RT-PCR), real-time PCR, quantitative real-time PCR, and DNA microarrays.

Exemplary methods for detecting expression levels of proteins (e.g., polypeptides) include, without limitation, immunohistochemistry, ELISA, Western analysis, HPLC, and proteomics assays. In some embodiments, the protein expression level is determined by immunohistochemistry using the Allred method to assign a score (see, e.g., Allred, D. C., Connection 9:4-5, 2005, which is incorporated by reference herein). For example, formalin-fixed, paraffin embedded tissues are contacted with an antibody that specifically binds a biomarker described herein. The bound antibody is detected with a detectable label or secondary antibody coupled with a detectable label, such as a colorimetric label (e.g., an enzymatic substrate produce by HRP or AP). The antibody positive signal is scored by estimating the proportion of positive tumor cells and their average staining intensity. Both the proportion and intensity scores are combined into a total score that weighs both factors.

In some embodiments, the protein expression level is determined by digital pathology. Digital pathology methods include scanning images of tissues on a solid support, such as a glass slide. The glass slides are scanned into whole slide images using a scanning device. The scanned images are typically stored in an information management system for archival and retrieval. Image analysis tools can be used to obtain objective quantitative measurements from the digital slides. For example, the area and intensity of immunohistochemical staining can be analyzed using the appropriate image analysis tools. Digital pathology systems can include scanners, analytics (visualization software, information management systems and image analysis platforms), storage and communication (sharing services, software). Digital pathology systems are available from numerous commercial suppliers, for example, Aperio Technologies, Inc. (a subsidiary of Leica Microsystems GmbH), and Ventana Medical Systems, Inc. (now part of Roche). Expression levels can be quantified by commercial service providers, including Flagship Biosciences (CO), Pathology, Inc. (CA), Quest Diagnostics (NJ), and Premier Laboratory LLC (CO).

In some embodiments, imaging of the tumor, such as functional imaging is also used to identify or select a cancer patient who should receive the combination therapy described herein. Non-limiting examples of functional imaging include single-photon emission computed tomography, optical imaging, ultrasonography, positron emission tomography (PET), computed tomography (CT), perfusion computed tomography, magnetic resonance imaging (MRI), functional magnetic resonance imaging, magnetic resonance sectroscopic imaging, dynamic contrast-enhanced imaging, diffusion-weighted imaging, blood-oxygenation level dependent imaging, magnetic resonance spectroscopy, magnetic resonance lymphography, and any combination thereof. Any type of functional imaging such as multimodality imaging can be performed to characterize the tumor, to determine the delineation of the tumor, the extent of the tumor, the tumor volume, and/or to assess the tumor microenvironment (e.g., the environment surrounding the tumor). Functional imaging can aid in selecting the best treatment option and/or in monitoring response to the treatment.

Methods for Selecting a Course of Treatment

The expression levels of the biomarkers can be used to determine or select a course of treatment in a subject diagnosed with a tumor. For example, in some embodiments, the treatment comprises administering ionizing radiation, such as FLASH RT, to the tumor in the subject. The ionizing radiation can also be administered to the entire subject or a portion thereof, especially if the tumor is dispersed or mobile. In some embodiments, the treatment further comprises contacting the tumor with a radiosensitizer. In some embodiments, the treatment further comprises administering a compound or biologic drug, such as an antibody, that inhibits an immune checkpoint pathway, to the subject. In some embodiments, the treatment comprises administering a FLASH radiation treatment protocol in combination with an immune modulator.

The course of treatment can be selected based on the expression levels of the biomarkers. For example, the expression levels can be used to determine if radiation therapy is appropriate for the subject (i.e., for making a go/no go decision on radiotherapy). Further, if the expression levels of the biomarkers are increased relative to a normal or control value, then the effective radiation dose to the tumor can be increased, and/or the fractionation schedule modified accordingly. In some embodiments, the effective dose of FLASH RT to the tumor is increased. The radiation dose to the blood vessels feeding the tumor can also be increased. In some cases, a hypofractionated radiation treatment is administered. Alternatively, a hyperfractionated radiation treatment is administered. In some embodiments, FLASH radiation treatment is provided in combination with immune modulator treatment.

In some embodiments, if the expression levels of the biomarkers are increased relative to a normal or control value, then the treatment can comprise administering ionizing radiation, such as FLASH RT, to the tumor. In some embodiments, if the expression levels of the biomarkers are decreased relative to a normal or control value, then the treatment can comprise decreasing the amount of ionizing radiation or FLASH RT administered to the tumor.

The treatment can also comprise modifying an existing course of treatment. For example, in some embodiments, the existing course of treatment is modified to increase the effective dose of the ionizing radiation, e.g., FLASH radiation, administered to the tumor. In some embodiments, the effective dose of ionizing radiation, such as FLASH radiation, is increased by increasing the amount of ionizing radiation administered to the tumor and/or contacting the tumor with a radiosensitizer. In some embodiments, the existing course of treatment is modified to decrease the effective dose of the ionizing radiation administered to the tumor. In some embodiments, the treatment comprises modifying a standard radiation treatment protocol in combination with administering an immune modulator.

In some embodiments, the effective dose of ionizing radiation, e.g., FLASH radiation, administered to the tumor is increased if the level of one or more biomarkers described herein is elevated in the tumor environment. For example, the effective dose of ionizing radiation is increased as compared to the standard of care for a subject that does not have elevated levels of the biomarker(s) in the tumor environment. This applies to subjects who are currently not undergoing radiation therapy as well as modifying an existing course of treatment for subjects undergoing radiation therapy. Thus, the effective dose of ionizing radiation can be increased from the current effective dose if the subject is already undergoing radiation therapy for a tumor. The radiation therapy can be modified to reduce the constraints on neighboring healthy tissue. For example, if the biomarker level in the tumor environment indicates more aggressive radiation therapy is required, the treatment plan can be modified so that the constraints on the border between healthy tissue and tumor tissue are decreased. This would result in a trade-off between damaging some healthy tissue in order to kill more of the tumor tissue.

In some embodiments, the treatment comprises a combination of radiation therapy and an immune modulator agent (including a radiosensitizer). In some embodiments, the treatment comprises a combination of FLASH radiation therapy and an immune modulator agent (including a radiosensitizer). In some embodiments, the effective dose of ionizing radiation administered to the tumor is not changed (e.g., relative to the standard of care or relative to an existing course of treatment) when an immune modulator agent is administered to the subject. For example, in some embodiments, the subject is administered an effective dose of ionizing radiation that is the same or similar to that administered to a subject that does not have elevated levels of one or more biomarkers described herein in the tumor environment, and the subject is further administered an immune modulator agent. In some embodiments, the effective dose of ionizing radiation administered to the tumor is based on the standard of care for a subject that does not have elevated levels of the biomarker(s) in the tumor environment, and the subject is further administered an immune modulator agent. In some embodiments involving an existing course of treatment, the effective dose of ionizing radiation is maintained at the current effective dose, and an anti-cancer agent is administered to the subject in combination with the ionizing radiation if the level of one or more biomarkers described herein is elevated in the tumor environment.

In some embodiments, the treatment plan is developed and/or modified based on the expression levels of the biomarkers described herein.

The course of treatment can also be selected by using an algorithm that determines the expression level of the biomarkers in the tumor sample relative to the level in the normal sample. The algorithm can be a linear regression algorithm that includes the biomarker expression levels and coefficients (i.e., weights) for combining the expression levels. In some embodiments, the algorithm comprises a least squares fit to calculate the coefficients. If the algorithm determines that the expression level of the biomarkers in the tumor sample is increased or decreased relative to the normal sample, then the appropriate course of treatment can be assigned. In some embodiments, the algorithm is a nonparametric regression tree. In some embodiments, standard statistical methods were used to analyze the data to determine which biomarkers were most predictive of clinical survival or local tumor control failure.

In some embodiments, the method described herein is a computer implemented method. In some embodiments, the computer implemented method comprises a linear regression model that assigns a ranked or weighted value to the expression levels of the biomarkers described herein. In some embodiments, the disclosure provides a computer-readable medium, the medium providing instructions to cause a computer to perform a method described herein. For example, the medium can provide instructions to cause a computer to assign a ranked or weighted value to the expression levels of the biomarkers described herein.

Radiation Therapy

The expression levels of the tumor biomarkers described herein can be used to optimize treatment of patients with radiotherapy, such as FLASH RT. For example, the therapeutic dose of the radiation administered to the tumor or subject can be adjusted based on the expression levels of the biomarkers. The effective dose of ionizing radiation varies with the type of tumor and stage of cancer that needs to be treated. The effective dose can also vary based on other treatment modalities being administered to the patient, for example chemotherapeutic treatments and surgical treatments, and whether the radiation is administered pre- or post-surgery. In general, a conventional curative therapeutic dose for a solid epithelial tumor ranges from about 60 to 80 gray (Gy), whereas a curative dose for a lymphoma is about 20 to 40 Gy. In general, preventative doses can be 45-60 Gy. For FLASH irradiation, the curative therapeutic dose for a solid epithelial tumor can range from about 20 to 200 gray (Gy), whereas a curative dose for a lymphoma is about 10 to 200 Gy, with preventative doses from 5-500 Gy.

The therapeutic dose can be delivered in fractions. Fractionation refers to spreading out the total dose of radiation over time, for example, over days, weeks or months. The dose delivered in each fraction can be about 1.5-2 Gy per day. The treatment plan can include a fraction treatment one or more times per day, every other day, weekly, etc. depending on the treatment needs of each patient. For example, a hypofractionation schedule comprises dividing the total dose into several relatively large doses, and administering the doses at least one day apart. Exemplary hypofraction doses are 3 Gy to 20 Gy per fraction. An exemplary fractionation schedule that can be used to treat lung cancer is Continuous Hyperfractionated Accelerated Radiation therapy (CHART), which consists of three small fractions per day.

In some embodiments, FLASH RT includes contacting the tumor in the subject with a radiosensitizer. Exemplary radiosensitizers include hypoxia radiosensitizers such as misonidazole, metronidazole, and trans-sodium crocetinate, a compound that helps to increase the diffusion of oxygen into hypoxic tumor tissue. The radiosensitizer can also be a DNA damage response inhibitor interfering with base excision repair (BER), nucleotide excision repair (NER), mismatch repair (MMR), recombinational repair comprising homologous recombination (HR) and non-homologous end-joining (NHEJ), and direct repair mechanisms. SSB repair mechanisms include BER, NER, or MMR pathways whilst DSB repair mechanisms consist of HR and NHEJ pathways. Radiation causes DNA breaks that if not repaired are lethal. Single strand breaks are repaired through a combination of BER, NER and MMR mechanisms using the intact DNA strand as a template. The predominant pathway of SSB repair is the BER utilizing a family of related enzymes termed poly-(ADP-ribose) polymerases (PARP). Thus, the radiosensitizer can include DNA damage response inhibitors such as Poly (ADP) ribose polymerase (PARP) inhibitors.

The biomarkers described herein are useful in developing and modifying treatment plans for patients diagnosed with a tumor or cancer. The treatment plan can include visualizing or measuring the tumor volume that needs to be irradiated, the optimal or effective dose of radiation administered to the tumor, and the maximum dose to prevent damage to nearby healthy tissue or organs at risk. Algorithms can used in treatment planning, and include dose calculation algorithms based on the particular radiotherapy technique parameters employed, e.g., gantry angle, MLC leaf positions, etc., and search algorithms which use various techniques to adjust system parameters between dose calculations to optimize the effectiveness of the treatment. Exemplary dose calculation algorithms include various Monte Carlo ("MC") techniques and pencil beam convolution ("PBC"). Exemplary search algorithms include various simulated annealing ("SA") techniques, algebraic inverse treatment planning ("AITP"), and simultaneous iterative inverse treatment planning ("SIITP"). Such techniques, and others, are included within the scope of this disclosure.

Treatment planning algorithms may be implemented as part of an integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters. The Eclipse™ Treatment Planning System offered by the assignee of the present application includes such an integrated software program. Methods for optimizing treatment plans are described in U.S. Pat. No. 7,801,270, which is incorporated by reference herein.

In some embodiments, the biomarkers described herein can be used to monitor the progress of tumor control after FLASH radiation therapy. For example, the expression levels of the biomarkers before and after ionizing FLASH radiation therapy can be compared. In some embodiments, if the expression levels of biomarkers increase after radiotherapy, this suggests that the tumor is continuing to grow in size. Thus, the radiation treatment can be modified based on monitoring tumor growth using the biomarkers described herein.

The biomarkers described herein can be used with any radiation therapy technique known in the art. Radiation therapy techniques include external-beam radiotherapy ("EBRT") and Intensity Modulated Radiotherapy ("IMRT"), which can be administered by a radiotherapy system, such as a linear accelerator, equipped with a multileaf collimator ("MLC"). The use of multileaf collimators and IMRT allows the patient to be treated from multiple angles while varying the shape and dose of the radiation beam, thereby avoiding excess irradiation of nearby healthy tissue. Other exemplary radiation therapy techniques include stereotactic body radiotherapy (SBRT), volumetric modulated arc therapy, three-dimensional conformal radiotherapy ("3D conformal" or "3DCRT"), image-guided radiotherapy (IGRT). The radiation therapy techniques can also include Adaptive radiotherapy (ART), a form of IGRT that can revise the treatment during the course of radiotherapy in order to optimize the dose distribution depending on patient anatomy changes, and organ and tumor shape. Another radiation therapy technique is brachytherapy. In brachytherapy, a radioactive source is implanted within the body of the subject, such that the radioactive source is near the tumor. As used herein, the term radiotherapy should be broadly construed and is intended to include various techniques used to irradiate a patient, including use of photons (such as high energy x-rays and gamma rays), particles (such as electron and proton beams), FLASH RT, and radiosurgical techniques. Further, any method of providing conformal radiation to a target volume is intended to be within the scope of the present disclosure.

Therapeutic Agents

FLASH radiation therapy described herein can be administered in combination with one or more therapeutic agents. Example of therapeutic agents include immune modulators, senolytic agents, radiosentizers, and nanoparticles.

In some embodiments, the therapeutic agent is a mitotic spindle inhibitor. In some embodiments, flash radiation therapy is combined with a mitotic spindle inhibitor such as a cyclin inhibitor, for example, a CDK4/6 inhibitor (e.g., Pablociclib), AURKA inhibitors such as the small molecules Alisertib and Tozasertib, compounds that block TPX2-AURKA complexes such as a complex disruptor (GSK1070916) (Asteriti et al., 2015; Janeček et al., 2016), and Taxanes (such as Docetaxel, Paclitaxel).

In some embodiments, the therapeutic agent is a DNA repair and response pathway inhibitor. In some embodiments, flash radiation therapy is combined with a PARP inhibitor (e.g., Talazoparib, Rucaparib, Olaparib) (Lord and Ashworth, 2016; Murai et al., 2012), a RAD51 inhibitor (RI-1), or an inhibitor of DNA damage response kinases such as CHCK1 (AZD7762), ATM (KU-55933, KU-60019, NU7026, VE-821), and ATR (NU7026).

In some embodiments, the therapeutic agent is an inhibitor of the KRAS and/or MAPK pathway. In some embodiments, flash radiation therapy is combined with inhibitors upstream and/or downstream of KRAS. Upstream inhibitors can target EGFR (Erlotinib, Gefitinib, Lapatinib, Afatinib) and/or SHP2 (RMC-4550). Downstream inhibitors include inhibitors of MEK (Trametinib, Selumetinib, PD0325901), BRAF (Dabrafenib, Vermurafenib, PLX-4720), or ERK (SCH772984, LY3214996, GDC-0994).

In some embodiments, the therapeutic agent is an inhibitor of the Epithelial to Mesenchymal (EMT) Transition. TGF-beta is a known driver of EMT. Thus, in some embodiments, flash radiation therapy is combined with an inhibitor of the EMT Transition, such as a small molecule inhibitor (e.g., SD-208, LY2109761, LY21157299) or an antibody or fragments thereof that binds TGF-beta.

In some embodiments, the therapeutic agent induces or is an activator of the THil Pathway. T helper type 1 (Th1) cells are a subset of CD4+ effector T cells and play a key role in immune response as well as cancer immunotherapy. Th1 subtype cells are involved in activating antigen presenting cells (APCs) and also of recruitment of macrophages or mast cells to the tumor site [1]. They are also involved in direct activation of cytokines in the tumor microenvironment that can lead to enhanced tumor cell killing [2]. The pathway is inhibited by Flash radiation compared to untreated mice. Therefore, in some embodiments, flash radiation therapy is combined with an activator of the TH1 pathway, such as an adjuvant that induces Th1 activity. The adjuvants that can be used in combination with FLASH radiation include but are not limited to 1) cytokines associated with Th1 activation such as IL-12, IFN-alpha, beta or gamma, IL-2, IL-18, IL-27, CD80 (drug target abatacept, beletacept, galaximab), ICAM1 and TNF-alpha [3]; 2) Toll-like receptor agonists for TLR4 and TLR9, such as monophosphoryl lipid A and Bacillus Calmette-Guerin, Agatolimod, ISS-1018, HYB2055, and MGN1703; 3) STAT3 modulators like danvatirsen and OPB-31121; and 4) Inactivated bacteria/parasites or their derivates that trigger interferon gamma or IL-12 production, included but not limited to *Listeria monocytogenes, Leishmania major* and *Toxoplasma gondii, Mycobacterium tuberculosis*, staphylococcus enteroxin B and unmethylated CpG nucleotides that activate Th1 response in the body[4]. In addition gene therapy systems including bacterial or virus based gene expression systems that lead to production of IL2, IL-12 and TEN-gamma when injected at the tumor site can be used to activate the Th1 response.

In some embodiments, the therapeutic agent is an activator of the Phosphatase and Tensin Homolog (PTEN) pathway, which is protective for carcinogenesis. The PTEN pathway was activated in Flash irradiated tissues, and therefore Flash irradiation is predicted to have protective effects on tissue compared to conventional radiation. The inventors also observed reduced lung fibrosis in Flash vs conventional irradiated mice, and therefore Flash irradiation could reduce lung fibrosis through activation of the PTEN pathway. Therefore, in some embodiments, flash radiation therapy is combined with an activator of the PEEN pathway. Activators/agonists of the PTEN pathway are described in US 2011/0189169 A1, and include mTOR inhibitors such as rapamycin (Rapanume®, sirolimus, ATC code L04AA10 commercially available from Wyeth) and its chemical analogues such as CCI-779 (temsirolimus, Anatomical Therapeutic Chemical (ATC) code L01XE09, commercially available from Wyeth), RAD-001 (everolimus, ATC code L04AA18. commercially available from Novartis) and AP-2357 (Granville et al., Clin. Cancer Res. 12:679, 2006), which are herein incorporated by reference. Additional activators of PTEN activity include Src inhibitors, p38 MAPK modulators, NF-kB inhibitors, PPAR-gamma modulators, and IGF-1R modulators; Ublituximab, Rituximab, Sunitinib, (Induces PTEN), Trastuzumab and Pertuzumab (Increases PTEN through Src inhibition), Resistin (p38 MAPK modulator, increases PTEN), Simvastatin (NF-kB inhibitor), Lovastatin and Rosiglitazone (PPAR-gamma modulators), NVP-AEW541 (IGF-1R modulator that increases PTEN), and PP1 Herbimycin (Src inhibitors) (see Boosani et al Expert Opin Ther Pat. 2013 May; 23(5):569-580.)

In some embodiments, the therapeutic agent is an inhibitor of the TGF-beta pathway. TGF-beta is a protein known to be involved in several normal tissue toxicity effects including lung fibrosis. Bone morphogenic proteins (BMPs) are members of the TGF-beta superfamily, and the BMLP pathway is downregulated following Flash treatment. Flash treated mice also exhibited reduced lung fibrosis compared to mice treated with conventional radiation. Thus, in some embodiments, flash radiation therapy is combined with an inhibitor of the TGF-beta pathway, such as a small molecule inhibitor (e.g., SD-208, LY2109761, LY21157299) or an antibody or fragment thereof that binds TGF-beta.

In some embodiments, the therapeutic agent is an activator or inducer of Type 1 interferons (IFNs), which influence the development of innate and adaptive immune responses. The IFN signaling pathway was downregulated in FLASH treated animals when compared to conventional radiation treatment. Type 1 interferons modulate innate immune responses in a balanced manner that promotes antigen presentation and natural killer cell functions while restraining pro-inflammatory pathways and cytokine production. Type 1 interferons also activate the adaptive immune system, promoting the development of high-affinity antigen-specific T and B cell responses and immunological memory. Type 1 interferons in the microenvironment promote the maturation and antigen presentation of DCs and boost endogenous NK or CD8+ T-cell mediated antitumor immune responses. Thus, in some embodiments, flash radiation therapy is combined with an activator or inducer of Type 1 interferons, which is expected to create an environment in which immune cells, including T-cells, can eradicate tumor cells.

In some embodiments, the activator or inducer of Type 1 interferons is an activator of the STING/cGAS pathway. Activators of the STING/cGAS pathway include, synthetic CDN STING agonists, small molecule STING agonists, small molecule STING pathway agonists, viruses encoding STING pathway agonists, bacteria encoding STING pathway agonists, or STING agonist encapsulated nanoparticles and liposomes. In some embodiments, the interferon activator includes compounds that bind and activate Toll-like receptors (TLR) such as TLR4 and TLR9, and compounds that active the MAVS pathway.

In some embodiments, the therapeutic agent is an activator of Dendritic Cell (DC) maturation. As described herein, DC maturation is down-regulated following FLASH treatment. Regulation of phagocytic functions in dendritic cells, and thereby antigen processing and presentation by innate signaling, represents a critical level of integration of the adaptive and innate immune systems. Thus, in some embodiments, flash radiation therapy is combined with an activator of DC maturation, such as a synthetic peptide vaccine.

Furthermore, inhibitors of CD47/SIRP-alpha can be used to enhance antigen-cross presentation by dendritic cells and increased T-cell priming. Thus, in some embodiments, flash radiation therapy is combined with an inhibitors of CD47/SIRP-alpha, such as, among others, antibodies, antibody derivatives or fragments therof, and compounds or small molecules that inhibit the CD47/SIRP-alpha interaction.

In some embodiments, the therapeutic agent is an Aryl Hydrocarbon Receptor (ahR) inhibitor. In some embodiments, flash radiation therapy is combined with an ahR inhibitor, such as SR1, CH-223191, UM729, or Galangin.

Immune Modulators

The FLASH radiation therapy described herein can be administered in combination with one or more immune modulators. The combination therapy can provide an increased anti-tumor response (a positive clinical response) compared to administration of either treatment as monotherapy. In some cases, the immune modulator can be selected from the group consisting of an inhibitor to an inhibitory checkpoint molecule, an activator of a stimulatory checkpoint molecule, a chemokine inhibitor, an inhibitor of macrophage migration inhibitory factor (MIF), a growth factor, a cytokine, an interleukin, an interferon, an antibody that binds to an immune system cell, such as a bispecific antibody that binds to T-cells and a tumor antigen, a cellular immune modulator such as a CAR-T cell, a vaccine, an oncolytic virus, and any combination thereof.

Immune modulators can include small molecules and biologic therapies (e.g., antibodies, fragments thereof, and derivatives thereof) that bind molecules expressed on the surface of immune system cells, such as antigen presenting cells and T-cells. Biologic therapies can also include bispecific antibodies, fragments thereof, and derivatives thereof that bind to both antigen presenting tumor cells and T-cells. Immune modulators also can include small molecules that inhibit or stimulate the immune system. In some instances, the immune modulator stimulates CD27+ immune cells, or inhibits one or more inhibitory checkpoint molecule(s) including PD-1, PD-L1, PD-L2, CTLA-4, BTLA, A2aR, B7-H2, B7-H3, B7-H4, B7-H6, CD47, CD48, CD160, CD244 (2B4), CHK1, CHK2, CGEN-15049, ILT-2, ILT-4, LAG-3, VISTA, gp49B, PIR-B, TIGIT, TIM1, TIM2, TIM3, TIM4, KIR, and ligands thereof, and others. Immune checkpoint pathways and signaling molecules are described in, e.g., Pardoll, *Nature Rev Cancer,* 2012, 12:252-264; and Mellman et al., *Nature,* 2011, 480:480-489.

An inhibitor of an inhibitory checkpoint molecule can be an antibody or fragment thereof that specifically binds or recognizes PD-1, PD-L1, PD-L2, CTLA-4, BTLA, A2aR, B7-H2, B7-H3, B7-H4, B7-H6, CD47, CD48, CD160, CD244 (2B4), CHK1, CHK2, CGEN-15049, ILT-2, ILT-4, LAG-3, VISTA, gp49B, PIR-B, TIGIT, TIM1, TIM2, TIM3, TIM4, KIR, and ligands thereof. In some embodiments, the CTLA-4 inhibitor is selected from the group consisting of ipilimumab, tremelimumab, and the like. One non-limiting example of a small molecule immune modulator is an inhibitor of the enzyme indolamine 2,3-dioxygenase (IDO). In some embodiments, the immune modulator is an inhibitor of PD-1, PD-L1, PD-L2, or CTLA-4.

In some embodiments, the PD-1 inhibitor is selected from the group consisting of pembrolizumab, nivolumab, lambrolizumab, pidilizumab, AMP-244, MEDI-4736, MPDL328 OA, MIH1, IBI-308, mDX-400, BGB-108, MEDI-0680, SHR-1210, PF-06801591, PDR-001, GB-226, STI-1110, biosimilars thereof, biobetters thereof, and bioequivalents thereof. In some embodiments, the PD-L1 inhibitor is selected from the group consisting of durvalumab, atezolizumab, avelumab, BMS-936559, ALN-PDL, TSR-042, KD-033, CA-170, STI-1014, KY-1003, biosimilars thereof, biobetters thereof, and bioequivalents thereof.

In some embodiments, the activator of the stimulatory checkpoint molecule is a small molecule, antibody or a fragment thereof, a polypeptide-based activator, a polynucleotide-based activator (i.e., an aptamer), agonist, agonist antibody or fragment thereof, and the like. The stimulatory checkpoint molecule can be B7-1 (CD80), B7-2 (CD86), 4-1BB (CD137), OX40 (CD134), HVEM, inducible costimulator (ICOS), glucocorticoid-induced tumor necrosis factor receptor (GITR), CD27, CD28, CD40, or a ligand thereof.

In some embodiments, a chemokine inhibitor is administered as an immune modulator. The chemokine inhibitor can be a small molecule, or antibody or fragment thereof that specifically binds to the chemokine (or its receptor) and inhibits its activity. In some embodiments, the chemokine is selected from the group consisting of CCL2, CCL3, CCL4, CCL5, CCL7, CCL8, CCL11, CCL12, CCL13, CCL14, CCL15, CCL16, CCL17, CCL18, CCL19, CCL20, CCL21, CCL22, CCL23, CCL24, CCL5, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL5, and CXCL16, or any other chemokine that is associated with cancer such as trafficking leukocytes into the tumor microenvironment (e.g., control leukocyte infiltration to the tumor). In some embodiments, the chemokine inhibitor binds to a chemokine receptor selected from the group consisting of CCR1, CCR2, CCR3, CCR, 4, CCR5, CCR6, CCR7, CCR8, CCR9, CCR10, CXCR1, CXCR2, CXCR3, CXCR4, CXCR5, CXCR6, and CXCR7.

Additional examples of an immune modulator include but are not limited to an anti-TIM4 antibody, an anti-MFG-E8 antibody, an anti-M199 antibody, any combination thereof, and the like. In some embodiments, the immune modulator includes agents (antibodies or small molecules) involved in priming and activation of the immune systems, and includes agents targeting CTLA4, B7 (B7-1 or B7-2), PD-L1/PD-L2, or PD-1, or agents targeting the binding interactions between CTLA4 and B7-1/B7-2, or PD-1 and PD-L1/PD-L2. Agents targeting CTLA4, B7 (B7-1 or B7-2), PD-L1/PD-L2, and PD-1 include antibodies that specifically bind these molecules, such as monoclonal antibodies. In some embodiments, the agent is an antibody that specifically binds to LAG 3, TIM1, TIM3, MFG-E8, IL-10, or Phosphatidylserine.

The immune modulators described herein can be administered at therapeutically effective doses. Therapeutically effective doses can be determined by one of ordinary skill in the art based on the type of immune modulator administered. Dosage, routes of administration, and administration schedules described in the art can be used. Representative doses are available in the Merck Manual Professional Edition (see the internet at merckmanuals.com/professional).

Further, doses of immune modulators administered to animals can be converted to equivalent doses for humans based on the body surface area (BSA) (represented in mg/m2) normalization method (see, e.g., Reagan-Shaw, S. et al., "Dose translation from animal to human studies revisited," FASEB J. 22, 659-661 (2007); and "Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), July 2005, Pharmacology and Toxicology; which are incorporated by reference herein). For example, the human equivalent dose (HED) based on BSA is can be calculated by the following formula I:

I. HED=animal dose in mg/kg×(animal weight in kg/human weight in kg)0.33

Alternatively, the HED can be determined by the following formula II:

II. HED (mg/kg)=animal dose (mg/kg)×(animal Km/human Km)

The Km factor is determined based on the following Table (see Guidance for Industry, Id.):

TABLE X

| Conversion of Animal Doses to Human Equivalent Doses Based on Body Surface Area | | | |
|---|---|---|---|
| Species | To Convert Animal Dose in mg/kg to Dose in mg/m², Multiply by $k_m$ | To Convert Animal Dose in mg/kg to HED[a] in mg/kg, Either: Divide Animal Dose By | Multiply Animal Dose By |
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | 12 | 3.1 | 0.32 |
| Monkeys[c] | 6 | 6.2 | 0.16 |
| Marmoset | 7 | 5.3 | 0.19 |
| Squirrel monkey | 20 | 1.8 | 0.54 |
| Baboon | 27 | 1.4 | 0.73 |
| Micro-pig | 35 | 1.1 | 0.95 |
| Mini-pig | | | |

Assumes 60 kg human.

Thus, a 5 mg/kg dose in mice is equivalent to a 0.4 mg/kg dose in a 60 kg human. A 0.4 mg/ml dose in a 60 kg human is equivalent to a dose of 14.8 mg/m2.

In some embodiments, the immune modulators described herein are administered in therapeutically effective amounts for periods of time effective to treat a cancer or tumor. The effective amount of the immune modulators described herein can be determined by one of ordinary skill in the art and includes dosage amounts for a mammal of from about 0.5 to about 200 mg/kg, about 0.5 to about 150 mg/kg, about 0.5 to 100 mg/kg, about 0.5 to about 75 mg/kg, about 0.5 to about 50 mg/kg, about 0.01 to about 50 mg/kg, about 0.05 to about 25 mg/kg, about 0.1 to about 25 mg/kg, about 0.5 to about 25 mg/kg, about 1 to about 20 mg/kg, about 1 to about 10 mg/kg, about 20 mg/kg of body weight, about 10 mg/kg, about 5 mg/kg, about 2.5 mg/kg, about 1.0 mg/kg, or about 0.5 mg/kg of body weight of the immune modulator, or any range derivable therein. In some embodiments, the dosage amounts of the immune modulators are from about 0.01 mg/kg to about 10 mg/kg of body weight. In some embodiments, the dosage amount of the immune modulator is from about 0.01 mg/kg to about 5 mg/kg, or from about 0.01 mg/kg to about 2.5 mg/kg of body weight. The compositions described herein can be administered in a single dose or in the form of individual divided doses, such as from 1 to 4 times per day, or once every 2 days, 3 days, 4 days, 5 days, 6 days, weekly, or monthly. The compositions described herein can also be administered for various treatment cycles, such as 2, 3, 4, 5, 6, 7, 8, 9, 10 treatment cycles. The treatment cycles can be different lengths of time depending on the cancer to be treated, for example, 1, 2, 3, 4, 5, 6, 7, 8, 9, or 10 week treatment cycles. In addition, the effective amount of an immune modulator described herein can be determined during pre-clinical trials and clinical trials by methods known to physicians and clinicians.

EXAMPLES

The following examples are offered to illustrate, but not to limit, the claimed embodiments.

Example 1

This example provides results from a study comparing gene expression profiles and tissue damage in mice treated with Conventional and FLASH irradiation.

Microarray Methods:

Samples: C57BL/6 mice were either irradiated with Conventional proton dose rate (1 Gy/s), Flash Dose rate (40 Gy/s), Split Flash (total dose split into 10 equal parts, each fraction separated by a time period of 1 sec, instantaneous dose at the time of delivery is 40 Gy/s overall dose rate is 4 Gy/s). 392 age and sex matched mice were treated in 6 Cohorts and sacrificed 1 hr-36 wks after lung irradiation. 4 Groups in each cohort: Sham: no radiation; Conventional: 1 Gy/s; FLASH: 40 Gy/s beam on; Split-FLASH: 4 Gy/0.1 sec, pulsed delivery (see FIG. 5). Animals were euthanized either 24 hours, 8 weeks, 16 weeks or 24 weeks after radiation and lungs collected. For gene expression analysis a total of 96 lung samples (24 samples/timepoint) were taken, three male and three female each from four different treatment groups, i.e. Sham, Conventional 15 Gy, Flash 15 Gy and Split Flash 15 Gy.

RNA isolation and quality control: Total RNA was isolated using Qiagen RNasy Tissue microarray kit (Qiagen cat 74104). Briefly, frozen middle left lung from mice (20-30 mg) was homogenized in liquid nitrogen and RNA isolated using the manufacturers protocol. Integrity of the isolated RNA was assessed using the 2100 Bioanalyzer (Agilent technologies) and only samples with RNA integrity number of at least 7 or 28/18S ratio of 1.3 or higher were considered for further processing.

Sample amplification and labelling: Fluorescent Cy3 Labelling was done as recommended by Agilent Technologies using the One-Color Microarray-Based Gene Expression Analysis Low input Quick Amp Labeling. 100 ng RNA of each sample was amplified and labelled with the One-Color Microarray-Based Gene Expression Analysis Low input Quick Amp Labelling kit and 600 ng of Cy3 labelled cRNA was used for hybridization on each patch. Amplification and integration of Cy3 was measured using the Nanodrop and only samples having specific activity of above 8 were used further.

Gene-expression profiles were generated using the Sure-Print G3 Mouse Gene Expression v2 microarray 8×60K produced by Agilent Technologies (Palo Alto, CA, USA). Labeling and hybridization was performed following the manufacturer's protocol. Each sample was loaded in triplicate onto the Agilent array for a total of 72 slots. Then, 600 ng of Cy3-labeled cRNA was hybridized on the 8×60K arrays using Agilent's High-RPM Gene Expression Hyb Kit. Hybridization was performed for 20 hrs at 65° C. in a rotating hyb oven at 10 rpm. After washing, arrays were scanned using Innopsys 710 Innoscan. Resulting TIFF-images were processed using Innopsys Feature Extraction software Mapix.

Expression Profile pre-processing & normalization: After image extraction using Mapix software correlation analysis between technical replicates was conducted to identify any technical replicates which did not correlate with their sibling replicates. Any arrays that passed QC were consolidated into one file by calculating the median of each technical replicate's mean intensity and median background. Data files were analyzed using an R package Limma (Ritchie et al., 2015). After uploading data, mean fluorescent intensities arrays were quantile normalized to allow comparisons across different groups(Bolstad et al., 2003). In order to handle flagged spots a weight of 0 for all flags with values less than −50 was assigned. This ensured that during the linear fitting of the data that these points are not be considered for linear fitting.

Gene Set Enrichment Analysis (GSEA): After normalization data was used for GSEA analysis to identify enriched pathways in each treatment group (Subramanian et al., 2005). A classic GSEA analysis was run using the HALL-MARKS gene sets using probe level data between treatments groups and sham. For downstream analysis, pathways with FDR-q values less than 25% and corrected p-values less than or equal to 0.05 were considered for reporting and downstream purposes.

Differentially expressed genes analysis: To identify differentially expressed genes between treatment groups, Limma's package was used which implements a linear model fitting of the data and then uses a moderated T-Test to compare probes between comparison groups. To correct for multiple hypothesis testing p-values using Bonferroni-Hochberg method were adjusted and genes with adjusted p-value less than or equal to 0.05 for downstream analysis (Benjamini and Hochberg, 1995) were considered.

Ingenuity Pathway Analysis (IPA): Traditional analysis of the microarray data by generating a list of most regulated genes is not enough to understand the functions of the regulated genes and their roles in biological processes. Hence, molecular pathway analysis was also performed using IPA to predict what canonical pathways, upstream regulators and biofunctions were altered to identify the molecular events and further unveil the molecular mechanisms being regulated by altering the dose rate of radiation from 1 Gy/s to 40 Gy/s IPA searches through the gene list and determines genes that are involved in well documented canonical signal transduction or metabolic pathways.

IPA queries the Ingenuity Pathways Knowledge Base for interactions between the focused genes first and then all other gene objects stored in the knowledge base. For our data, genes that met the parametric P value of 0.05 were queried for IPA Core analysis followed by identification of major canonical pathways modulated. The significance of the association between the data set and the canonical pathway was determined based on two parameters: (1) A ratio of the number of genes from the data set that map to the pathway divided by the total number of genes that map to the canonical pathway and (2) a P value calculated using Fischer's exact test, followed by Benjamin Hotchberg correction (FDR cutoff value of ≤0.1) determining the probability that the association between the genes in the data set and the canonical pathway is due to chance alone 3) An absolute value cutoff of Z score 1.5 or above to predict the enrichment and activation status of a particular pathway. The pathways that met all these criterion were predicted to be significantly regulated.

TUNEL Methods:

TUNEL Fluorescence Staining: Apoptosis was determined by Terminal deoxynucleotidyl transferase dUTP nick end labeling (TUNEL) fluorescence staining using the In Situ Cell Death Detection Kit, Fluorescein (Sigma-Aldrich Corporation, Saint Louis, MO). Snap frozen lung tissues were sectioned 5 μm thick, then fixed, permeabilized, and stained according to the manufacturer's directions. Tissue sections were also treated with DAPI (NucBlue™ Fixed Cell ReadyProbes™ Reagent (Thermo Fisher Scientific, Waltham, MA), 2 drops per mL of PBS) as a counterstain. Images were acquired at 100× magnification with Immersion Oil, type LDF (Cargille-Sacher Laboratories Inc., Cedar Grove, NJ) using the DAPI and FITC channels on a Keyence BZ-X700 microscope (Keyence Corporation, Osaka, Japan).

Figure 22:
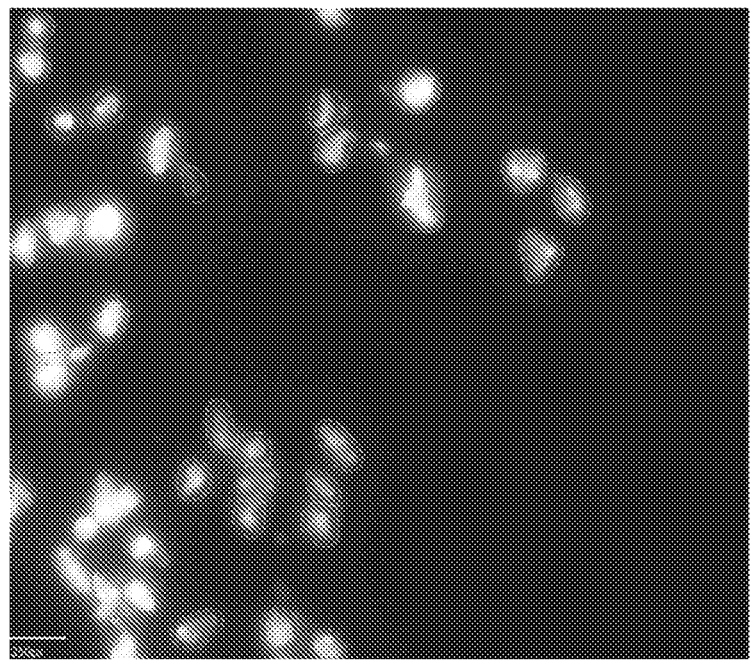
FIG. 22 shows the result of QuPath cell detection applied to a DAPI image.

Analysis: Several fields of view were imaged for each sample on a Nikon ECLIPSE Ni-E microscope (Nikon Corporation, Chiyoda, Japan) at 100× magnification with oil immersion in the DAPI and FITC fluorescent channels (nuclei and TUNEL respectively). These images were imported into QuPath (Bankhead, P. et al. QuPath: Open source software for digital pathology image analysis. Sci. Rep. 7, 16878 (2017)) and the watershed cell detection plugin was used to segment and count the nuclei in the DAPI channel (FIG. 22). Finally, the Fiji distribution of ImageJ (Rueden, C. T.; Schindelin, J. & Hiner, M. C. et al. (2017), "ImageJ2: ImageJ for the next generation of scientific image data", BMC Bioinformatics 18:529, doi:10.1186/s12859-017-1934-z); and Schindelin, J.; Arganda-Carreras, I. & Frise, E. et al. (2012), "Fiji: an open-source platform for biological-image analysis", Nature methods 9(7):676-682, PMID 22743772, doi:10.1038/nmeth.2019) was used to quantify the number of TUNEL positive cells in each field of view. A gaussian blur was first applied to the image, and then thresholding was used to segment the cells (FIGS. 23A and 23B).

Figure 6:
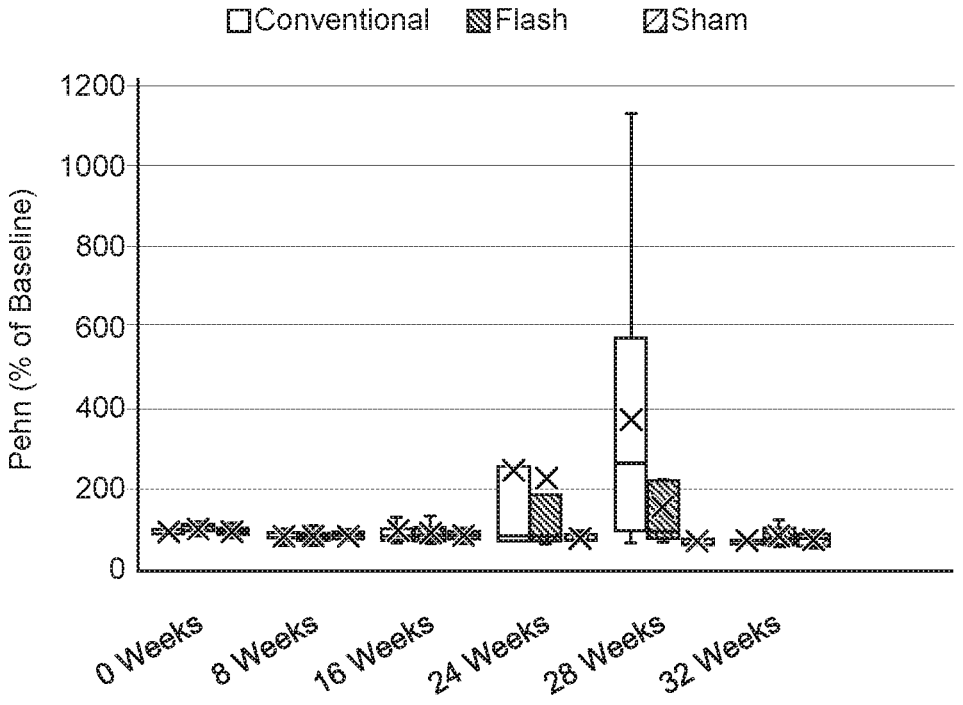
FIG. 6 shows improved lung function for FLASH when compared to Conventional radiation treatment.

Lung Function: Lung and penh was evaluated using Whole Body Plethysmograph (Jackson et Health Physics 2014). A baseline measure of penh was taken and thereafter animals were monitored every 2 weeks for lung function. The results are shown in FIG. 6.

Figure 10:
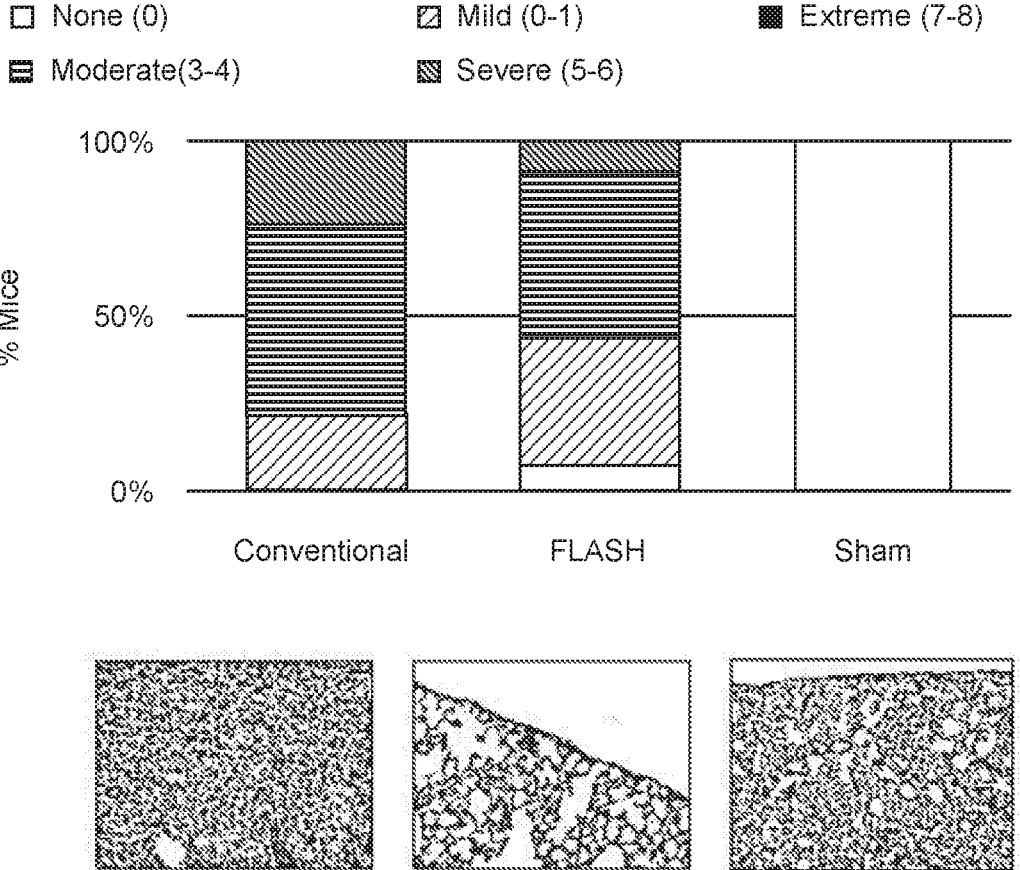
FIG. 10 shows a 23% reduction in average lung fibrosis severity for FLASH over Conventional group at 17.5 Gy.

Lung Fibrosis: Mice were either untreated or treated either conventional, Flash or split flash radiation. At various time points 16, 24 and 36 weeks the mice were euthanized, lung tissue was fixed in formalin and embedded in parafilm. The lung sections were stained with masson trichome and H&E stains and microscopic evaluation was performed by a trained pathologist who scored for fibrosis using the MF SS scoring scheme from 0-8 (Ashcroft Journal of Clinical Pathology 1988 and Hubner et al Biotechniques 2008), with 0 being no fibrosis and 8 corresponding to complete obliteration of the pulmonary architecture by severe fibrosis with complete loss of airspace (obliterative fibrosis). The results are shown in FIG. 10.

Figure 9:
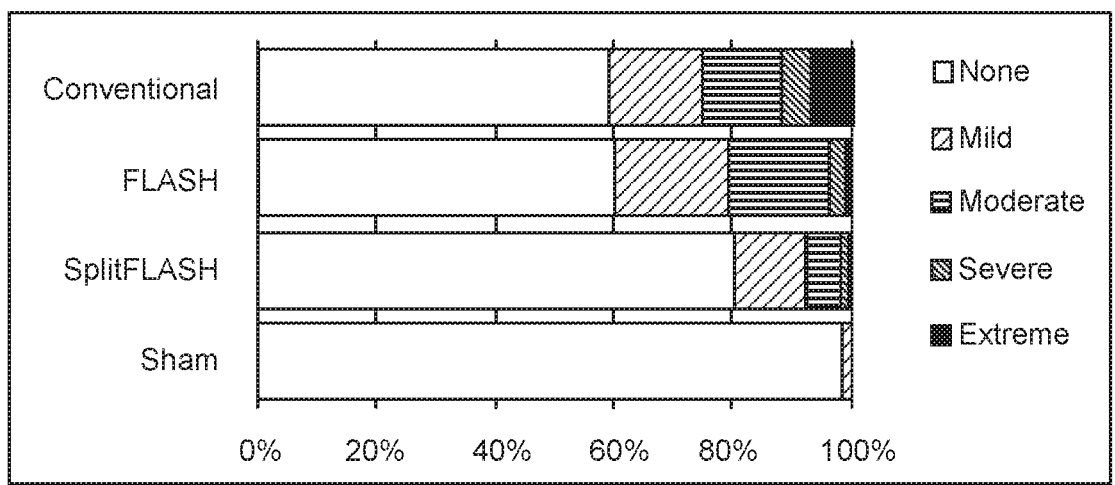
FIG. 9 shows a reduction in average dermatitis for FLASH when compared to Conventional radiation: FLASH: 34% reduction; Split-FLASH: 52% reduction.

Dermatitis in the mice was scored by using the Douglas and Fowler scale. The scoring was done between 0 and 3.5, with 0 being normal and 3.5 being moist desquamation in most of the irradiated area along with necrosis (Ryan et al Journal of investigative Dermatology 2012). The results are shown in FIG. 9.

Figure 8:
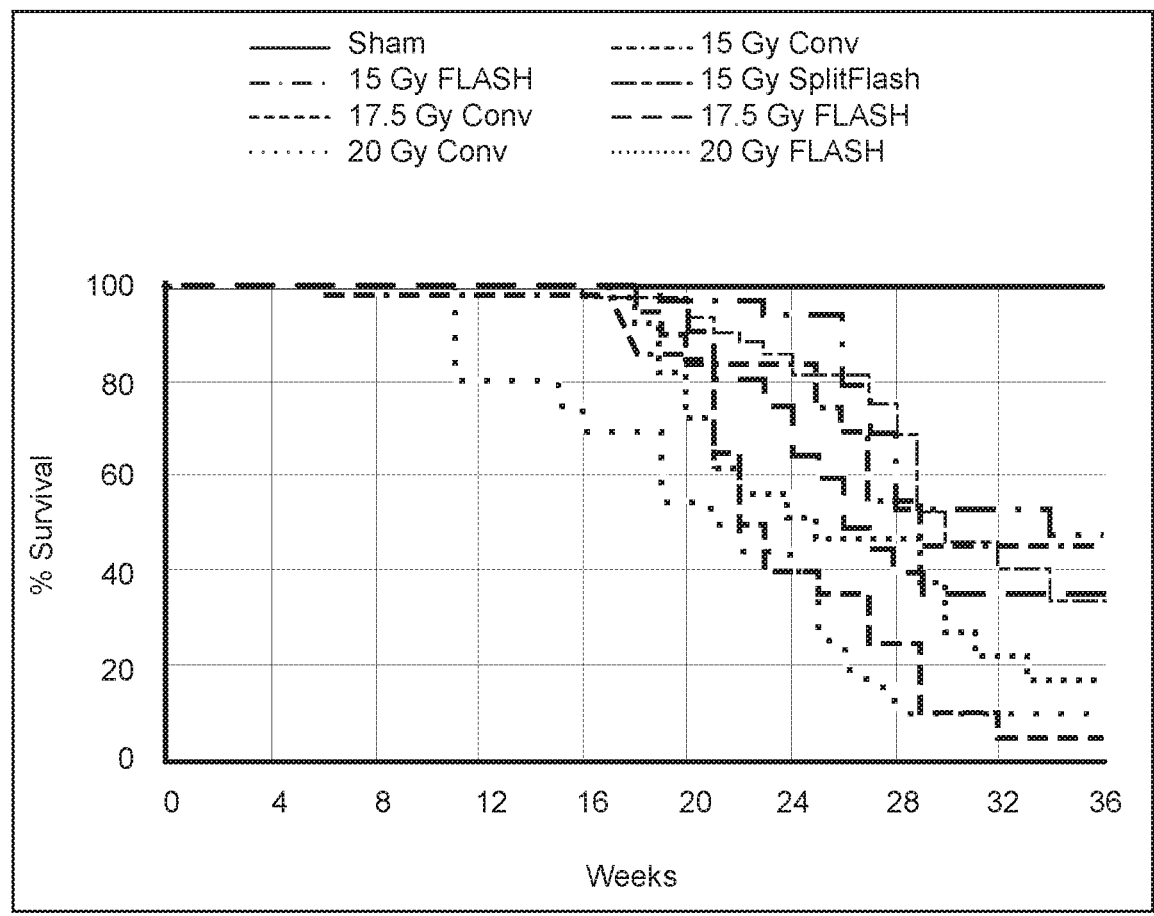
FIG. 8 shows an improved median survival for FLASH over Conventional radiation treament groups and the potential for a therapeutic window that is dose rate dependent: 17.5 Gy FLASH>17.5 Gy CON; 17.5 Gy FLASH=20.0 Gy CON.

Survival: Mice were treated with 15, 17.5 and 20 Gy of conventional or Flash radiation dose. Each radiation dose group was composed of 20 age-matched animals (50% male and 50% female). Animals were monitored thrice weekly and euthanized if there was more than 20% body weight loss with no recovery within 2 days or severe dermatitis as scored by a veterinarian. The results are shown in FIG. 7 and FIG. 8.

Results:

Lung Function is Improved and Fibrosis is Decreased Using FLASH Radiation

Figure 11:
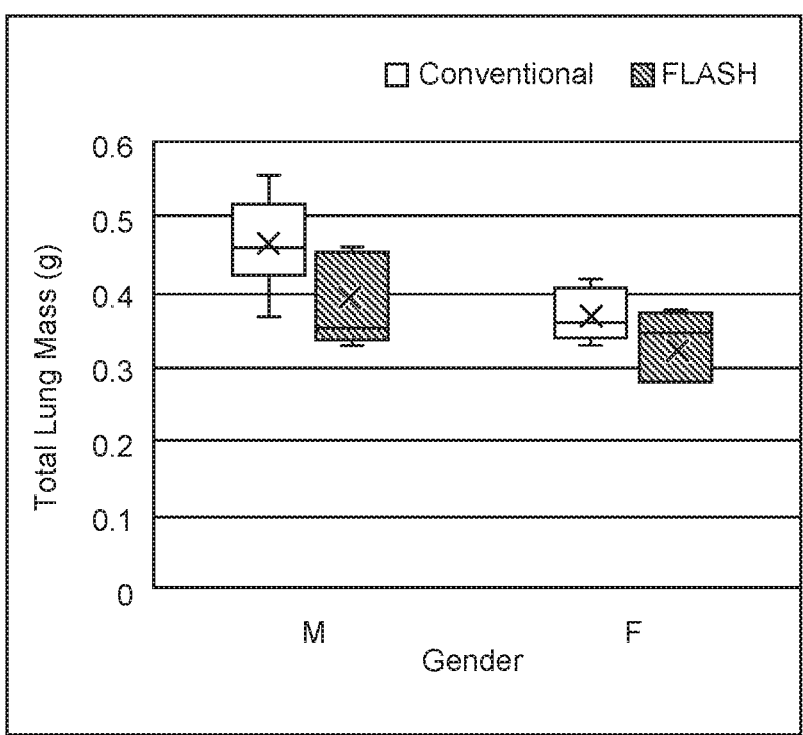
FIG. 11 shows an increased average lung weight for Conventional when compared to FLASH treatment—0.46 g vs. 0.40 g (M); 0.37 g vs. 0.32 g (F)).
Figure 19:
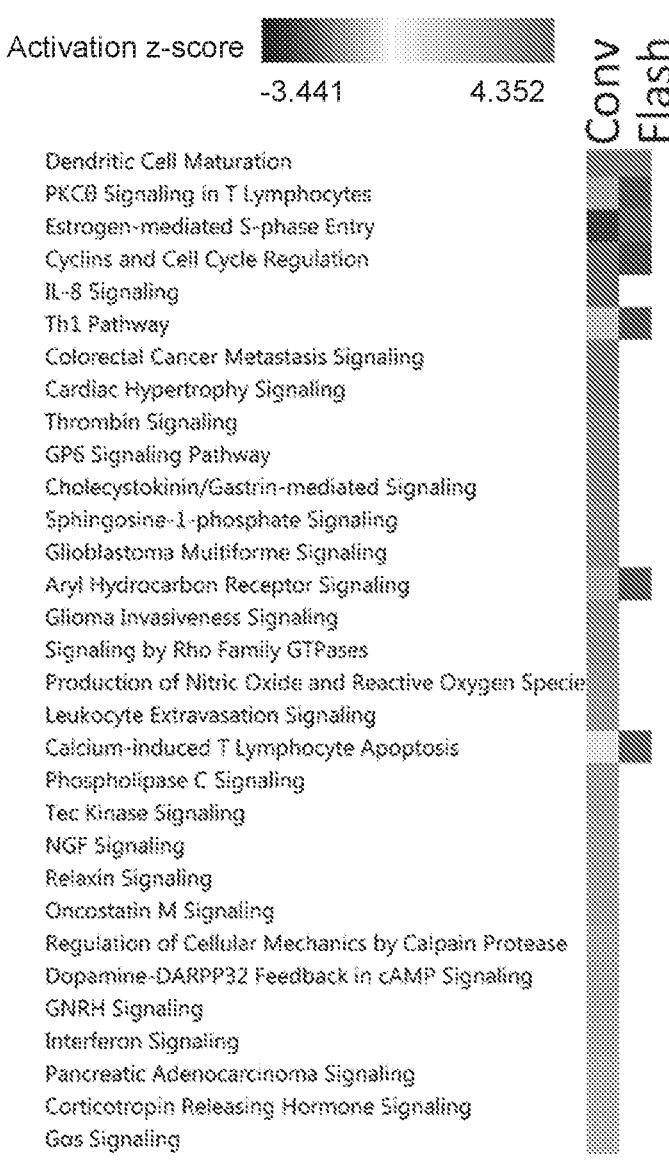
FIG. 19 shows a heat map of comparative analysis of major canonical pathways regulated by both Flash and Conventional radiation treatment as analyzed by IPA. P value 0.05 and Z score of >1.5. pathways found to be differentially regulated between these treatment regimens were mostly involved in inflammation and immune regulation.
Figure 20:
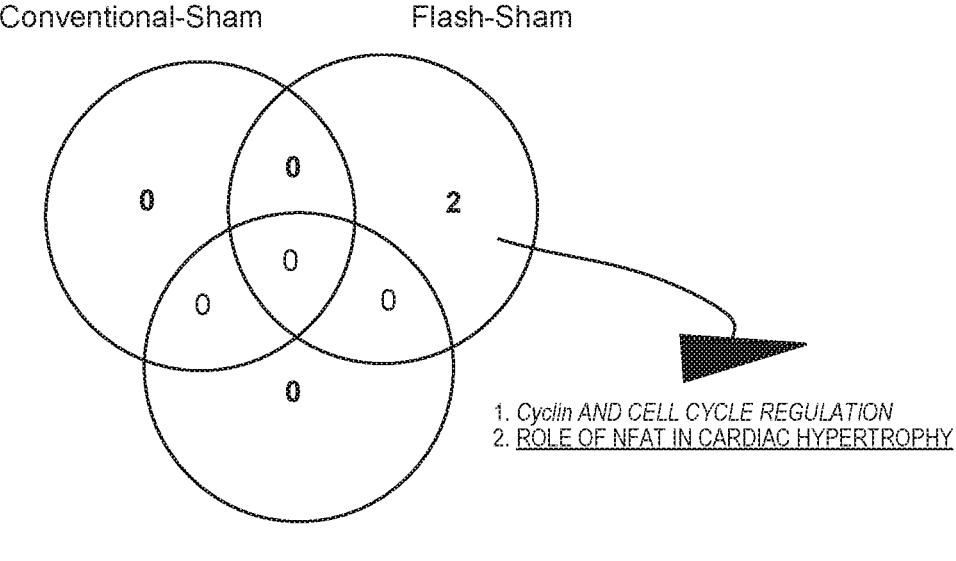
FIG. 20 shows a pie chart representing various canonical pathways found to be regulated by different radiation regimens at 16 weeks. Analysis was done on filtered list of genes having p value of <0.05. samples. Pathways presented her and listed in Table 1 are have p value<0.05, FDR<0.1 and Z score of >1.5. Underlined text denotes downregulated while italicized text denotes upregulated pathways relative to Sham treated samples.)
Figure 21:
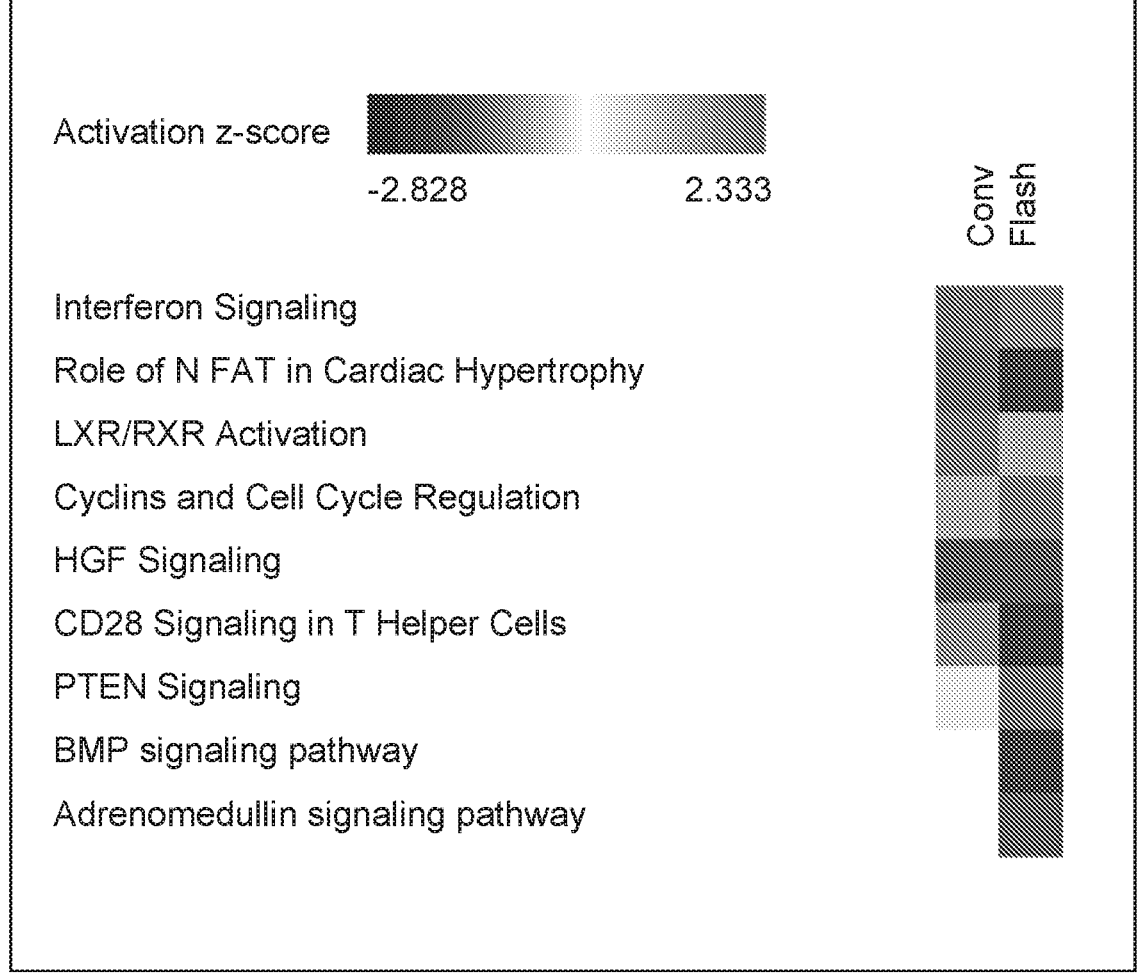
FIG. 21 shows a heat map of comparative analysis of major canonical pathways regulated by both Flash and Conventional radiation treatment at 16 weeks as analyzed by IPA. P value 0.05 and Z score of >1.5. pathways found to be differentially regulated between these treatment regimens were mostly involved in inflammation and immune regulation.

FIG. 6 shows improved lung function for FLASH when compared to Conventional radiation treatment. This difference confirms the presence of dose rate dependence of radiation toxicity. FIG. 10 shows a 23% reduction in average lung fibrosis severity for FLASH over Conventional group at 17.5 Gy. This difference confirms the presence of dose rate dependence of radiation toxicity. FIG. 11 shows an increased average lung weight for Conventional when compared to FLASH treatment—0.46 g vs. 0.40 g (M); 0.37 g vs. 0.32 g (F)). This study indicates normal tissue sparing for FLASH.

Survival of Mice is Increased After Irradiation with FLASH Compared with Conventional Radiation FIG. 7 shows an improved median survival for FLASH over Conventional radiation treament groups: 20.0 Gy: 14% increase; 17.5 Gy: 18% increase. FIG. 8 shows an improved median survival for FLASH over Conventional radiation treament groups and the potential for a therapeutic window that is dose rate dependent: 17.5 Gy FLASH>17.5 Gy CON; 17.5 Gy FLASH=20.0 Gy CON.

FLASH Decreases Dermatitis Compared with Conventional Radiation

FIG. 9 shows a reduction in average dermatitis for FLASH when compared to Conventional radiation: FLASH: 34% reduction; Split-FLASH: 52% reduction. This difference confirms the presence of dose rate dependence of radiation toxicity related to dermatitis.

Microarray:

Flash Radiotherapy (FLASH RT) Modalities Synergize with Mitotic Spindle Inhibitors FIG. 12 shows Venn Diagrams of Differentially Expressed genes at each time point. GSEA at 24 hours revealed G2M checkpoint and E2F Targets were repressed by all radiotherapy modalities (FIG. 13A). These signatures suggest that cells are arresting at G1 and G2M post treatment. E2F targets include a broad range of genes; however, cyclins are major targets for this pathway {cite}. Therefore, the use of Flash RT in combination with CDK4/6 inhibitor (Pablociclib) may sustain cell cycle arrest caused by radiotherapy.

The mitotic spindle was specifically downregulated in both flash and split flash groups (FIG. 14A, 14B). An overlap analysis of the core enrichment genes for each group shows that key regulators of mitotic spindle genes were downregulated such as AURKA, Kinesin-Like protein family genes (KIF11, KIF23, KIF23, KIF4A) and TPX2 (FIG.

14C, 14D) Emerging evidence that AURKA and TPX2 play major roles in driving acquired resistance in the context of several targeted therapies (Donnella et al., 2018; Panicker et al., 2017). In these models AURKA expression increases to drive drug resistance, thus blocking AURKA expression may be important for the efficacy of Flash and Split Flash therapies. Specifically targeting AURKA with small molecule inhibitors (Alisertib, Tozasertib). TPX2 is a driver of AURKA and blocking TPX2-AURKA complexes using a complex disruptor (GSK1070916) (Asteriti et al., 2015; Janeček et al., 2016) is indicated. Finally, mitotic spindle integrity can be targeted by using Taxanes (Docetaxel, Paclitaxel). At the end of 24 weeks, FLASH RT upregulated Mitotic Spindle genes (FIG. 13D), in support that adaptive gene expression changes may play a critical role to the efficacy of radiotherapy.

Flash RT Modalities Combinations with DNA Damage Repair & Response Inhibitors

Flash RT specifically repressed DNA repair pathways genes. At the pathway level Flash RT downregulated the Hallmark DNA Repair pathway (FIGS. 13A & 15A). Core enrichment analysis reveals the downregulation of key Homology Directed Repair (HR) genes such as LIG1, RAD51, and BRCA2 (FIG. 15B for full list). The immediate implication of these downregulated genes suggest that flash therapy induces a BRCAness phenotype, therefore targeting tumors with PARP inhibitors (Talazoparib, Rucaparib, Olaparib) in combination with FLASH RT (Lord and Ashworth, 2016; Murai et al., 2012) may be indicated.

Additionally, in the context of inhibited DNA repair (i.e. BRCA1 mutations, or BRCAness) the DNA damage response is blocked by blocking key regulators of this pathway. For example, RAD51 is required for the repair of double stranded breaks thus to the combination ofFLASH RT and RAD51 inhibitors (RI-1) may synergize. Additionally, targeting other DNA damage response kinases such as CHCK1 (AZD7762), ATM (KU-55933, KU-60019, NU7026, VE-821), ATR (NU7026), can also be effective in the context of flash RT induced BRCAness (Ashworth and Lord, 2018; Lord and Ashworth, 2016).

Flash RT in Combination with MAPK Pathway Inhibitors

Post 24 hrs, many pathways increase in expression (FIG. 13B-D), specifically KRAS Signaling upregulated across time in all treatment groups, specifically 'KRAS Signaling Up' was enriched in conventional and FLASH groups between 8-24 weeks (FIG. 16A-C). KRAS signaling is a major driver of cancer and drives many biological programs through the MAPK pathway including proliferation, cell cycle progressing and pro-survival signaling (Sun et al., 2015). There is evidence that conventional radiation therapy depends on blocking EGF/EGFR signaling (Wang et al., 2011). While direct inhibitor of RAS are still in early stages, the aim is to block up and downstream RAS signaling (Downward, 2003) using the combination of FLASH RT with inhibitors upstream and downstream of KRAS. As an example, upstream inhibitors such as, EGFR (Erlotinib, Gefitinib, Lapatinib, Afatinib) and SHP2 (RMC-4550) can be targeted in combination with FLASH RT. As another example, downstream inhibitors such as MEK (Trametinib, Selumetinib, PD0325901), BRAF (Dabrafenib, Vermurafenib, PLX-4720), or ERK (SCH772984, LY3214996, GDC-0994) can be combined with FLASH RT.

Radiotherapy Induced EMT

During the time course of 8-10 weeks Epithelial to Mesenchymal (EMT) Transition was an upregulated pathway in Flash between 8 to 16 weeks (FIG. 13B-C); however, at the end of 24 weeks EMT was upregulated in both Conventional and Flash Treatments (FIG. 17A-B). EMT is known to drive resistance to both targeted and non-targeted therapies and thus may pose a challenge to the efficacy of radiotherapy modalities (Kitai and Ebi, 2016; Liang et al., 2015). EMT is a consequence of gene expression changes that drive cells from one state to another, thus targeting EMT may pose a challenge. Overlap analysis of the EMT signature for Conventional and Flash at 24 hours reveals that there are a total of 56 genes overlapping (FIG. 17C, Table 1). Within the overlap TGFB1 and TGFBI, both were upregulated in conventional and flash treated mice. TGFB is a known driver of EMT and thus TGFB inhibitors (SD-208, LY2109761, LY21157299) may prevent EMT from occurring and give rise to radioresistant tumors (Foroutan et al., 2017)

Differential Gene Expression Analysis:

To get an assessment of early response to flash vs conventional treatment, microarray assessment was performed for irradiated mice euthanized 24 hrs post-irradiation. Initial cluster analysis reveals that for early time point Flash and sham samples cluster together while conventionally treated mice clustered with Split flash group. This follows the pattern initially seen with survival and dermatitis where Flash fared much better than conventional initially but later cluster closer to conventional treatment. Based on the gene expression analysis, at 24 hrs conventional irradiation (1 Gy/s) most significantly regulated 2131 genes (p value of 0.05) while Flash regulated only 257 genes at 24 Hr time point, out of these 175 common genes were regulated by both these radiation types (FIG. 5).

IPA Analysis:

IPA analysis revealed that many canonical pathways were altered by these different radiation treatment regimens. Major changes were observed at the initial time point of 24 hrs where most of the regulation at RNA level happens that is captured by the genome wide microarray. Most of the pathways significantly upregulated (p value≤I 0.05, Z score of ≤1.5 and FDR 0.1) in the conventional radiation were involved in inflammatory response like Interferon signaling, IL-8 signaling, STAT3 signaling, GP6 signaling pathway and phospholipase C signaling. Some cancer associated pathways were upregulated as well, like the pancreatic adenocarcinoma signaling and colorectal cancer metastasis signaling. Cyclin and cell cycle regulation pathway was predicted to be inhibited after conventional irradiation. (FIG. 18 and Table 6A-C). At 24 hrs for Flash radiation most of the pathways were downregulated and that included Mitotic roles of polo-like kinases, estrogen-mediated S phase entry, Aryl hydrocarbon receptor signaling, cyclin and cell cycle regulation, TH1 for helper T cells pathway, dendritic cell maturation and Calcium induced T lymphocyte apoptosis. In the split flash pathways regulated mostly involved cell cycle with distinct phases of cell cycle been modulated differentially along with the p53 pathway. The common pathway modulated by all the treatment types was Cyclin and cell cycle regulation, that is known to be disrupted after radiation treatment.

When comparison between conventional and Flash radiation was performed (p value of overlap>0.05 and Z score of 1.5), few pathways were shown to be differentially regulated between these treatments (FIG. 18). Dendritic cell maturation, PKC signaling in lymphocytes, TH1 pathway and calcium-induced T lymphocyte apoptosis was shown to go up after conventional radiation and down after Flash treatment. While many pathways were significantly upregulated after conventional radiation and unaffected after Flash radiation like IL-8, production of ROS and MO in macrophages, interferon signaling, Rho family GTPases, GP6 signaling, colorectal cancer metastasis signaling, Sphingosine-1-phosphate signaling etc.

TH1 Pathway: T helper type 1 (Th1) cells are a subset of CD4+ effector T cells and play a key role in immune response as well as cancer immunotherapy. Th1 subtype are involved in activating antigen presenting cells (APCs) and also of recruitment of macrophages or mast cells to the tumor site[1]. They are also involved in direct activation of cytokines in the tumor microenvironment that can lead to enhanced tumor cell kill[2]. This pathway was found to be inhibited by Flash compared to untreated mice, therefore flash radiation and immunotherapy combinations will work more effectively when combined with adjuvants that induce Th1 activity. The adjuvants to be used in combination with FLASH delivery include but are not limited to 1) cytokines associated with Th1 activation such as IL-12, IFN-alpha, beta or gamma, IL-2, IL-18, IL-27, CD80 (drug target abatacept, beletacept, galaximab), ICAM1 and TNF-alpha [3]; 2) Toll-like receptor agonist for TLR4 and TLR9 such as monophosphoryl lipid A and Bacillus Calmette-Guerin, Agatolimod, ISS-1018, HYB2055, and MGN1703; 3) STAT3 modulators like danvatirsen and OPB-31121; 4) Live bacteria (such as *Listeria monocytogenes*) or intracellular parasites (such as *Leishmania major* and *Toxoplasma gondii*), or compounds derived therefrom that trigger interferon gamma or IL-12 production, Bacterial lipopolysaccharide, killed *Mycobacterium tuberculosis*, bacterial superantigens such as staphylococcus enteroxin B and unniethylated CpG nucleotides that activate Th1 response in the body[4].

Calcium-mediated T cell apoptosis: One important pathway through with T cells undergo apoptosis is through calcium channel involving binding of MHC-class II complex on Antigen Presenting Cells to the TCR-CD3 complex on T cells, that leads to activation of PLC-gamma1 which in turns activate PKC and accumulation of calcium in the cytosol. The free calcium through interaction with calcineurin, CABIN and NFAT triggers an apoptotic pathway. This pathway was downregulated after Flash and was activated by conventional irradiation. Therefore, Flash radiation may spare T lymphocytes both by nature of its being quicker treatment modality (higher dose rate) that avoids irradiating more blood and also through downregulation of this pathway thus leading to molecular sparing of T lymphocytes. Lymphocytes are considered an organ-at-risk during radiation therapy and many organs with a high blood flow like lungs and brain have to be limited in dose to reduce lymphocyte killing[5]. Thus, Flash radiation in combination with treatment planning algorithms can be used to treat organ sites with a high lymphocyte count. This lymphocyte sparing will also have implications in providing effective immunotherapy combinations with radiation.

For 16-week analysis, two canonical pathways were found to be significantly modulated in the flash grp. The cyclin and cell cycle regulation pathway was activated while the NFAT pathway in cardiac hypertrophy was downregulated (p value≤I 0.05, Z score of ≥1.5 and FDR 0.1). In comparative analysis between Conventional 15 Gy and Flash 15 Gy radiation using Fischer exact statistical analysis (p value≤I 0.05 and Z score of ≥1.5) many pathways were found to be regulated by both the treatments. Interferon signaling was found to be upregulated in both through was found to be more activated in the conventional grp (FIG. 18). BMP signaling pathway was found to be downregulated in Flash vs Conventional.

PTEN: Phosphatase and tensin homolog (PTEN) pathway that is protective for carcinogenesis was activated in Flash, therefore predicting that maybe perhaps Flash can have protective effects on tissue compared to conventional. Loss of PTEN expression in mouse fibroblast was shown to result in lung fibrosis (Parapuram et al, Matrix Biol 2015). PTEN knockout mice treated with bleomycin (radio-mimetic drug) showed increased lung fibrosis. Because reduced lung fibrosis was Observed in Flash vs conventional radiation treatment (FIG. 10), one of the mechanisms through which Flash results in reduced lung fibrosis could be through the activation of PTEN pathway. Activators/agonists of the PTEN pathway are described in US 2011/0189169 A1, and include mTOR inhibitors such as rapamycin (Rapamune®, sirolimus, ATC code L04AA10 commercially available from Wyeth) and its chemical analogues such as CCI-779 (temsirolimus, Anatomical Therapeutic Chemical (ATC) code L01XE09, commercially available from Wyeth), RAD-001 (everolimus, ATC code L04AA18. commercially available from Novartis) and AP-2357 (Granville et al., Clin. Cancer Res. 12:679, 2006, which is herein incorporated by reference). Additional Activators of PTEN activity include Ublituximab, Rituximab, Sunitinib, (Induces PTEN), Trastuzumab and Pertuzumab (Increases PTEN through Src inhibition), Resistin (p38 MAPK modulator, increases PTEN), Simvastatin (NF0-kB inhibitor), Lovastatin and Rosiglitazone (PPAR-gamma modulators), NVP-AEW541 (IGF-1R modulator that increases PTEN), and PP1 Herbimycin (Src inhibitors) (see Boosani et al Expert Opin Ther Pat. 2013 May; 23(5): 569-580.)

BMP pathway: Bone morphogenic proteins (BMPs) are members of the TGF-beta superfamily. TGF-beta is a protein known to be involved in several normal tissue toxicity effects including lung fibrosis. The BMP pathway was downregulated at 16 week time point in the Flash treatment group. Flash treated samples also exhibited reduced lung fibrosis at 16 and 24 week time points. Therefore, inhibiting the TGF-beta pathway may reduce normal tissue toxicity.

Interferon Signaling:

Type 1 interferons (IFNs) influence the development of innate and adaptive immune responses. One of the most dysregulated canonical pathways, the IFN signaling pathway, was downregulated in FLASH when compared to CONY. Type 1 interferons modulate innate immune responses in a balanced manner that promotes antigen presentation and natural killer cell functions while restraining pro-inflammatory pathways and cytokine production. Type 1 interferons also activate the adaptive immune system, promoting the development of high-affinity antigen-specific T and B cell responses and immunological memory. Type 1 interferons in the microenvironment promote the maturation and antigen presentation of DCs and boost endogenous NK or CD8+ T-cell mediated antitumor immune responses. Thus, type 1 interferon activators can be used in combination with FLASH delivery to create an environment in which immune cells, including T-cells, can thrive to eradicate tumor cells.

One key pathway involved in the production of type 1 interferons is the STING/cGAS pathway. Stimulator of interferon genes (STING) is an intracellular signaling molecule that senses cyclic dinucleotides (CDNs). CDNs are derived from infectious agents exogenously, or are produced by the mammalian dsDNA sensor cGAS (cyclic guanosine monophosphate-adenosine monophosphate; cyclic GMP-AMP synthase). The STING/cGAS sensing mechanism induces innate immune responses including the production and release of type 1 interferons. Thus, activators of the STING/cGAS pathway can be used in combination with FLASH delivery to create an environment in which immune cell can thrive to eradicate tumor cells. These activators include, among others, synthetic CDN STING agonists, small molecule STING agonists, small molecule STING pathway agonists, viruses encoding STING pathway agonists, bacteria encoding STING pathway agonists, or STING agonist encapsulated nanoparticles and liposomes. Other type 1 interferon activators include compounds that bind and activate Toll-like receptors (TLR) such as TLR4 and TLR9, and compounds that active the MAVS pathway.

Dendritic Cell Maturation:

Dendritic cell maturation is down-regulated in FLASH. Regulation of phagocytic functions in dendritic cells, and thereby antigen processing and presentation by innate signaling, represents a critical level of integration of the adaptive and innate immune systems. Combination of FLASH and synthetic peptide vaccines could be beneficial to induce long-lasting immune responses.

Furthermore, inhibitors of CD47/SIRP-alpha can be used enhance antigen-cross presentation by dendritic cells and increased T-cell priming. These include, among others, antibodies, antibody derivatives and small molecules inhibiting the CD47/SIRP-alpha interaction.

Nanoparticles:

Nanoparticles are small particles between 1 and 100 nm in size. They can have different shapes such as spheres, rods, or stars. They can be passively targeted to tumors through the enhanced permeability and retention effect or actively targeted, such as by conjugating antibodies or peptides to the nanoparticles. Furthermore, they can be encapsulated in vesicles or inserted into gel matrices to increase tumor targeting.

It has been previously shown that nanoparticles with a high effective atomic number, such as gold or gadolinium, can have a synergistic effect when administered prior to radiotherapy by providing a dose enhancement (Hainfeld et al., 2004). This is because when hit by photons, the photoelectric effect occurs in the nanoparticles, whereby electrons and additional x-rays are emitted. Furthermore, radiation of nanoparticles can also cause hyperthermia in the tumor, increasing the treatment efficacy. It has also been shown that a dose enhancement can be achieved when using nanoparticles in conjunction with proton therapy (Lin, et al. 2014). Finally, radiation can also be used to modulate and enhance the delivery of nanoparticles to the tumor by altering the tumor microenvironment, such as by reducing the tumor interstitial pressure (Stapleton et al., 2017).

Flash RT Can be Used in Conjunction with Nanoparticles

One of the main hurdles of using nanoparticles in conjunction with radiotherapy is that nanoparticles can have a short half-life in the body. It is also challenging and impractical to deliver nanoparticles before each of several treatments in a traditional fractionated schedule. In addition, some nanoparticles can be toxic in high enough concentrations, especially when not quickly cleared from the body. These challenges can be overcome by using nanoparticles in conjunction with Flash RT. By treating the tumor or tumors in only a single fraction, the nanoparticle concentration in the tumor or tumors could remain high enough throughout the entire treatment, even if the nanoparticles had a relatively short half-life. Furthermore, because nanoparticles with a short half-life would still be effective, possible toxicity would be reduced as the nanoparticles would be cleared from the body quickly. One example of a workflow for Flash RT in conjunction with nanoparticles, is the administration of nanoparticles followed by imaging, such as by CT or MM. These imaging data are used to create a Flash RT treatment plan, considering the distribution of the nanoparticles. Then, prior to treatment, nanoparticles are reinjected and the planned Flash treatment delivered.

Aryl Hydrocarbon Receptor Pathway:

The Aryl Hydrocarbon Receptor (ahR) Signaling pathway was downregulated in Flash treated lungs. The general function of this pathway is to detect aromatic (aryl) hydrocarbons and activate a suite of xenobiotic-metabolizing genes, specifically cytochrome P450 enzymes. This has major implication for drug combination strategies as the downregulation of this pathway may alter the clearance of other drugs in a patient. Additionally, the activation of this pathway may also promote pan drug resistance to small molecules or the cell's ability to process toxic agents due to radiotherapy. AhR pathway activation has also been associated with cancer immunotherapy, AhR regulates both innate and adaptive immunity, it activates anti-inflammatory Treg cells and M2 macrophages. Therefore the combination of FLASH RT with ahR inhibtors (such as SR1, CH-223191, UM729, Galangin) may suppress the tumors ability to clear toxic agents and activate immune cells.

Apoptosis in Lung Tissue

Figure 24:
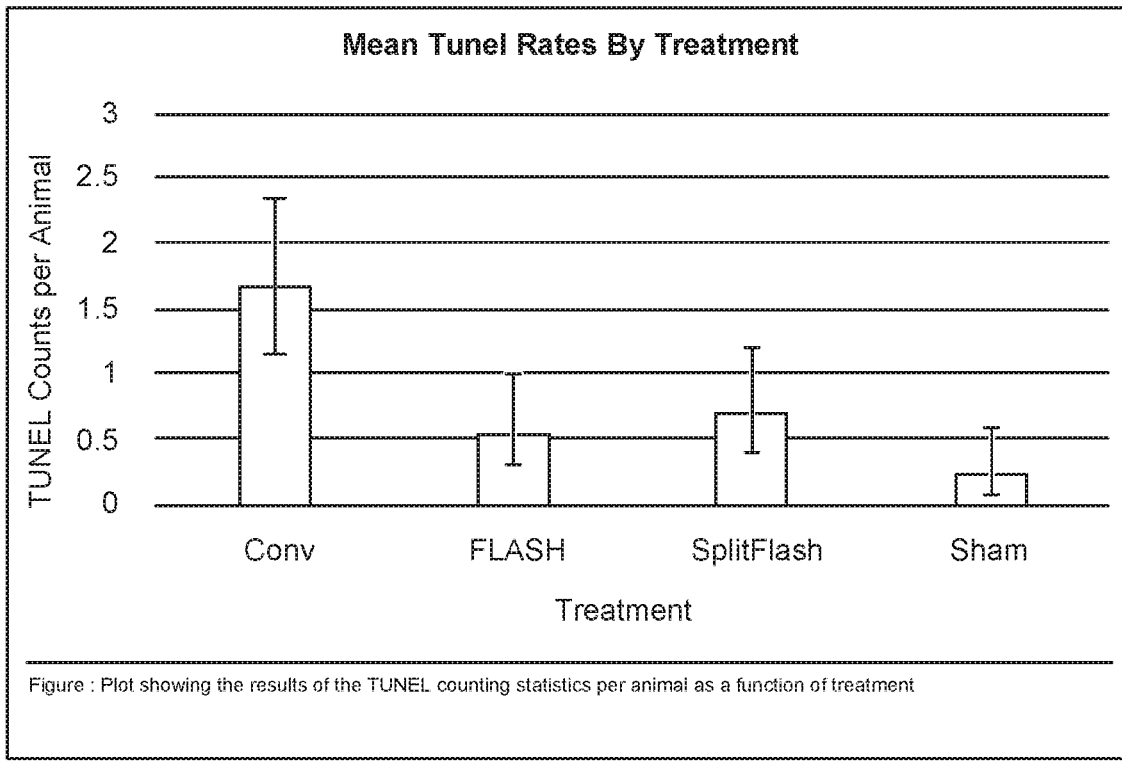
FIG. 24 is a graph showing the TUNEL results. The graph shows the average number of counts per animal for the roughly 20 animals per group (males and females pooled).

FIG. 24 is a graph showing the TUNEL results. The graph shows the average number of counts per animal for the roughly 20 animals per group (males and females pooled). Quantifying TUNEL cells constitutes a counting problem in which the number of TUNEL positive cells is counted per group of animal samples and therefor should follow Poisson statistics. The eaprror bars on the chart indicate the 95% confidence intervals calculated using the exact estimation method articulated by Ulm et al. (Ulm, K., "A simple method to calculate the confidence interval of a standardized mortality ratio (SMR)", Am J Epidemiol, 1990, 131(2):373-5). The overlap of 95% confidence intervals indicates that SplitFlash (pulsed Flash) and FLASH are more similar to Sham than Conventional, thereby indicating a lower occurrence of apoptosis for these novel treatment techniques.

Table 2: 24 Hours Top Enriched Pathways

TABLE 2A

| Conventional Versus Sham: | | | |
|---|---|---|---|
| Hallmark Pathways | NES | NOM p-val | FDR q-val |
| HALLMARK_PANCREAS_BETA_CELLS | −1.53295 | 0.017857 | 0.109607 |
| HALLMARK_G2M_CHECKPOINT | −1.52134 | 0.020704 | 0.083659 |
| HALLMARK_E2F_TARGETS | −1.50024 | 0.008529 | 0.074088 |
| HALLMARK_SPERMATOGENESIS | −1.4566 | 0.029536 | 0.10317 |

TABLE 2B

| Flash Versus Sham: | | | |
|---|---|---|---|
| Hallmark Pathways | NES | NOM p-val | FDR q-val |
| HALLMARK_MITOTIC_SPINDLE | −1.75448 | 0.003968 | 0.04197 |
| HALLMARK_G2M_CHECKPOINT | −1.73351 | 0.001 | 0.024433 |
| HALLMARK_E2F_TARGETS | −1.64836 | 0.005988 | 0.063113 |
| HALLMARK_ALLOGRAFT_REJECTION | −1.57263 | 0.026465 | 0.132354 |
| HALLMARK_DNA_REPAIR | −1.50316 | 0.041016 | 0.208294 |

TABLE 2C

| Split Flash Versus Sham | | | |
|---|---|---|---|
| Hallmark Pathways | NES | NOM p-val | FDR q-val |
| HALLMARK_INTERFERON_ALPHA_RESPONSE | 1.638147 | 0.009653 | 0.218787 |
| HALLMARK_G2M_CHECKPOINT | −1.6643 | 0.001 | 0.042827 |
| HALLMARK_E2F_TARGETS | −1.61984 | 0.001 | 0.040858 |
| HALLMARK_MITOTIC_SPINDLE | −1.61318 | 0.018145 | 0.031744 |

Table 3: 8 Weeks Top Enriched Pathways

TABLE 3A

| Conventional Versus Sham: | | | |
|---|---|---|---|
| Hallmark Pathways | NES | NOM p-val | FDR q-val |
| HALLMARK_CHOLESTEROL_HOMEOSTASIS | 1.617632 | 0.008602 | 0.248289 |
| HALLMARK_P53_PATHWAY | 1.588453 | 0.018595 | 0.186156 |
| HALLMARK_ANGIOGENESIS | 1.565956 | 0.001 | 0.148027 |
| HALLMARK_UV_RESPONSE_UP | 1.548823 | 0.002079 | 0.13248 |
| HALLMARK_MITOTIC_SPINDLE | 1.545859 | 0.012579 | 0.109196 |
| HALLMARK_GLYCOLYSIS | 1.529345 | 0.024948 | 0.102192 |
| HALLMARK_MTORC1_SIGNALING | 1.526473 | 0.033058 | 0.089846 |
| HALLMARK_TNFA_SIGNALING_VIA_NFKB | 1.5244 | 0.002088 | 0.081271 |
| HALLMARK_HYPOXIA | 1.510582 | 0.012552 | 0.084011 |
| HALLMARK_APOPTOSIS | 1.506349 | 0.008493 | 0.071817 |
| HALLMARK_ANDROGEN_RESPONSE | 1.466681 | 0.021277 | 0.095276 |
| HALLMARK_PI3K_AKT_MTOR_SIGNALING | 1.462443 | 0.04277 | 0.091787 |
| HALLMARK_EPITHELIAL_MESENCHYMAL_TRANSITION | 1.444373 | 0.027542 | 0.102013 |
| HALLMARK_COAGULATION | 1.432815 | 0.033543 | 0.106049 |
| HALLMARK_COMPLEMENT | 1.429856 | 0.004301 | 0.095217 |
| HALLMARK_KRAS_SIGNALING_UP | 1.423249 | 0.018828 | 0.095705 |
| HALLMARK_INFLAMMATORY_RESPONSE | 1.390631 | 0.035124 | 0.114034 |
| HALLMARK_IL2_STAT5_SIGNALING | 1.311629 | 0.038136 | 0.18504 |

TABLE 3B

| Flash Versus Sham: | | | |
|---|---|---|---|
| Hallmark Pathways | NES | NOM p-val | FDR q-val |
| HALLMARK_COAGULATION | 1.406174 | 0.045714 | 0.225907 |
| HALLMARK_TNFA_SIGNALING_VIA_NFKB | 1.382228 | 0.036329 | 0.225861 |
| HALLMARK_APICAL_JUNCTION | 1.3685 | 0.016 | 0.231629 |
| HALLMARK_WNT_BETA_CATENIN_SIGNALING | 1.361896 | 0.02924 | 0.227167 |
| HALLMARK_KRAS_SIGNALING_UP | 1.351275 | 0.043561 | 0.228315 |

Table 4: 16 Weeks Top Enriched Pathways

TABLE 4A

| Conventional Versus Sham: | | | |
|---|---|---|---|
| Hallmark Pathways | NES | NOM p-val | FDR q-val |
| HALLMARK_COAGULATION | 1.5755655 | 0.001 | 0.17153585 |
| HALLMARK_HEDGEHOG_SIGNALING | −1.6175224 | 0.0056926 | 0.032724753 |

10

TABLE 4B

| Flash Versus Sham: | | | |
|---|---|---|---|
| Hallmark Pathway | NES | NOM p-val | FDR q-val |
| EPITHELIAL_MESENCHYMAL_TRANSITION | 1.5123537 | 0.0116505 | 0.2488241 |
| HALLMARK_COAGULATION | 1.4792827 | 0.0223577 | 0.2174025 |
| HALLMARK_APOPTOSIS | 1.446631 | 0.0371094 | 0.24221855 |
| HALLMARK_KRAS_SIGNALING_UP | 1.438819 | 0.0233463 | 0.22549081 |
| HALLMARK_HYPOXIA | 1.4367952 | 0.0039526 | 0.20197491 |
| HALLMARK_MYOGENESIS | 1.406268 | 0.0380228 | 0.2080547 |

TABLE 4C

25

| Flash Versus Sham: | | | |
|---|---|---|---|
| Hallmark Pathway | NES | NOM p-val | FDR q-val |
| HALLMARK_P53_PATHWAY | 1.5119545 | 0.0087912 | 0.24653515 |

30

NES = Normalized Enrichment Score,
Nom p-val = Normalized -values,
FD-q-val = False Discovery Rate value Table 5: 24 Weeks Top Enriched Pathways

TABLE 5A

| Conventional Versus Sham: | | | |
|---|---|---|---|
| Hallmark Pathways | NES | NOM p-val | FDR q-val |
| EPITHELIAL_MESENCHYMAL_TRANSITION | 1.715518 | 0.001 | 0.066558 |
| HALLMARK_P53_PATHWAY | 1.657078 | 0.002045 | 0.065537 |
| HALLMARK_COAGULATION | 1.629851 | 0.001 | 0.062578 |
| HALLMARK_IL2_STAT5_SIGNALING | 1.566532 | 0.004016 | 0.099271 |
| HALLMARK_INFLAMMATORY_RESPONSE | 1.559741 | 0.014257 | 0.090297 |
| HALLMARK_HYPOXIA | 1.546812 | 0.004124 | 0.087968 |
| HALLMARK_ALLOGRAFT_REJECTION | 1.517242 | 0.028169 | 0.107425 |
| HALLMARK_INTERFERON_GAMMA_RESPONSE | 1.513903 | 0.010101 | 0.098017 |
| HALLMARK_MITOTIC_SPINDLE | 1.505295 | 0.021359 | 0.094306 |
| HALLMARK_E2F_TARGETS | 1.502026 | 0.032882 | 0.088742 |
| HALLMARK_MYC_TARGETS_V2 | 1.496078 | 0.026477 | 0.085209 |
| HALLMARK_GLYCOLYSIS | 1.465007 | 0.035928 | 0.10566 |
| HALLMARK_KRAS_SIGNALING_UP | 1.45314 | 0.044715 | 0.084997 |
| HALLMARK_APICAL_JUNCTION | 1.447435 | 0.02008 | 0.078949 |
| HALLMARK_ESTROGEN_RESPONSE_LATE | 1.287919 | 0.041667 | 0.181257 |

TABLE 5B

| Flash Versus Sham: | | | |
|---|---|---|---|
| Hallmark Pathways | NES | NOM p-val | FDR q-val |
| HALLMARK_COAGULATION | 1.754068 | 0.001 | 0.030982 |
| EPITHELIAL_MESENCHYMAL_TRANSITION | 1.743082 | 0.002066 | 0.017006 |
| HALLMARK_MYC_TARGETS_V2 | 1.66075 | 0.014056 | 0.036597 |
| HALLMARK_GLYCOLYSIS | 1.598933 | 0.004193 | 0.076556 |
| HALLMARK_IL6_JAK_STAT3_SIGNALING | 1.580787 | 0.006098 | 0.078151 |

TABLE 5B-continued

| Flash Versus Sham: | | | |
|---|---|---|---|
| Hallmark Pathways | NES | NOM p-val | FDR q-val |
| HALLMARK_IL2_STAT5_SIGNALING | 1.571376 | 0.011858 | 0.07368 |
| HALLMARK_MITOTIC_SPINDLE | 1.553222 | 0.001927 | 0.075656 |
| HALLMARK_INFLAMMATORY_RESPONSE | 1.522947 | 0.029528 | 0.093476 |
| HALLMARK_HYPOXIA | 1.468816 | 0.001972 | 0.130024 |
| HALLMARK_APOPTOSIS | 1.416187 | 0.03937 | 0.141715 |
| HALLMARK_XENOBIOTIC_METABOLISM | 1.390655 | 0.030181 | 0.151785 |
| HALLMARK_ESTROGEN_RESPONSE_LATE | 1.348313 | 0.023715 | 0.158576 |
| HALLMARK_ESTROGEN_RESPONSE_EARLY | 1.327884 | 0.02449 | 0.175084 |

NES = Normalized Enrichment Score, Nom p-val = Normalized -values, FDR-q-val = False Discovery Rate value.

Table 6: 24 Hours Top Canonical Pathways by IPA

TABLE 6A

| Conventional Versus Sham: | | | |
|---|---|---|---|
| Ingenuity Canonical Pathways | Neg LogP value | Ratio | Z score |
| Cyclins_and_Cell_Cycle_Regulation | 1.09 | 2.05E−01 | 1.941 |
| GP6_Signaling_Pathway | 1.03 | 1.76E−01 | 3.545 |
| STAT3_Pathway | 1.09 | 1.96E−01 | 1.606 |
| Phospholipase_C_Signaling | 1.09 | 1.60E−01 | 2.785 |
| Colorectal_Cancer_Metastasis_Signaling | 1.19 | 1.60E−01 | 3.781 |
| Pancreatic_Adenocarcinoma_Signaling | 1.60 | 2.03E−01 | 2.183 |
| IL-8_Signaling | 1.60 | 1.79E−01 | 4.352 |
| Interferon_Signaling | 1.75 | 3.45E−01 | 2.333 |
| Salvage_Pathways_of_Pyrimidine_Ribonucleotides | 1.88 | 2.31E−01 | 1.528 |

TABLE 6B

| Flash Versus Sham: | | | |
|---|---|---|---|
| Ingenuity Canonical Pathways | Neg LogP value | Ratio | Z score |
| Mitotic_Roles_of_Polo-Like_Kinase | 8.52 | 1.97E−01 | −1.667 |
| Estrogen-mediated_S-phase_Entry | 2.30 | 1.54E−01 | −2 |
| Aryl_Hydrocarbon_Receptor_Signaling | 2.30 | 6.11E−02 | −2.121 |
| Cyclins_and_Cell_Cycle_Regulation | 2.13 | 7.69E−02 | −2.449 |
| Th1_Pathway | 1.99 | 6.03E−02 | −2.236 |

TABLE 6B-continued

| Flash Versus Sham: | | | |
|---|---|---|---|
| Ingenuity Canonical Pathways | Neg LogP value | Ratio | Z score |
| Calcium-induced_T_Lymphocyte_Apoptosis | 1.30 | 7.27E−02 | −2 |
| Dendritic_Cell_Maturation | 1.30 | 4.29E−02 | −1.633 |

TABLE 6C

| Split Flash Versus Sham | | | |
|---|---|---|---|
| Ingenuity Canonical Pathways | Neg LogP value | Ratio | Z score |
| Cell Cycle: G2/M DNA Damage Checkpoint Regulation | 1.15E+01 | 3.00E−01 | 1.604 |
| Mitotic Roles of Polo-Like Kinase | 7.00E+00 | 1.97E−01 | −1.897 |
| p53 Signaling | 7.00E+00 | 1.40E−01 | 1.508 |
| Aryl Hydrocarbon Receptor Signaling | 3.58E+00 | 9.16E−02 | −1.897 |
| Cyclins and Cell Cycle Regulation | 1.94E+00 | 8.97E−02 | −1.89 |
| Estrogen-mediated S-phase Entry | 1.67E+00 | 1.54E−01 | −2 |

References

Ashworth, A., and Lord, C. J. (2018). Synthetic lethal therapies for cancer: what's next after PARP inhibitors? Nat. Rev. Clin. Oncol. 1.

Asteriti, I. A., De Mattia, F., and Guarguaglini, G. (2015). Cross-Talk between AURKA and Plk1 in Mitotic Entry and Spindle Assembly. Front. Oncol. 5.

Benjamini, Y., and Hochberg, Y. (1995). Controlling the False Discovery Rate: A Practical and Powerful Approach to Multiple Testing. J. R. Stat. Soc. Ser. B Methodol. 57, 289-300.

Bolstad, B. M., Irizarry, R. A., Åstrand, M., and Speed, T. P. (2003). A comparison of normalization methods for high density oligonucleotide array data based on variance and bias. Bioinformatics 19, 185-193.

Donnella, H. J., Webber, J. T., Levin, R. S., Camarda, R., Momcilovic, O., Bayani, N., Shah, K. N., Korkola, J. E., Shokat, K. M., Goga, A., et al. (2018). Kinome rewiring reveals AURKA limits PI3K-pathway inhibitor efficacy in breast cancer. Nat. Chem. Biol.

Downward, J. (2003). Targeting RAS signalling pathways in cancer therapy. Nat. Rev. Cancer 3, 11-22.

Foroutan, M., Cursons, J., Hediyeh-Zadeh, S., Thompson, E. W., and Davis, M. J. (2017). A Transcriptional Program for Detecting TGFβ-Induced EMT in Cancer. Mol. Cancer Res. MCR 15, 619-631.

Hainfeld, J F et al. (2004). The use of gold nanoparticles to enhance radiotherapy in mice. Phys Med Biol.

Janeček, M., Rossmann, M., Sharma, P., Emery, A., Huggins, D. J., Stockwell, S. R., Stokes, J. E., Tan, Y. S., Almeida, E. G., Hardwick, B., et al. (2016). Allosteric modulation of AURKA kinase activity by a small-molecule inhibitor of its protein-protein interaction with TPX2. Sci. Rep. 6, 28528.

Kitai, H., and Ebi, H. (2016). Key roles of EMT for adaptive resistance to MEK inhibitor in KRAS mutant lung cancer. Small GTPases 0, 00-00.

Liang, S.-Q., Marti, T. M., Dorn, P., Froment, L., Hall, S. R. R., Berezowska, S., Kocher, G., Schmid, R. A., and Peng, R.-W. (2015). Blocking the epithelial-to-mesenchymal transition pathway abrogates resistance to antifolate chemotherapy in lung cancer. Cell Death Dis. 6, e1824.

Lin, Y et al. (2014). Comparing gold nano-particle enhanced radiotherapy with protons, megavoltage photons and kilovoltage photons: a Monte Carlo simulation. Phys Med Biol.

Lord, C. J., and Ashworth, A. (2016). BRCAness revisited. Nat. Rev. Cancer 16, 110-120.

Murai, J., Huang, S. N., Das, B. B., Renaud, A., Zhang, Y., Doroshow, J. H., Ji, J., Takeda, S., and Pommier, Y. (2012). Trapping of PARP1 and PARP2 by Clinical PARP Inhibitors. Cancer Res. 72, 5588-5599.

Panicker, R. C., Coyne, A. G., and Srinivasan, R. (2017). Allosteric Targeting of Aurora A Kinase Using Small Molecules: A Step Forward Towards Next Generation Medicines? Curr. Med. Chem.

Ritchie, M. E., Phipson, B., Wu, D., Hu, Y., Law, C. W., Shi, W., and Smyth, G. K. (2015). limma powers differential expression analyses for RNA-sequencing and microarray studies. Nucleic Acids Res. 43, e47.

Stapleton, S et al. (2017). Radiation effects on the tumor microenvironment: Implications for nanomedicine delivery. Adv Drug Deliv Rev.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: A knowledge-based approach for interpreting genome-wide expression profiles. Proc. Natl. Acad. Sci. U.S.A. 102, 15545-15550.

Sun, Y., Liu, W.-Z., Liu, T., Feng, X., Yang, N., and Zhou, H.-F. (2015). Signaling pathway of MAPK/ERK in cell proliferation, differentiation, migration, senescence and apoptosis. J. Recept. Signal Transduct. Res. 35,600-604.

Wang, M., Morsbach, F., Sander, D., Gheorghiu, L., Nanda, A., Benes, C., Kriegs, M., Krause, M., Dikomey, E., Baumann, M., et al. (2011). EGF Receptor Inhibition Radiosensitizes NSCLC Cells By Inducing Senescence In Cells Sustaining DNA Double-Strand Breaks. Cancer Res. 71, 6261-6269.

[1] T. Nishimura, K. Iwakabe, M. Sekimoto, Y. Ohmi, T. Yahata, M. Nakui, T. Sato, S. Habu, H. Tashiro, M. Sato, A. Ohta, Distinct role of antigen-specific T helper type 1 (Th1) and Th2 cells in tumor eradication in vivo, J Exp Med, 190 (1999) 617-627.

[2] H. M. Xu, Th1 cytokine-based immunotherapy for cancer, Hepatobiliary Pancreat Dis Int, 13 (2014) 482-494.

[3] G. E. Kaiko, J. C. Horvat, K. W. Beagley, P. M. Hansbro, Immunological decision-making: how does the immune system decide to mount a helper T-cell response?, Immunology, 123 (2008) 326-338.

[4] G. Hasko, C. Szabo, IL-12 as a therapeutic target for pharmacological modulation in immune-mediated and inflammatory diseases: regulation of T helper 1/T helper 2 responses, Br J Pharmacol, 127 (1999) 1295-1304.

[5] C. Tang, Z. Liao, D. Gomez, L. Levy, Y. Zhuang, R. A. Gebremichael, D. S. Hong, R. Komaki, J. W. Welsh, Lymphopenia association with gross tumor volume and lung V5 and its effects on non-small cell lung cancer patient outcomes, Int J Radiat Oncol Biol Phys, 89 (2014) 1084-1091.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

What is claimed is:

1. A method of identifying a subject with cancer as a candidate for a treatment comprising ultra-high-dose-rate radiation (FLASH RT), the method comprising:

(a) determining an expression level of one or more biomarkers in a tumor sample from the subject, wherein the one or more biomarkers are selected from the group consisting of an immune cell marker, a tumor cell marker, a circulating marker, an imaging marker, and any combination thereof;

(b) comparing the expression level of the one or more biomarkers in the tumor sample from the subject to an expression level of the one or more biomarkers in a normal tissue sample; and (c) classifying the subject as a candidate for a treatment comprising FLASH RT if the expression level of the one or more biomarkers in the tumor sample from the subject is modified compared to the expression level of the one or more biomarkers in the normal tissue sample.

2. The method of claim 1, wherein the one or more biomarkers is CD44, MMP9, ALDH1A1, Vimentin, hyaluronan, beta-catenin, MFG-E8, CD68, TGFβ, or a TGFβ-pathway related biomarker.

3. The method of claim 1, wherein the tumor sample from the subject is a biopsy comprising tumor cells.

4. The method of claim 1, wherein the normal tissue sample comprises non-tumor cells from the same tissue type as the subject's cancer.

5. The method of claim 1, wherein the subject with cancer is classified as a candidate for a treatment comprising FLASH RT if the expression level of CD44 is increased and/or the expression level of MFG-E8 is decreased in the tumor sample from the subject relative to the expression level in a normal or control tissue sample.

6. The method of claim 1, wherein the subject with cancer is classified as a candidate for a treatment comprising FLASH RT if the expression level of CD68 is increased in the tumor sample from the subject relative to the expression level in a normal or control tissue sample.

7. A method of selecting a treatment for a subject with cancer, the method comprising:

(a) determining an expression level of one or more biomarkers in a tumor sample from the subject, wherein the one or more biomarkers are selected from the group consisting of an immune cell marker, a tumor cell marker, a circulating marker, and any combination thereof;

(b) comparing the expression level of the one or more biomarkers in the tumor sample from the subject to an expression level of the one or more biomarkers in a normal tissue sample; and (c) administering a treatment comprising an effective amount of FLASH RT if the expression level of the one or more biomarkers in the tumor sample from the subject is modified compared to the expression level of the one or more biomarkers in the normal tissue sample.

8. The method of claim 7, wherein the one or more biomarkers is CD44, MMP9, ALDH1A1, Vimentin, hyaluronan, beta-catenin, MFG-E8, CD68, TGFβ, or a TGFβ-pathway related biomarker.

9. The method of claim 7, wherein the tumor sample from the subject is a biopsy comprising tumor cells.

10. The method of claim 7, wherein the normal tissue sample comprises non-tumor cells from the same tissue type as the subject's cancer.

11. The method of claim 7, wherein the effective amount of FLASH RT is increased from a current effective amount if the subject is already undergoing a radiation therapy for a tumor.

12. The method of claim 7, wherein the effective amount of FLASH RT administered to a tumor is increased if the expression level of the one or more biomarkers in the tumor sample from the subject is elevated in a tumor environment.

13. The method of claim 7, wherein the treatment comprising the effective amount of FLASH RT comprises protons or consists of protons.

14. The method of claim 7, wherein the effective amount of FLASH RT is 10 to 200 gray (Gy).

15. The method of claim 7, wherein the effective amount of FLASH RT is 5 to 500 gray (Gy).

16. The method of claim 7, wherein the effective amount of FLASH RT is administered in multiple fractions of 3 Gy to 20 Gy per fraction.

17. The method of claim 7, wherein the effective amount of FLASH RT is administered at a dose per pulse of at least 0.1 Gy.

\* \* \* \* \*